Figure 1A:
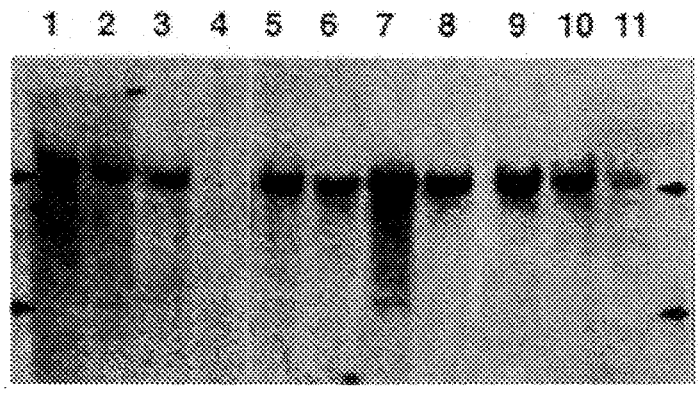

United States Patent [19]

Wilks et al.

[11] Patent Number: 5,658,791
[45] Date of Patent: Aug. 19, 1997

[54] ANTIBODIES WHICH SPECIFICALLY BIND TO PROTEINS HAVING TYROSINE KINASE ACTIVITY, WHEREIN SAID PROTEINS HAVE MORE THAN ONE TYROSINE KINASE DOMAIN, AND NO SH2 DOMAINS

[75] Inventors: Andrew Frederick Wilks, Doneaster East, Australia; Andrew Ziemiecki, Berne, Switzerland; Ailsa Harpur, Mooroolbark, Australia

[73] Assignee: Ludwig Institute For Cancer Research, New York, N.Y.

[21] Appl. No.: 446,038

[22] Filed: May 19, 1995

Related U.S. Application Data

[62] Division of Ser. No. 64,067, Jun. 30, 1993.

[30] Foreign Application Priority Data

Nov. 28, 1990 [AU] Australia ............................. PK359/90

[51] Int. Cl.$^6$ .............................. C07K 16/18; C12N 5/12
[52] U.S. Cl. .................. 435/331; 530/387.9; 530/388.1; 530/388.25; 530/388.26; 530/388.85; 530/389.1; 435/338

[58] Field of Search .................. 530/387.9, 388.1, 530/388.26, 388.25, 389.1; 435/240.27; 424/130.1, 139.1

[56] References Cited

U.S. PATENT DOCUMENTS 4,543,539  9/1985  Frackelton.

OTHER PUBLICATIONS

Hunter, Cell 50:823–829, 1987.

*Primary Examiner*—Lila Feisee
*Assistant Examiner*—Nancy A. Johnson
*Attorney, Agent, or Firm*—Felfe & Lynch

[57] ABSTRACT

The invention relates to antibodies which specifically bind to tyrosine kinase active proteins. The proteins have more than one protein kinase domain, and no SH2 domains. Exemplary proteins are the Janus Kinases, or "JAK1" and "JAK2". Both polyclonal and monoclonal antibodies are a part of the invention, as are hybridomas which produce the monoclonal antibodies.

9 Claims, 34 Drawing Sheets

FIG. 2A

```
TGGCCGCCTA GCGAGCTGCC GGTCGACCCC AGCCAGCCGA GCGACGGGCG CTGCCTGGCC  60
CAGGGCACAC GGAAGTGCGC TTCTCTGAAG TAGCTTTGGA AAGTAGAGAA GAAAATCCAG 120
TTTGCTTCTT GGAGAACACT GGACAGCTGA ATAA ATG CAG TAT CTA AAT         169
                                    Met Gln Tyr Leu Asn
                                                    -10

ATA AAA GAG GAC TGC AAT GCC ATG GCT TTC TGT GCT AAA ATG AGG       214
Ile Lys Glu Asp Cys Asn Ala Met Ala Phe Cys Ala Lys Met Arg
            -5                  +1                  5

AGC TCC AAG AAG ACT GAG GTG AAC CTG GAG GCC CCT GAG CCA GGG       259
Ser Ser Lys Lys Thr Glu Val Asn Leu Glu Ala Pro Glu Pro Gly
                10                  15                  20

GTG GAA GTG ATC TTC TAT CTG TCG GAC AGG GAG CCC CTC CGG CTG       304
Val Glu Val Ile Phe Tyr Leu Ser Asp Arg Glu Pro Leu Arg Leu
            25                  30                  35

GGC AGT GGA GAG TAC ACA GCA GAG GAA CTG TGC ATC AGG GCT GCA       349
Gly Ser Gly Glu Tyr Thr Ala Glu Glu Leu Cys Ile Arg Ala Ala
            40                  45                  50
```

FIG. 2B

```
CAG TGC CGT ATC TCT CCT CTT TGT CAC AAC CTC TTT GCC CTG       394
Gln Ala Cys Arg Ile Ser Pro Leu Cys His Asn Leu Phe Ala Leu
 55                  60                  65

TAT GAC GAG AAC ACC AAG CTC TGG TAT GCT CCA AAT CGC ACC ATC   439
Tyr Asp Glu Asn Thr Lys Leu Trp Tyr Ala Pro Asn Arg Thr Ile
         70                  75                  80

ACC GTT GAT GAC AAG ATG TCC CGG CTC CAC TAC CGG ATG AGG       484
Thr Val Asp Asp Lys Met Ser Arg Leu His Tyr Arg Met Arg
 85                  90                  95

TTC TAT TTC ACC AAT TGG CAT GGA ACC AAC GAC AAT GAG CAG TCA   529
Phe Tyr Phe Thr Asn Trp His Gly Thr Asn Asp Asn Glu Gln Ser
        100                 105                 110

GTG TGG CGT CAT TCT CCA GAT GCA ACC CCT CTC CTT GAT GCC AGC   574
Val Trp Arg His Ser Pro Asp Ala Thr Pro Leu Leu Asp Ala Ser
        115                 120                 125

AAA AAG ATT CCA GAT GCA ACC CCT CTC CTT GAT GCC AGC           619
Lys Lys Ile Pro Asp Ala Thr Pro Leu Leu Asp Ala Ser
        130                 135                 140

GAG TAT CTG TTT GCT CAG GGA CAG TAT GAT TTG GTG AAA TGC CTG   664
Glu Tyr Leu Phe Ala Gln Gly Gln Tyr Asp Leu Val Lys Cys Leu
        145                 150                 155
```

FIG. 2C

```
GCT CCT ATT CGA GAC CCC AAG ACC GAG CAG GAT GGA CAT GAT ATT    709
Ala Pro Ile Arg Asp Pro Lys Thr Glu Gln Asp Gly His Asp Ile
160                 165                 170

GAG AAC GAG TGT CTA GGG ATG GCT GTC CTG GCC ATC TCA CAC TAT    754
Glu Asn Glu Cys Leu Gly Met Ala Val Leu Ala Ile Ser His Tyr
        175                 180                 185

GCC ATG AAG AAG ATG AAG CAG TTG CCA GAA CTG CCC AAG GAC ATC    799
Ala Met Lys Lys Met Lys Gln Leu Pro Glu Leu Pro Lys Asp Ile
190                 195                 200

AGC TAC AAG CGA TAT ATT CCA GAA ACA AGG ATG CGG ATA AAT GTT TTC AAG TCC ATC AGA    844
Ser Tyr Lys Arg Tyr Ile Pro Glu Thr Arg Met Arg Ile Lys Ser Ile Arg
        205                 210                 215

CAG AGG AAC CTT CTC ACC AGG ATG CGG ATA AAT GTT TTC AAG       889
Gln Arg Asn Leu Leu Thr Arg Met Arg Ile Asn Val Phe Lys
220                 225                 230

GAT TTC CTA AAG GAA TTT AAC AAC AAG ACC ATT TGT GAC AGC AGC    934
Asp Phe Leu Lys Glu Phe Asn Asn Lys Thr Ile Cys Asp Ser Ser
        235                 240                 245
```

FIG. 2D

```
GTG TCC ACG CAT GAC CTG AAG GTG AAA TAC TTG GCT ACC TTG GAA                979
Val Ser Thr His Asp Leu Lys Val Lys Tyr Leu Ala Thr Leu Glu
         250                 255                 260

ACT TTG ACA AAA CAT TAC GGT GCT GAA ATA TTT GAG ACT TCC ATG                1024
Thr Leu Thr Lys His Tyr Gly Ala Glu Ile Phe Glu Thr Ser Met
         265                 270                 275

TTA CTG ATT TCA GAA TCA AAT GAG ATG AAT TGG TTT CAT TCG AAT                1069
Leu Leu Ile Ser Glu Ser Asn Glu Met Asn Trp Phe His Ser Asn
         280                 285                 290

GAC GGT GGA AAC GTT CTC TAC TAC GAA GTG ATG GTG ACT GGG AAT                1114
Asp Gly Gly Asn Val Leu Tyr Tyr Glu Val Met Val Thr Gly Asn
         295                 300                 305

CTT GGA ATC CAG TGG AGG CAT AAA CCA AAT GTT TCT GTT GAA                    1159
Leu Gly Ile Gln Trp Arg His Lys Pro Asn Val Ser Val Glu
         310                 315                 320

AAG GAA AAA AAT AAA CTG AAG CGG AAA AAA CTG GAA AAT AAA GAC                1204
Lys Glu Lys Asn Lys Leu Lys Arg Lys Lys Leu Glu Asn Lys Asp
         325                 330                 335

AAG GAT GAG GAG AAA AAC AAG ATC CGG GAA GAG TGG AAC AAT                    1249
Lys Asp Glu Glu Lys Asn Lys Ile Arg Glu Glu Trp Asn Asn
         340                 345                 350
```

FIG. 2E

```
TTT TCA TTC TTC CCT GAA ATC ACT CAC ATT GTA ATA AAG GAG TCT    1294
Phe Ser Phe Phe Pro Glu Ile Thr His Ile Val Ile Lys Glu Ser
    355                 360                 365

GTG GTC AGC ATT AAC AAG CAG GAC AAC AAG AAA ATG GAA CTG AAG    1339
Val Val Ser Ile Asn Lys Gln Asp Asn Lys Lys Met Glu Leu Lys
    370                 375                 380

CTC TCT TCC CAC GAG GAG GCC TTG TCC TTT GTG TCC CTG GTA GAT    1384
Leu Ser Ser His Glu Glu Ala Leu Ser Phe Val Ser Leu Val Asp
    385                 390                 395

GGC TAC TTC CGG CTC ACA GCA GAT GCC CAT TAC CAT TAC CTC TGC ACC    1429
Gly Tyr Phe Arg Leu Thr Ala Asp Ala His His Tyr Leu Cys Thr
    400                 405                 410

GAC GTG GCC CCC CCG TTG ATC GTC CAC AAC ATA CAG AAT GGC TGT    1474
Asp Val Ala Pro Pro Leu Ile Val His Asn Ile Gln Asn Gly Cys
    415                 420                 425

CAT GGT CCA ATC TGT ACA GAA TAC GCC ATC AAT AAA TTG CGG CAA    1519
His Gly Pro Ile Cys Thr Glu Tyr Ala Ile Asn Lys Leu Arg Gln
    430                 435                 440
```

FIG. 2F

```
GAA AGC GAG GAG GGG ATG TAC GTG CTG AGG TGG AGC TGC ACC      1564
Glu Ser Glu Glu Gly Met Tyr Val Leu Arg Trp Ser Cys Thr
            445                 450                 455

GAC TTT GAC AAC ATC CTC ATG ACC GTC ACC TGC TTT GAG AAG TCT  1609
Asp Phe Asp Asn Ile Leu Met Thr Val Thr Cys Phe Glu Lys Ser
    460                 465                 470

GAG CAG GTG CAG GGT GCC CAG AAG CAG TTC AAG AAC TTT CAG ATC  1654
Glu Gln Val Gln Gly Ala Gln Lys Gln Phe Lys Asn Phe Gln Ile
        475                 480                 485

GAG GTG CAG AAG GGC TAC AGT CTG CAC GGT TCG GAC CGC AGC      1699
Glu Val Gln Lys Gly Tyr Ser Leu His Gly Ser Asp Arg Ser
            490                 495                 500

TTC CCC AGC TTG GGA GAC CTC ATG AGC CAC CTC AAG AAG CAG ATC  1744
Phe Pro Ser Leu Gly Asp Leu Met Ser His Leu Lys Lys Gln Ile
    505                 510                 515

CTG CGC ACG GAT AAC ATC AGC TTC ATG CTA AAA CGC TGC TGC CAG  1789
Leu Arg Thr Asp Asn Ile Ser Phe Met Leu Lys Arg Cys Cys Gln
        520                 525                 530
```

FIG. 2G

```
CCC AAG CCC CGA GAA ATC TCC AAC CTG CTG GTG GCT ACT AAG AAA    1834
Pro Lys Pro Arg Glu Ile Ser Asn Leu Leu Val Ala Thr Lys Lys
535                 540                 545

GCC CAG GAG TGG CAG CCC TAC GTC TAC CCC ATG AGC CAG CTG AGT TTC    1879
Ala Gln Glu Trp Gln Pro Val Tyr Pro Met Ser Gln Leu Ser Phe
550                 555                 560

GAT CGG ATC CTC AAG AAG GAT CTG GTG CAG GGC GAG CAC CTT GGG    1924
Asp Arg Ile Leu Lys Lys Asp Leu Val Gln Gly Glu His Leu Gly
565                 570                 575
         Iₐ

AGA GGC ACG AGA ACA CAC ATC TAT TCT GGG ACC CTG ATG GAT TAC    1969
Arg Gly Thr Arg Thr His Ile Tyr Ser Gly Thr Leu Met Asp Tyr
580                 585                 590

AAG GAT GAC GAA GGA ACT TCT GAA GAG AAG ATA AAA GTG ATC        2014
Lys Asp Asp Glu Gly Thr Ser Glu Glu Lys Ile Lys Val Ile
595                 600                 605
    IIₐ

CTC AAA GTC TTA GAC CCC AGC CAC AGG GAT ATT TCC CTG GCC TTC    2059
Leu Lys Val Leu Asp Pro Ser His Arg Asp Ile Ser Leu Ala Phe
605                 615                 620
```

FIG. 2H

```
       IIIa                                                              IVa
     TTC GAG GCA GCC AGC ATG ATG AGA CAG GTC TCC CAC AAA CAC ATC          2104
     Phe Glu Ala Ala Ser Met Met Arg Gln Val Ser His Lys His Ile
                             625                 635

GTG TAC CTC TAT GGC GTC TGT GTC CGC GAC GTG GAG AAT ATC ATG          2149
     Val Tyr Leu Tyr Gly Val Cys Val Arg Asp Val Glu Asn Ile Met
                         640                 650
                                     Va
     GTG GAA GAG TTT GTG GAA GGG GGT CCT CTG GAT CTC TTC ATG CAC          2194
     Val Glu Glu Phe Val Glu Gly Gly Pro Leu Asp Leu Phe Met His
                     655                 660                 665

CGG AAA AGT GAT GTC CTT ACC ACA CCA TGG AAA TTC AAA GTT GCC          2239
     Arg Lys Ser Asp Val Leu Thr Thr Pro Trp Lys Phe Lys Val Ala
                 670                 675                 680

AAA CAG CTG GCC AGT GCC CTG AGC TAC TTG GAG GAT AAA GAC CTG          2284
     Lys Gln Leu Ala Ser Ala Leu Ser Tyr Leu Glu Asp Lys Asp Leu
             685                 690                 695
         VIa
     GTC CAT GGA AAT GTG TGT ACT AAA AAC CTC CTG GCC CGT GAG              2329
     Val His Gly Asn Val Cys Thr Lys Asn Leu Leu Ala Arg Glu
         700                 705                 710
```

FIG. 21

```
                                                      VIIa
GGA ATC GAC AGT GAG TGT GGC CCA TTC ATC AAG CTC AGT GAC CCC    2374
Gly Ile Asp Ser Glu Cys Gly Pro Phe Ile Lys Leu Ser Asp Pro
715                 720                 725

GGC ATC CCC ATT ACG GTG CTG TCT AGG CAA GAA TGC ATT GAA CGA    2419
Gly Ile Pro Ile Thr Val Leu Ser Arg Gln Glu Cys Ile Glu Arg
        730                 735                 740
                VIIIa
ATC CCA TGG ATT GCT CCT GAG TGT GTT GAG GAC TCC AAG AAC CTG    2464
Ile Pro Trp Ile Ala Pro Glu Cys Val Glu Asp Ser Lys Asn Leu
745                 750                 755
                                IXa
AGT GTG GCT GCT GAC AAG TGG AGC TTT GGA ACC ACG CTC TGG GAA    2509
Ser Val Ala Ala Asp Lys Trp Ser Phe Gly Thr Thr Leu Trp Glu
        760                 765                 770

ATC TGC TAC AAT GGC GAG ATC CCC TTG AAA GAC AAG ACG CTG ATT    2554
Ile Cys Tyr Asn Gly Glu Ile Pro Leu Lys Asp Lys Thr Leu Ile
775                 780                 785
                                        Xa
GAG AAA GAG AGA TTC TAT GAA AGC CGG TGC AGG TGC CCA GTG ACA CCA    2599
Glu Lys Glu Arg Phe Tyr Glu Ser Arg Cys Arg Cys Pro Val Thr Pro
        790                 795                 800
                                                        XIa
TCA TGT AAG GAG CTG GCT GAC CTC ATG ACC CGC TGC ATG AAC TAT    2644
Ser Cys Lys Glu Leu Ala Asp Leu Met Thr Arg Cys Met Asn Tyr
805                 810                 815
```

FIG. 2J

```
GAC CCC AAT CAG AGG CCT TTC TTC CGA GCC ATC ATG AGA GAC ATT    2689
Asp Pro Asn Gln Arg Pro Phe Phe Arg Ala Ile Met Arg Asp Ile
    820                 825                 830

AAT AAG CTT GAA GAG CAG CAT CCA GAT ATT GTT TCC AGA AAA AAA    2734
Asn Lys Leu Glu Glu Gln Asn Pro Asp Ile Val Ser Arg Lys Lys
    835                 840                 845

AAC CAG CCA ACT GAA GTG GAC CCC ACA CAT TTT GAG AAG CGC TTC    2779
Asn Gln Pro Thr Glu Val Asp Pro Thr His Phe Glu Lys Arg Phe
    850                 855                 860
                                    I

CTA AAG AGG ATC CGT GAC TTG GGA GAG GGC CAC TTT GGG AAG GTT    2824
Leu Lys Arg Ile Arg Asp Leu Gly Glu Gly His Phe Gly Lys Val
    865                 870                 875

GAG CTC TGC AGG TAT GAC TAT GAC CCC GAA GAC AAT ACA GGG GAG CAG GTG    2869
Glu Leu Cys Arg Tyr Asp Tyr Asp Pro Glu Asp Asn Thr Gly Glu Gln Val
    880                 885                 890
    II

GCT GTT AAA TCT CTG AAG CCT GAG AGT GGA GGT AAC CAC ATA GCT    2914
Ala Val Lys Ser Leu Lys Pro Glu Ser Gly Gly Asn His Ile Ala
    895                 900                 905
            III

GAT CTG AAA AAG GAA ATC TTA AGG ATC CTC TAT CAT GAG    2959
Asp Leu Lys Lys Glu Ile Leu Arg Ile Leu Tyr His Glu
    910                 915                 920
```

FIG. 2K

```
     IV
AAC ATT GTG AAG TAC AAA GGA ATC TGC ACA GAA GAC GGA GGA AAT    3004
Asn Ile Val Lys Tyr Lys Gly Ile Cys Thr Glu Asp Gly Gly Asn
    925                 930                 935
                                                 V
GGT ATT AAG CTC ATC ATG GAA TTT CTG CCT TCG GGA AGC CTT AAG    3049
Gly Ile Lys Leu Ile Met Glu Phe Leu Pro Ser Gly Ser Leu Lys
    940                 945                 950

GAA TAT CTT CCA AAG AAT AAA ATA AAC CTC AAA CAG CAG            3094
Glu Tyr Leu Pro Lys Asn Lys Ile Asn Leu Lys Gln Gln
    955                 960                 965

CTA AAA TAT GCC GTT CAG ATT TGT AAG GGG ATG GAC TAT TTG GGT    3139
Leu Lys Tyr Ala Val Gln Ile Cys Lys Gly Met Asp Tyr Leu Gly
    970                 975                 980
                             VI
TCT CGG CAA TAC GTT CAC CGG GAC TTG GCA GCA AGA AAT GTC CTT    3184
Ser Arg Gln Tyr Val His Arg Asp Leu Ala Ala Arg Asn Val Leu
    985                 990                 995
                                    VII
GTT GAG AGT GAA CAC CAA GTG AAA ATT GGA GAC TTC GGT TTA ACC    3229
Val Glu Ser Glu His Gln Val Lys Ile Gly Asp Phe Gly Leu Thr
    1000                1005                1010

AAA GCA ATT GAA ACC GAT AAG GAG TAT TAC ACC GTC AAG GAT GAC    3279
Lys Ala Ile Glu Thr Asp Lys Glu Tyr Tyr Thr Val Lys Asp Asp
    1015                1020                1025
```

FIG. 2L

```
        VIII
CGG GAC AGC CCT GTG TTT TGG TAT GCT CCA GAA TGT TTA ATG CAA      3319
Arg Asp Ser Pro Val Phe Trp Tyr Ala Pro Glu Cys Leu Met Gln
             1035                      1040
                                             IX
TCT AAA TTT TAT ATT GCC TCT GAC GTC TGG TCT TTT GGA GTC ACT      3364
Ser Lys Phe Tyr Ile Ala Ser Asp Val Trp Ser Phe Gly Val Thr
             1050                      1055

CTG CAT GAG CTG CTG ACT TAC TGT GAT TCA GAT TCT AGT CCC ATG      3409
Leu His Glu Leu Leu Thr Tyr Cys Asp Ser Asp Ser Ser Pro Met
             1065                      1070

GCT TTG TTC CTG AAA ATG ATA GGC CCA ACC CAT GGC CAG ATG ACA      3454
Ala Leu Phe Leu Lys Met Ile Gly Pro Thr His Gly Gln Met Thr
             1080                      1085
                                             X
GTC ACA AGA CTT GTG AAT ACG TTA AAA GAA GGA AAA CGC CTG CCG      3499
Val Thr Arg Leu Val Asn Thr Leu Lys Glu Gly Lys Arg Leu Pro
             1095                      1100

TGC CCA CCT AAC TGT CCA GAT GAG GTT TAT CAG CTT ATG AGA AAA      3544
Cys Pro Pro Asn Cys Pro Asp Glu Val Tyr Gln Leu Met Arg Lys
             1110                      1115
```

FIG. 2M

```
         XI
TGC TGG GAA TTC CAA CCA TCC AAT CGG ACA AGC TTT CAG AAC CTT    3589
Cys Trp Glu Phe Gln Pro Ser Asn Arg Thr Ser Phe Gln Asn Leu
    1120                    1125                    1130

ATT GAA GGA TTT GAA GCA CTT TTA AAA TAAGAAGCAT GAATAACATT
3636
Ile Glu Gly Phe Glu Ala Leu Leu Lys
            1135                1140

TAAATTCCAC AGATTATCAA GTCCTTCTCC TGCAACAAAT GCCCAAGTCA TTTTTAAAA3696
ATTTCTAATG AAAGAAGTTT GTGTTCTGTC CAAAAAGTCA CTGAACTCAT ACTTCAGTAC3756
ATATACATGT ATAAGGCACA CTGTAGTGCT TAATATGTGT AAGGACTTCC TCTTTAAATT3816
TGCACCAGTA ACTTAGTGAC ACATAAATGA AACCAAAATA TTTGAAAGCA CTTAAGCACT3876
CCTCCTTGTG GAAAGAATAT ACCACCATTT CATCTGGCTA GTTCACCATC ACAACTGCAT3936
TACCAAAAGG GGATTTTTGA AAACGAGGAG TTGACCAAAA TAATATCTGA AGATGATTGC3996
TTTTCCCTGC TGCCAGCTGA CTGAAATGTT TTCCTGGCAC ATTAATCATA GATAAAGAAG4056
ATTGATGGAC TTAGCCCTCA AACAGTATCT ATACAGTACT AGACCATGCA TTCTTAAAAT4116
ATTAGATACC AGGTAGTATA TATTGTTTCT GTACAAAAAT GACTGTATTC TCTCACCAGT4176
AGGACTTAAA CTTTGTTTCT CCAGTGGCTT AGCTCCCTGTT CCTTTGGGTG ATCACTAG  4234
```

FIG. 3A

```
           I                                           II                              III
Domain 1   HLGRGTRTHIYSGTLMDYKDDEGTSEEKKIKVLLKVLDPS...HRDISLAGGEAASM              -60aa-
Domain 2   DLGEGHFGKVELCRT.DPEDNTGE.......QVAVKSLKPES.GGNHIADLKKEIEIL              -63aa-
CDC2-H     KIGEGTYGVVYKGRH...KYYG......QVVAMKKIRLESEEEGVPSTAIREISLL                -55aa- VI                                              VII
Domain 1   SYLEDKDLVHGNVCTKNLLLAREGIDSECGPFIKLSDPGIPITVLS.......RQECIERIPW.IAPECVEDSKNLSVAADKWSFGTTLWEIC-20aa-
Domain 2   DYLGSRQYVHRDLAARNVLVESE.........VKIGDFGLTKAIETDKEYYTVKDDRDSPCFW.YAPECLMQSKF.YIASDVWSFGVTLHELL-38aa-
CDC2-H     VFCHSRRVLHRDLKPQNLLIDDKG........TIKLADGGLARAFGIPIRVYTHE...VVT.LMYRSPEVLLGSARYSTPVDIWSIGTIFAELA-50aa- XI
Domain 1   SRCRPVTPSCKELADLMTRCMNYDPNQRPF
Domain 2   LPCPPNCPDEVYQ..LMRKCWEFQPSNRTS
CDC2-H     LASHHVKNLDENGLDLLSKMLIYDPAKRIS
```

FIG. 5

```
                    Ia                                    IIa            IIIa  70
VFHKIRNEDL IFNESLGQGT FTKIFKGVRR EVGDYGQLHE TE...VLLKV LDKAHRNYSE SFFEAASMMS   MJAK2
 *$*    **  $ * ** **  * *$ *    $ *    *   *$*** ** **  *  ********
SFDRILKKDL VQGEHLGRGT RTHIYSGTLM DYKDDEGTSE EKKIKVILKV LDPSHRDISL AFFEAASMMR   HJAK1

IVa                   Va                                          140
QLSHKHLVLN YGVCVCGEEN ILVQEFVKFG SLDTYLKKNK NSINILWKLG VAKQLAWAMH FLEEKSLIHG   MJAK2
*$****$*   *****      ** * * *** *    ** $    $     **  ****** *  $**$* *$**
QVSHKHIVYL YGVCVRDVEN IMVEEFVEGG PLDLFMHRKS DVLTTPWKFK VAKQLASALS YLEDKDLVHG   HJAK1

VIa               VIIa                             VIIIa             210
NVCAKNILLI REEDRRTGNP PFIKLSDPGI SITVLPKDIS SCCFQVLQER IPWVPPECIE NPKNLTLATD   MJAK2
*** **$**  **           ********* **** $        *  ** ***$ ***$*  ***$$* *
NVCTKNLLLA REGIDSECGP .FIKLSDPGI PITVLSR... ....QECIER IPWIAPECVE DSKNLSVAAD   HJAK1

IXa                            Xa                          XIa        280
KWSFGTTLWE ICSGGDKPLS ALDSQRKLQF YEDKHQLPAP KWTELANLIN NCMDYEPDFR PAFRAVIRDL   MJAK2
**********  **  *$ **      * * ** $    *    *** *    ** *$*  * *  ***$ **$
KWSFGTTLWE ICYNGEIPLK DKTLIEKERF YESRCRPVTP SCKELADLMT RCMNYDPNQR PFFRAIMRDI   HJAK1

I              350
NSLFTPDYEL LTENDMLPNM RIGALGFSGA FEDRDPTQFE ERHLKFLQQL GKGNFGSVEM CRYDPLQDNT   MJAK2
 * *       $ $$   *                  *** *  * **  $ *  * ** **   ***** ***
NKLEEQNPDI VSRKKNQPTE V......... ....DPTHFT KRFLKRIRDL GEGHFGKVEL CRYDPE.DNT   HJAK1

II           III          IV                                V        420
GEVVAVKKLQ H.STEEHLRD FEREIEILKS LQHDNIVKYK GVCYSAGRRN LRLIMEYLPY GSLRDYLQKH   MJAK2
** **** *     *  *$ *   $*****$  * *$****** *$*    *    $$****$**  ***$$** *
GEQVAVKSLK PESGGNHIAD LKKEIEILRN LYHENIVKYK GICTEDGGNG IKLIMEFLPS GSLKEYLPKN   HJAK1

VI          VII                    490
KERIDHKKLL QYTSQICKGM EYLGTKRYIH RDLATRNILV ENENRVKIGD FGLTKVLPQD KEYYKVKEPG   MJAK2
 *  $*  *  *  *   ****** $***$$ *$*  **** **$** * *   *****  *****$$  *  **** **$
KNKINLKQQL KYAVQICKGM DYLGSRQYVH RDLAARNVLV ESEHQVKIGD FGLTKAIETD KEYYTVKDDR   HJAK1

VIII           IX                                                   560
ESPIFWYAPE SLTESKFSVA SDVWSFGVVL YELFTYIEKS KSPPVEFMRM IGNDKQGQMI VFHLIELLKS   MJAK2
$**$******  * *** $*  ********  * ** ** $    ** $ * $*  **     ***  * *$   **
DSPVFWYAPE CLMQSKFYIA SDVWSFGVTL HELLTYCDSD SSPMALFLKM IGPTH.GQMT VTRLVNTLKE   HJAK1

X              XI         600
NGRLPRPEGC PDEIYVIMTE CWNNNVSQRP SFRDLSFGWI KSGTV              MJAK2
 *** *  *  ***$* $*   **   *  ** * *
GKRLPCPPNC PDEVYQLMRK CWEFQPSNRT SFQNLIEGFE ALLK               HJAK1
```

FIG. 8A

```
CTG CTT GAT GAC TTT GTC ATG TCT TAC CTT TCC CCT CAG TGG CGG        45
Leu Leu Asp Asp Phe Val Met Ser Tyr Leu Ser Pro Gln Trp Arg
 1               5                  10                  15

CAT GAT TTT GTT CAC GGA TGG ATA AAA GTA CCT GTG ACT CAT GAA        90
His Asp Phe Val His Gly Trp Ile Lys Val Pro Val Thr His Glu
                20                  25                  30

ACT CAG GAA GAG TGT CTT GGG ATG GCG GTG TTA GAC ATG ATG AGA       135
Thr Gln Glu Glu Cys Leu Gly Met Ala Val Leu Asp Met Met Arg
                35                  40                  45

ATA GCT AAG GAG AAA GAC CAG ACT CCA CTG GCT GTC TAT AAC TCT       180
Ile Ala Lys Glu Lys Asp Gln Thr Pro Leu Ala Val Tyr Asn Ser
                50                  55                  60

GTC AGC TAC AAG ACA TTC TTA CCA AAG TGC GTT CGA GCG AAG ATC       225
Val Ser Tyr Lys Thr Phe Leu Pro Lys Cys Val Arg Ala Lys Ile
                65                  70                  75

CAA GAC TAT CAC ATT TTA ACC CGG AAG CGA ATC AGG TAC AGA TTT       270
Gln Asp Tyr His Ile Leu Thr Arg Lys Arg Ile Arg Tyr Arg Phe
                80                  85                  90

CGC AGA TTC ATT CAG CAA TTC AGT CAA TGT AAA GCC ACT GCC AGG       315
Arg Arg Phe Ile Gln Gln Phe Ser Gln Cys Lys Ala Thr Ala Arg
                95                 100                 105

AAC CTA AAA CTT AAG TAT CTT ATA AAC CTG GAA ACC CTG CAG TCT       360
Asn Leu Lys Leu Lys Tyr Leu Ile Asn Leu Glu Thr Leu Gln Ser
               110                 115                 120

GCC TTC TAC ACA GAA CAG TTT GAA GTA AAA GAA TCT GCA AGA GGT       405
Ala Phe Tyr Thr Glu Gln Phe Glu Val Lys Glu Ser Ala Arg Gly
               125                 130                 135

CCT TCA GGT GAG GAG ATT TTT GCA ACC ATT ATA ATA ACT GGA AAC       450
Pro Ser Gly Glu Glu Ile Phe Ala Thr Ile Ile Ile Thr Gly Asn
               140                 145                 150

GGT GGA ATT CAG TGG TCA AGA GGG AAA CAT AAG GAA AGT GAG ACA       495
Gly Gly Ile Gln Trp Ser Arg Gly Lys His Lys Glu Ser Glu Thr
               155                 160                 165
```

FIG. 8B

| | |
|---|---|
| CTG ACA GAA CAG GAC GTA CAG TTA TAT TGT GAT TTC CCT GAT ATT<br>Leu Thr Glu Gln Asp Val Gln Leu Tyr Cys Asp Phe Pro Asp Ile<br>170                       175                   180 | 540 |
| ATT GAT GTC AGT ATT AAG CAA GCA AAT CAG GAA TGC TCA ACT GAA<br>Ile Asp Val Ser Ile Lys Gln Ala Asn Gln Glu Cys Ser Thr Glu<br>185                       190                   195 | 585 |
| AGT AGA GTT GTG ACC GTC CAC AAG CAG GAC GGG AAG GTC TTG GAA<br>Ser Arg Val Val Thr Val His Lys Gln Asp Gly Lys Val Leu Glu<br>200                       205                   210 | 630 |
| ATA GAA CTT AGC TCA TTA AAA GAA GCC TTG TCA TTC GTG TCA TTA<br>Ile Glu Leu Ser Ser Leu Lys Glu Ala Leu Ser Phe Val Ser Leu<br>215                       220                   225 | 675 |
| ATT GAC GGG TAT TAC AGA CTA ACT GCG GAT GCA CAC CAT TAC CTC<br>Ile Asp Gly Tyr Tyr Arg Leu Thr Ala Asp Ala His His Tyr Leu<br>230                       235                   240 | 720 |
| TGC AAA GAG GTG GCT CCC CCA GCT GTG TTC GAG AAC ATA CAC AGC<br>Cys Lys Glu Val Ala Pro Pro Ala Val Phe Glu Asn Ile His Ser<br>245                       250                   255 | 765 |
| AAC TGC CAC GGC CCA ATT TCA ATG GAT TTT GCC ATC AGC AAA CTA<br>Asn Cys His Gly Pro Ile Ser Met Asp Phe Ala Ile Ser Lys Leu<br>260                       265                   270 | 810 |
| AAG AAG GCA GGA AAC CAG ACT GGA CTG TAT GTA CTT CGA TGT AGC<br>Lys Lys Ala Gly Asn Gln Thr Gly Leu Tyr Val Leu Arg Cys Ser<br>275                       280                   285 | 855 |
| CCT AAG GAC TTC AAC AAA TAC TTC CTG ACC TTT GCC GTT GAG CGA<br>Pro Lys Asp Phe Asn Lys Tyr Phe Leu Thr Phe Ala Val Glu Arg<br>290                       295                   300 | 900 |
| GAA AAT GTT ATT GAA TAT AAA CAC TGT TTG ATT ACA AAG AAT GAG<br>Glu Asn Val Ile Glu Tyr Lys His Cys Leu Ile Thr Lys Asn Glu<br>305                       310                   315 | 945 |

FIG. 8C

```
AAT GGA GAG TAC AAC CTC AGT GGG ACT AAG AGG AAC TTC AGT AGT    990
Asn Gly Glu Tyr Asn Leu Ser Gly Thr Lys Arg Asn Phe Ser Ser
                320             325             330

CTT AAG GAC CTT TTG AAT TGC TAC CAG ATG GAA ACT GTG CGC TCA   1035
Leu Lys Asp Leu Leu Asn Cys Tyr Gln Met Glu Thr Val Arg Ser
                335             340             345

GAC AGT ATC ATC TTC CAG TTC ACC AAA TGC TGT CCT CCA AAG CCG   1080
Asp Ser Ile Ile Phe Gln Phe Thr Lys Cys Cys Pro Pro Lys Pro
                350             355             360

AAA GAT AAA TCA AAC CTT CTT GTC TTC AGA ACA AAT GGT GTT TCT   1125
Lys Asp Lys Ser Asn Leu Leu Val Phe Arg Thr Asn Gly Val Ser
                365             370             375

GAT GTT CAG CTC TCA CCA ACA TTA CAG AGG CAT AAT AAT GTG AAT   1170
Asp Val Gln Leu Ser Pro Thr Leu Gln Arg His Asn Asn Val Asn
                380             385             390

CAA ATG GTG TTT CAC AAA ATC AGG AAT GAA GAT TTG ATA TTT AAT   1215
Gln Met Val Phe His Lys Ile Arg Asn Glu Asp Leu Ile Phe Asn
                395             400             405
                      Iₐ
GAA AGC CTT GGC CAA GGC ACT TTT ACA AAA ATA TTT AAA GGT GTA   1260
Glu Ser Leu Gly Gln Gly Thr Phe Thr Lys Ile Phe Lys Gly Val
                410             415             420

AGA AGA GAA GTT GGA GAT TAT GGT CAG CTG CAC GAA ACC GAA GTT   1305
Arg Arg Glu Val Gly Asp Tyr Gly Gln Leu His Glu Thr Glu Val
                425             430             435
 IIₐ
CTT TTG AAA GTC CTA GAT AAA GCA CAT AGA AAC TAT TCA GAG TCT   1350
Leu Leu Lys Val Leu Asp Lys Ala His Arg Asn Tyr Ser Glu Ser
                440             445             450
  IIIₐ
TTC TTT GAA GCA GCA AGC ATG ATG AGT CAG CTT TCT CAC AAG CAT   1395
Phe Phe Glu Ala Ala Ser Met Met Ser Gln Leu Ser His Lys His
                455             460             465
```

FIG. 8D

```
IVa
TTG GTT TTG AAT TAT GGA GTA TGT GTC TGT GGA GAG GAG AAC ATT      1440
Leu Val Leu Asn Tyr Gly Val Cys Val Cys Gly Glu Glu Asn Ile
            470             475                 480

TTG GTT CAA GAG TTT GTA AAA TTT GGA TCA CTG GAT ACA TAC CTG      1485
Leu Val Gln Glu Phe Val Lys Phe Gly Ser Leu Asp Thr Tyr Leu
            485             490                 495

AAG AAG AAC AAA AAT TCT ATA AAT ATA TTA TGG AAA CTT GGA GTG      1530
Lys Lys Asn Lys Asn Ser Ile Asn Ile Leu Trp Lys Leu Gly Val
            500             505                 510

GCG AAG CAG TTG GCA TGG GCC ATG CAC TTC CTC GAA GAA AAA TCC      1575
Ala Lys Gln Leu Ala Trp Ala Met His Phe Leu Glu Glu Lys Ser
            515             520                 525
                        VIa
CTT ATT CAT GGG AAT GTG TGT GCT AAA AAT ATC CTG CTT ATC AGA      1620
Leu Ile His Gly Asn Val Cys Ala Lys Asn Ile Leu Leu Ile Arg
            530             535                 540

GAA GAA GAC AGG AGA ACG GGG AAC CCA CCT TTC ATC AAA CTT AGT      1665
Glu Glu Asp Arg Arg Thr Gly Asn Pro Pro Phe Ile Lys Leu Ser
            545             550                 555
  VIIa
GAT CCT GGC ATT AGC ATT ACA GTT CTA CCG AAG GAC ATT TCT TCC      1710
Asp Pro Gly Ile Ser Ile Thr Val Leu Pro Lys Asp Ile Ser Ser
            560             565                 570
                                            VIIIa
TGT TGT TTC CAA GTT CTT CAG GAG AGA ATA CCA TGG GTA CCA CCT      1755
Cys Cys Phe Gln Val Leu Gln Glu Arg Ile Pro Trp Val Pro Pro
            575             580                 585

GAG TGC ATT GAG AAT CCT AAA AAT CTA ACT CTG GCA ACA GAC AAG      1800
Glu Cys Ile Glu Asn Pro Lys Asn Leu Thr Leu Ala Thr Asp Lys
            590             595                 600
        IXa
TGG AGC TTC GGG ACC ACT CTG TGG GAG ATC TGC AGT GGA GGA GAT      1845
Trp Ser Phe Gly Thr Thr Leu Trp Glu Ile Cys Ser Gly Gly Asp
            605             610                 615
```

FIG. 8E

```
AAG CCC CTG AGT GCT CTG GAT TCT CAA AGA AAG CTG CAG TTC TAT        1890
Lys Pro Leu Ser Ala Leu Asp Ser Gln Arg Lys Leu Gln Phe Tyr
                620                 625                 630
                 Xa
GAA GAT AAG CAT CAG CTT CCT GCA CCC AAG TGG ACA GAG TTG GCA        1935
Glu Asp Lys His Gln Leu Pro Ala Pro Lys Trp Thr Glu Leu Ala
                635                 640                 645
                                     XIa
AAC CTT ATA AAT AAT TGC ATG GAC TAT GAG CCA GAT TTC AGG CCT        1980
Asn Leu Ile Asn Asn Cys Met Asp Tyr Glu Pro Asp Phe Arg Pro
                650                 655                 660
GCT TTC AGA GCT GTC ATC CGT GAT CTT AAC AGC CTG TTT ACT CCA        2025
Ala Phe Arg Ala Val Ile Arg Asp Leu Asn Ser Leu Phe Thr Pro
                665                 670                 675
GAT TAT GAA CTA CTA ACA GAA AAT GAC ATG CTA CCA AAC ATG AGA        2070
Asp Tyr Glu Leu Leu Thr Glu Asn Asp Met Leu Pro Asn Met Arg
                680                 685                 690
ATA GGT GCC CTA GGG TTT TCT GGT GCT TTT GAA GAC AGG GAC CCT        2115
Ile Gly Ala Leu Gly Phe Ser Gly Ala Phe Glu Asp Arg Asp Pro
                695                 700                 705
ACA CAG TTT GAA GAG AGA CAC TTG AAG TTT CTA CAG CAG CTT GGC        2160
Thr Gln Phe Glu Glu Arg His Leu Lys Phe Leu Gln Gln Leu Gly
                710                 715                 720
     I
AAA GGT AAC TTC GGG AGT GTG GAG ATG TGC CGC TAT GAC CCG CTG        2205
Lys Gly Asn Phe Gly Ser Val Glu Met Cys Arg Tyr Asp Pro Leu
                725                 730                 735
                                     II
CAG GAC AAC ACT GGC GAG GTG GTC GCT GTG AAG AAA CTC CAG CAC        2250
Gln Asp Asn Thr Gly Glu Val Val Ala Val Lys Lys Leu Gln His
                740                 745                 750
                                                     III
AGC ACT GAA GAG CAC CTC CGA GAC TTT GAG AGG GAG ATC GAG ATC        2295
Ser Thr Glu Glu His Leu Arg Asp Phe Glu Arg Glu Ile Glu Ile
                755                 760                 765
                                IV
CTG AAA TCC TTG CAG CAT GAC AAC ATC GTC AAG TAC AAG GGA GTG        2340
Leu Lys Ser Leu Gln His Asp Asn Ile Val Lys Tyr Lys Gly Val
                770                 775                 780
```

FIG. 8F

```
TGC TAC AGT GCG GGT CGG CGC AAC CTA AGA TTA ATT ATG GAA TAT         2385
Cys Tyr Ser Ala Gly Arg Arg Asn Leu Arg Leu Ile Met Glu Tyr
                785                 790                 795
         V
TTA CCA TAT GGA AGT TTA CGA GAC TAT CTC CAA AAA CAT AAA GAA         2430
Leu Pro Tyr Gly Ser Leu Arg Asp Tyr Leu Gln Lys His Lys Glu
                800                 805                 810

CGG ATA GAT CAC AAA AAA CTT CTT CAA TAC ACA TCT CAG ATA TGC         2475
Arg Ile Asp His Lys Lys Leu Leu Gln Tyr Thr Ser Gln Ile Cys
                815                 820                 825

AAG GGC ATG GAA TAT CTT GGT ACA AAA AGG TAT ATC CAC AGG GAC         2520
Lys Gly Met Glu Tyr Leu Gly Thr Lys Arg Tyr Ile His Arg Asp
                830                 835                 840
VI
CTG GCA ACA AGG AAC ATA TTG GTG GAA AAT GAG AAC AGG GTT AAA         2565
Leu Ala Thr Arg Asn Ile Leu Val Glu Asn Glu Asn Arg Val Lys
                845                 850                 855
         VII
ATA GGA GAC TTC GGA TTA ACC AAA GTC TTG CCG CAG GAC AAA GAA         2610
Ile Gly Asp Phe Gly Leu Thr Lys Val Leu Pro Gln Asp Lys Glu
                860                 865                 870

TAC TAC AAA GTA AAG GAG CCA GGG GAA AGC CCC ATA TTC TGG TAC         2655
Tyr Tyr Lys Val Lys Glu Pro Gly Glu Ser Pro Ile Phe Trp Tyr
                875                 880                 885
VIII
GCA CCT GAA TCC TTG ACG GAG AGC AAG TTT TCT GTG GCC TCA GAT         2700
Ala Pro Glu Ser Leu Thr Glu Ser Lys Phe Ser Val Ala Ser Asp
                890                 895                 900
         IX
GTG TGG AGC TTT GGA GTG GTT CTA TAC GAA CTT TTC ACA TAC ATC         2745
Val Trp Ser Phe Gly Val Val Leu Tyr Glu Leu Phe Thr Tyr Ile
                905                 910                 915

GAG AAG AGT AAA AGT CCA CCC GTG GAA TTT ATG CGA ATG ATT GGC         2790
Glu Lys Ser Lys Ser Pro Pro Val Glu Phe Met Arg Met Ile Gly
                920                 925                 930

AAT GAT AAA CAA GGG CAA ATG ATT GTG TTC CAT TTG ATA GAG CTA         2835
Asn Asp Lys Gln Gly Gln Met Ile Val Phe His Leu Ile Glu Leu
                935                 940                 945
```

FIG. 8G

```
                            X
CTG AAG AGC AAC GGA AGA TTG CCA AGG CCA GAA GGA TGC CCA GAT          2880
Leu Lys Ser Asn Gly Arg Leu Pro Arg Pro Glu Gly Cys Pro Asp
                    950             955             960

GAG ATT TAT GTG ATC ATG ACA GAG TGC TGG AAC AAC AAT GTG AGC          2925
Glu Ile Tyr Val Ile Met Thr Glu Cys Trp Asn Asn Asn Val Ser
                    965             970             975
            XI
CAG CGT CCC TCC TTC AGG GAC CTT TCC TTC GGG TGG ATC AAA TCC          2970
Gln Arg Pro Ser Phe Arg Asp Leu Ser Phe Gly Trp Ile Lys Ser
                    980             985             990

GGG ACA GTA TAGCTGCGTG AAAGAGATGG CCTTACTCAG AGACCAAGCA              3019
Gly Thr Val

GACTTCCAGA ACCAGAACAA AGCTCTGTAG CCTTGTGTCT ACACATCCTT              3069

ATCATGACGC TAGCTAGGCA GAAAGAAAAC TGTGACGCCG TCTGCTCAAA              3119

AGCTTTGGAA AACGCCGTGC AGGTTTGTTT CATCACCATC TGTAAAAACC              3169

ACTGCTCAAG TCTGGCAGCA TGCTTGTGGG CTGATGCATG GAGCTCACCA              3219

CAGAGTCTCT GCATCTCCTC TGACAGAAGA AGAAAAATAG ACAATTTTCA              3269

ACTCACTTTT TTGAGAAATG GAAAAAAATT ATAATGTAAA TTTTTCAGTG              3319

TAGGAAATAC ACAGAACATA CATGTACAGT TTTTACCACG TGGAGTGTAT              3369

AATACTTTGG CCTCTTGTGT GATTTACATG AGGGCTGATG TTTGTTAATG              3419

TTTTCTAATT TTTCCATAGG TGATCTATAA TAACTTCATG ATACAAATTA              3469

AAATGCTCAG AAAATTAAAA AAAAAA                                         3495
```

FIG. 11A

```
         1           11          21          31          41          51          61          71          81          91
J1  MQYLNIKEDCNAMAFCAKMRSSKKTEVNLEAPEPGVEVIFYLSDREPLRLGSGEYTAELCIRAAQACRISPLCHNLFALYDENTKLWYAPNRTITVDDK
J2                                                                  ....AEEVCIHIAHKVGITPPCFNLFALFDAQAQVWLPPNHILEIPRD
T2  MPLRHWGMARGSKPVGDGAQPMAAMGGLKVLLLHWAGPGGGEPWTFSESSLI                 AEE--CI-----------P-C-NLFAL-------W--PN--------

101         111         121         131         141         151         161         171         181         191
J1  MSLRLHYRMRFYFTNWHGTDNDNEQSVWRHSPKKQKNGYEKKKIPDATPLLDASSLEYLFAQGQYDLVKCLAPIRDPK.TEQDGHDIENECLGMAVLAISHY
J2                                              LLDDFVMSYLSPQWRHDFVHGWIKVPVTHETQEE.......CLGMAVLDMMRI
T2  ASLMLYFRIRFYFRNWHGMNPREPAGYRCGPPGTEASSDQTAQGMQ..LLDPASFEYLFEQGKHEFENDVASLWELS.TEEEIHHFKNESLGMAFLHLCHL
   -SL-L-R-RFYF-NWHG---N--E-----R--P---------------LLD---S-EYLF-QG-HDFV--A----TEEE--H----NECLGMAVL---H--
                                                  JH6→

201         211         221         231         241         251         261         271         281         291
J1  AMKKMQLPELPKDISYKRYIPETLNKSIRQRNLLTRMRINNVFKDFLKEFNKTICDSSVSTHDLKVKYLATLETLTKHYGAEIFETSMLLISSENEMN
J2  AKEKDQTPLAVYNSVSYKTFLPKCVRAKIQDYHILTRKRIRYRFRRFIQQFSQCKATARN.....LKLKYLINLETLQSAFYTEQFEVKESARGPSGEEI
T2  ALRHGIPLEEVAKKTSFKDCIPRSFRRHIRQHSALTRLRLRNVFRRFLRDFQPGRLSQQM.   .VMVKYLATLERLAPRFGTERVPVCHLRLLAQAEGE
    A----K---L-EV-K---SYK----IP---R--IRQ----LTR-RIRNVFRRFL--F-------LKVKYLATLETL----FGTE-FEV--L-----E---
                                                                                                ←JH6

301         311         321         331         341         351         361         371         381         391
J1  WFHSNDGGNVLYY..........EVMVTGNLGIQWRHKPNVVSVEKEKNKLKRKKLENKDKKDEEKNK......IREEWNNFSFFPEITHIVIKESV
J2  FAT............IIITGNGGIQWSRGKHKESETLTEQDLQLYCDFP.........DIIDVSIKQANQECSTESRI
T2  PSYIRDSGVAPTDPGPESAAGPPTHEVLVTGTGGIQWPVEEEVNKEEGSSGSSARNPQASLFGKKAKAHKAFGQPADRPREPLWAYFCDITHVVLKEHC
    ------D-G-----------EV-VTGNGGIQW-----------VS-E----L-----K-----------R----S-F--ITH-V-KE--
                    JH5→                          ←JH5

401         411         421         431         441         451         461         471         481         491
J1  VSINKQDNKKMELKLSSHEEALSFVSLVDGYFRLTADAHHYLCTDVAPPLIVHNIQNGCHGPIC-EYAI.NKLRQEGSEEGMYVLRWSCTDFDNILMTVT
J2  VTVHKQDGEVLEIELSSLKEALSFVSLIDGYYRLTADAHHYLCKEVAPPAVLENIHSNCHGPISMDFAI.SKLKKAGNQTGLYVLRCSPKDFNKYFLTFA
T2  VSIHRQDNKCLELSLPSRAAALSFESLVDGYFRLTADSSHYLCHEVAPPRLVMSIRDGIHGPLLEPFVQQAKLRP..LEDGLYLIHWSTSHPYRLLILTVA
    VSIHKQDNK-LEL-LSS--EALSFVSLVDGYFRLTADAHHYLC-EVAPP---V-NI--GCHGPI---FAI---KLR--G-E-GLYVLRWS--DF----LTVA
                                                                      JH4→                                          ←JH4
```

FIG. 11B

```
     501        511        521        531        541        551        561        571        581        591
J1   CFEKSEQVQGAQKQFKNFQIEVQKGRYSLHGSDRSFPSLGDLMSHLKKQILRTDNISFMLKRCCQPKPREISNLLVATKKAQEWQPVYPMSQLSFDRILK
J2   VER.....ENVIEYKHCLITKNENGEYNLSGTKRNFSSLKDLLNCYQMETVRSDSIIFQFTKCCPPKPKDKSNLLVFRTNGVSDVQLSPTLQRHNNVNQM
T2   QRSQAPDGMQSLRLRKF.PIEQQDGAFVLEGWGRSFPSVRELGAALQGCLLRAGDDCFSLRRCCLPQPGETSNLIIMRGARASPRTL.NLSQLSFHRVDQ
     -----------------K----IE-Q-G-Y-L-G--RSFPSL-DL----LQ---LR-D-I-F-L-RCC-PKP-E-SNLLV-R----S---L-P-SQLSF-R---
                      JH3→

601        611        621        631        641        651        661        671        681        691
J1   KD...LVQGEHLGRGTRTHIYSGTLMDYKDDEGTSEEKK.............IKVILLKVLDPSHRDISLAFFEAASMRQVSHKHIVLYGVC
J2   VFHKIRNEDLIFNESLGQGTFTKIFKGVRREVGDY.GQLHETE............VLLKVLDKAHRNYSESFFEAASMMSQLSHKHLVLNYGVC
T2   KE...ITQLSHLGQGTRTNVYEGRLRVEGS..GDPEEGKMDDEDPLVPGRDRGQELRVLKVLDPSHHDIALAFYETASLMSQVSHTHLAFVHGVC
     K----L-Q--EHLGQGTRT--IY-G-LR---GD--G--EE-K.........--V-LKVLDPSHRDISLAFFEAASMMSQVSHKHLV--YGVC
         JH2→

701        711        721        731        741        751        761        771        781        791
J1   VRDVENIMVEEFVEGGPLDLFMHRKSDVLTTPWKFKVAKQLASALSYLEDKDLVHGNVCTKNLLLAREGIDSECGPFIKLSDPGIPITVLSRQECIERIP
J2   VCGEENILVQEFVKFGSLDTYLKKNKNSINILWKLGVAKQLAWAMHFLEEKSLIHGNVCAKNILLIREEDRRTGNPFIKLSDPGISITVLPKDISSCCF.
T2   VRGPENSMVTEYVEHGPLDVWLRRERGHVPMAWKMVVAQQLASALSYLENKNLVHGNVCGRNILLARLGLAEGTSPFIKLSDPGCGLGALSREERVERIP
     VRG-ENIMV-EFVE-GPLD--L-R-------WK---VAKQLASALSYLE--K-LVHGNVC-KNILLAREG------PFIKLSDPGI--ITVLSR-E--ERIP 801        811        821        831        841        851        861        871        881        891
J1   ...WIAPECVED.SKNLSVAADKWSFGTTLWEICYNGEIPLKDKTLIEKERFYESRCRPVTPSCKELADLMTRCMNYDPNQRPFFRAIMRDINKLE
J2   ...QVLQERIPWVPPECIEN.PKNITLATDKWSFGTTLWEICSGGDKPLSALDSQRKLQFYEDKHQLPAPKWTELANLINNCMDYEPDFRPAFRAVIRDLNSLF
T2   WLAPECLPGGANSLSTAMDKWGFGATLLEICFDGEAPLQSRSPSEKEHFYQRQHRLPEPSCPQLATTSQCLTYEPTQRPSFATILRDLTAVQ
     W-APEC-E----NNLS-A--DKWSFGTTLWEIC---GE--PL------EKE-FYE--HRLP-PSC-ELA-L----CM-YEP-QRP-FRAI-RDLN-L--
```

FIG. 11C

FIG. 12

```
JAK1  QNGCHGPIC-EYAI.NKLRQEGSEEGMYVLRWSCT...DFDNILMTVTCFEKSEQVQGAQKQFKNFQIEVQKGRYSLHGSDRSFPSLGDLMSHLKKQILRTDNISFMLKRCCQPKP
JAK2  HSNCHGPISMDFAI.SKLKKAGNQTGLYVLRCSPK...DFNKYFLTFAVER....ENVIEYKHCLITKNENGEYNLSGTKRNFSSLKDLLNCYQMETVRSDSIIFQFTKCCPPKP
TYK2  RDGIHGPLLEPFVQQAKIRP..LEDGLYLIHWSTS...HPYRLILTVAQRSQAPDGMQSLRLRKF.PIEQQDGAFVLEGWGRSFPSVRELGAALQGCLLRAGDDCFSLRRCCLPQP
      -GCHGPI---FAI-KLR--G-E-GLYLRWS-----DF----LTVA------K---IE-Q-G-Y-L-G--RSFPSL-DL---LQ---LR-D-I-F-L-RCC--PKP

WYHGKI----A----L-------GSYLIRES---PGDFVLS-----------R--------V------G--R-F-SL-DL--YY---------L-EPV
GAP-N WYHGKLDRTIA.EERLR.QAGKSGSYLIRESDRRPGSFVLSFLSQT.NV......VNHFRI..IAMC.GDYY.IGG.RFFSSLSDLIGYYSHVSCLLKGE....KLLYPV
GAP-C WFHGKISKQEA.YNLLM.TVGQACSFLVRPSDNTPGDYSLYF.RTSENIQ..R.....FKI.CPTPN.NQFM.MGG.RYNSIGDIIDHYRKEQIVEGYY.....LKEPV
v-Crk WYWGRLSRGDA.VSLLQ..GQRHGTFLVRDSGSLPGDFVLSV.SESSRVS......HYIVNSLGPAGGRRAGGE.[18]..FDSLPSLLEFYKIHYLDTT.....TLIEPV
```

ANTIBODIES WHICH SPECIFICALLY BIND TO PROTEINS HAVING TYROSINE KINASE ACTIVITY, WHEREIN SAID PROTEINS HAVE MORE THAN ONE TYROSINE KINASE DOMAIN, AND NO SH2 DOMAINS

This application is a divisional of Ser. No. 08/064,067 filed Jun. 30, 1993.

The present invention relates generally to novel protein tyrosine kinase and to genetic sequences encoding same.

Protein tyrosine kinases (PTKs) are structurally well suited to a role intracellular signal transduction. Many growth factor receptors, for example, transduce the extracellular stimulus they receive through interaction with their cognate ligand via an intracellular tyrosine kinase domain. At least one of the non-receptor PTKs, namely LCK, is believed to mediate the transduction in T-cells of a signal from the interaction of a cell-surface protein (CD4) with a cross-linked anti-CD4 antibody.

The broader family of PTKs can be sub-divided on the basis of structural parameters of individual members. For example, the src family of PTKs now numbers 8 members (Marth et al., 1985; Nishizawa et al., 1986; Semba et al., 1986; Martinez et al., 1987; Sukegawa et al., 1987; Yamanishi et al., 1987; Hotzman et al., 1987; Dymecki et al., 1990), each with a characteristic complement of extra-catalytic domains, including an SH2, an SH3 domain and a variable ligand binding domain. It is clear that a process of gene duplication has taken place in this case, so that the evolutionarily successful thematic structure of this family can be employed in a variety of cellular contexts. Similar PTK structural sub-families exist based around the FGF receptor and the CSF-1 receptor (reviewed in Wilks, 1990).

However, one feature in common with the aforementioned PTKs is that each kinase bears a single highly related "catalytic" domain.

In accordance with the present invention a protein tyrosine kinase is provided which is distinct from those previously known. In particular, the protein tyrosine kinase of the present invention is unique since it possesses more than one protein kinase catalytic domain. Furthermore, the kinase does not bear an SH2 domain. The novel protein tyrosine kinase of the present invention represents a new subfamily or class of protein tyrosine kinase.

Accordingly, one aspect of the present invention is directed to an animal protein tyrosine kinase-like molecule comprising a polypeptide having multiple protein kinase catalytic domains but no SH2 domain.

Preferably, the polypeptide has two protein kinase catalytic domains.

Preferably, the animal is a mammal and is most preferably a human or a mouse.

Hereinafter, a protein having these characteristics will be referred to as a "JAK" (from JAnus Kinase: Janus, in Encyclopaedia Britannica (11th Ed) Vol XV pp 155–156). The present invention is specifically exemplified using JAK1 and JAK2 from humans and mice. This is done, however, with the understanding that the present invention extends to the whole family of JAKs from all animals and to mutants, derivatives, analogues and homologues thereof. The term "protein tyrosine kinase-like molecule" (abbreviated herein to "PTK-like molecule") is used throughout the specification and claims to emphasise that the present invention encompasses all members of the JAK family and to their mutants, derivatives, analogues and homologues.

In accordance with the present invention, there is provided a PTK-like molecule. Preferably the molecule is in biological pure or in substantially pure and/or synthetic form. The purity of the preparation is characterised by a sample comprising at least 70% by weight, preferably at least 80% by weight and most preferably at least 90% by weight PTK-like molecule. Alternatively, where the purity of the enzyme preparation is not critical, the present invention also encompasses an impure PTK-like molecule preparation but which possesses a substantial mount of JAK activity.

The present invention is directed to a naturally occurring PTK-like molecule, biologically pure or substantially pure as hereinbefore defined and to derivatives, functional analogues and homologues thereof. Such derivatives include polypeptides having single or multiple amino acid substitutions, deletions and/or additions relative to the naturally occurring sequence. These derivatives, functional analogues and homologues also encompass single or multiple substitutions, deletions and/or additions to any associated molecules such as carbohydrate, lipid and/or proteinacious moieties. Reference herein to "PTK-like molecules" includes all such derivatives, functional analogues and homologues. The present invention also extends to synthetic forms of the polypeptides which include recombinant molecules and molecules prepared by the stepwise addition of amino acids to groups of amino acids in defined order.

A range of derivatives and analogues of the PTK-like molecule are contemplated herein and include altering the molecule at its nucleotide sequence-encoding level, during its expression within a cell or in vitro or post-synthesis modification. Such derivatives and analogues include, but are not limited to, modifications to side chains, incorporation of unnatural amino acids during polypeptide synthesis and the use of crosslinkers and other methods which impose conformational constraints on the polypeptide or their anologues.

Examples of side chain modifications contemplated by the present invention include modifications of amino groups such as by reductive alkylation by reaction with an aldehyde followed by reduction with $NaBH_4$; amidination with methytacetimidate; acylation with acetic anhydride; carbamoylation of amino groups with cyanate; trinitrobenzylation of amino groups with 2, 4, 6, trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ringe of a histidine residue may be accomplished by alkylation with iodoacetic acid derivatives or N-carbethoxylation with diethylpyrocarbonate.

Examples of incorporating unnatural amino acids and derivatives during polypeptide synthesis include, but are not limited to, use of norleucine, 4-amino butyric acid, 4-amino-3-hydroxy-5-phenlpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, polypeptides could be conformationally constrained by, for example, incorporation of $C_\alpha$ and $N_\alpha$-methylamino acids, introduction of double bonds between $C_\alpha$ and $C_\beta$ atoms of amino acids and the formation of cyclic polypeptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof corresponding to regions of PTK-like molecules. Preferably, the PTK-like molecules will retain JAK activity. However, molecules carrying mutations in the catalytic domains rendering these inactive may be useful in, for example, titrating out activity and generation of antibodies such molecules are encompassed by the present invention.

The molecular weights of the PTK-like molecules of the present invention range from 100,000 to 200,000 daltons and preferably from 120,000 to 150,000 daltons.

In a most preferred embodiment, the present inventions provides JAK1 and JAK2. JAK1 is an approximately 1142 amino acid molecule with a molecular weight of about 132,000 daltons and a nucleotide sequence shown in FIG. 2. JAK2 is an approximately 1,100 amino acid molecule with a molecular weight of about 130,000 daltons and with a nucleotide sequence shown in FIG. 8.

The present invention is also directed to genetic sequences including DNA, cDNA and mRNA which encode the PTK-like molecules hereindescribed. Such genetic sequences include single or multiple nucleotide substitutions, deletions and/or additions relative the naturally occurring sequence and extend to sequences encoding the derivatives, functional analogues and homologues of the PTK-like molecules. The present invention also provides these genetic sequences in vector and expression vector systems either in vitro or in a biological system (i.e. eukaryotic or prokaryotic cells) transformed with such vectors or genetic sequences. In a most preferred embodiment the present invention provides cDNA encoding JAK1 and JAK2 as set forth in FIGS. 2 and 8, respectively. A range of mutants can be obtained using standard techniques such as an oligonucleotide mutagenesis and chemical mutagenesis, and all such mutants and derivatives are encompassed by the present invention.

The present invention also provides antibodies to a PTK-like molecule. Such antibodies may be monoclonal or polyclonal.

The PTK-like molecule of the present invention have varying utility such as in the phosphorylation of proteins, incorporation of labels and in the design of analogues, antagonists and agonists of JAKs.

Accordingly, another respect of the present invention contemplates a method for phosphorylating a protein comprising contacting said protein with a phosphorylating effective amount of a PTK-like molecule, said molecule comprising a polypeptide having multiple protein kinase catalytic domains but no SH2 domain for a time and under conditions sufficient for said first protein to be phosphorylated. Preferably, the polypeptide has two protein kinase catalytic domains and most preferably is JAK1 and/or JAK2 and/or their derivatives.

The present invention is further described by reference to the following non-limiting Figures and Examples.

In the Figures:

FIG. 1 is a photographic representation of a Northern analysis of murine and human JAK1.

A. 2 μg aliquots of poly(A)+ mRNA from murine tissues: lane 1, lung: lane 2, liver: lane 3, kidney: lane 4, intestine: lane 5, brain: lane 6, skeletal muscle: lane 7, spleen: lane 8, salivary gland: lane 9, placenta: lane 10, mammary gland, were fractionated on a 1.0% agarose/formaldehyde (Moran et al., 1988) gel and the RNA transferred onto a Genescreen plus (Dupont) membrane. The transferred RNA was hybridized with a 1.8 kb $^{32}$P-labelled murine JAK1 probe and the filter autoradiographed for 16 hr. at −70° C. with two intensifying screens. The relative mobilities of 28S rRNA (upper arrow) and 18S rRNA (lower arrow) are shown.

B. 2 μg aliquots of poly(A)+ mRNA from the human haemopoietic cell lines: lane 1, HL60 (myelo-monocytic); lane 2, U937 (monocytic): lane 3, LK63 (pre-B): lane 4, RAJI (B-cell): lane 5, CEM (T-cell): lane 6, K562 (erythroleukaemia) were fractionsted on a 1.0% agarose/formaldehyde (Moran et al., 1988) gel and the RNA transferred onto a Genescreen plus (Dupont) membrane. The transferred RNA was hybridized with a full-length $^{32}$P-labelled human JAK1 probe and the filter autoradiographed for 16 hr. at −70° C. with two intensifying screens. The relative mobilities of 28S rRNA (upper arrow) and 18S rRNA (lower arrow) are shown.

Figure 3B:
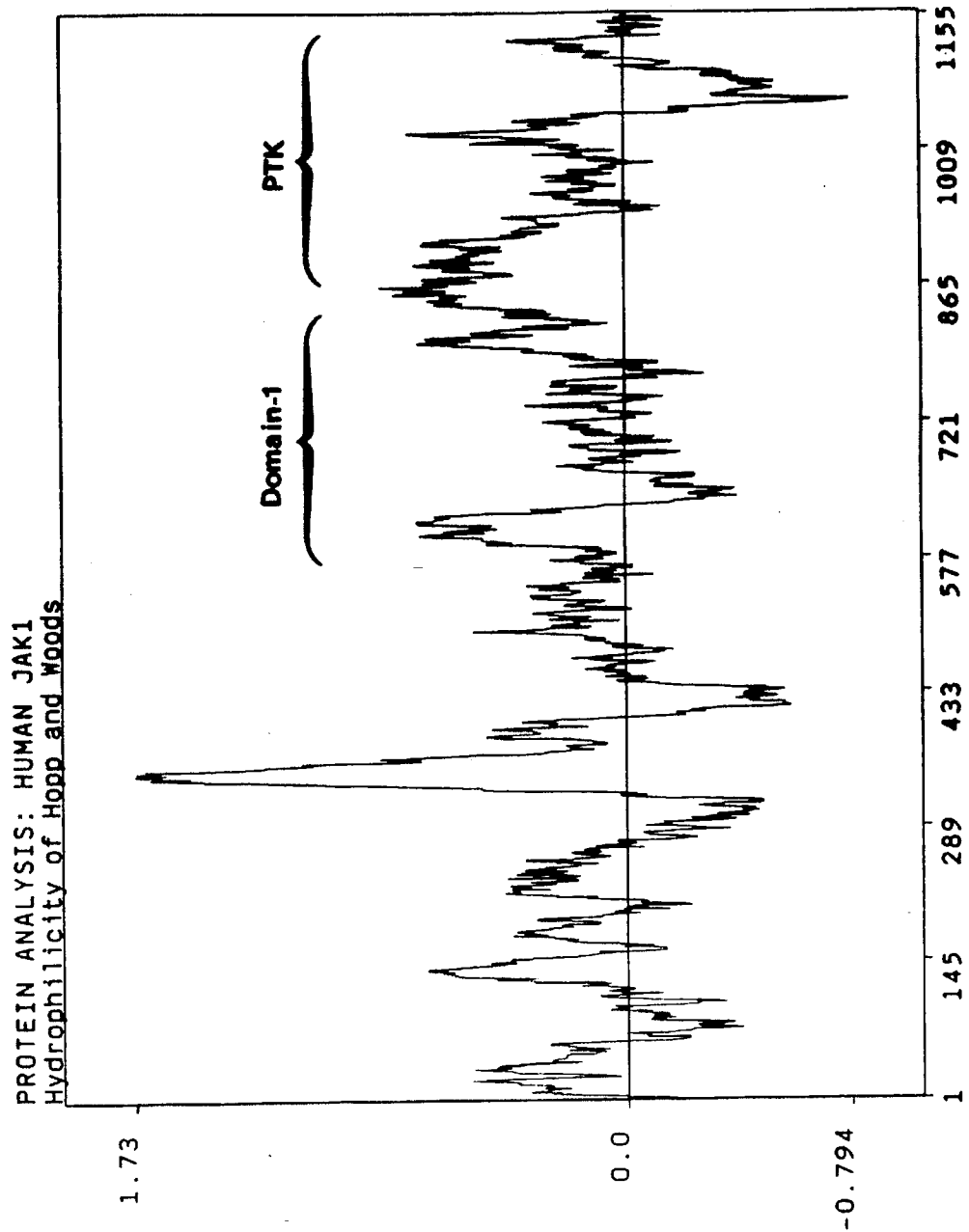

FIG. 2 is a representation showing nucleotide sequence and predicted amino acid sequence of human JAK1. The DNA sequence is numbered at the end of each line of sequence from the first nucleotide of the largest clone (pHJ7.3), the amino acid sequent (in one letter code) is numbered from the putative AUG and appears above the line to which it refers. The two kinase catalytic domains are boxed with arrows, and kinase consensus motifs are enumerated according to the nomenclature of Hanks et al (1988). The suffix a (e.g. IIa) denotes the kinase related motifs present in the first kinase-related domain (designated domain-1 in FIG. 3a) also numbered according to the same nomenclature. The tyrosine residue in an analogous position to the autophosphorylation site of a number of other protein tyrosine kinases is marked with an inverted triangle. (Sequence Id. 1)

FIG. 3 is a representation showing:

Panel A. Amino-acid sequence comparison of the two kinase-related domains of JAK1. The amino-acid sequences (expressed in one-letter amino acid code) of the two kinase-related domaim (domain-1 amino-acids 576–825; domain-2 (PTK-domain) amino-acids 868–1130) of JAK1 and the human threonine/serine-specific kinase CDC2 (24) (amino acids 9–272) are aligned in order to maximize identity. The kinase-related domains have been divided into three segments and the number of amino acid residues separating each segment appears at the end of each line. Motifs held in common between at least two of these domains are both bolded and boxed. Roman numerals above the alignment correspond to the conserved domain nomenclature devised by Hanks et al (1988).

Panel B. Hydropathy plot of the human JAK1 protein. The protein sequence of human JAK1 (including the 10 extra amino acids which precede the most likely initiation codon) were analysed by the hydrophilicity algorithm of Kyte and Doolittle (1982) using a span length of 25 amino acids. The relative locations of the two kinase related domains are marked as Domain-1 and PTK. The absence of a hydrophobic transmembrane domain is clearly seen, as can the presence of a highly hydrophilic region between amino acids 323 and 350.

Figure 4A:
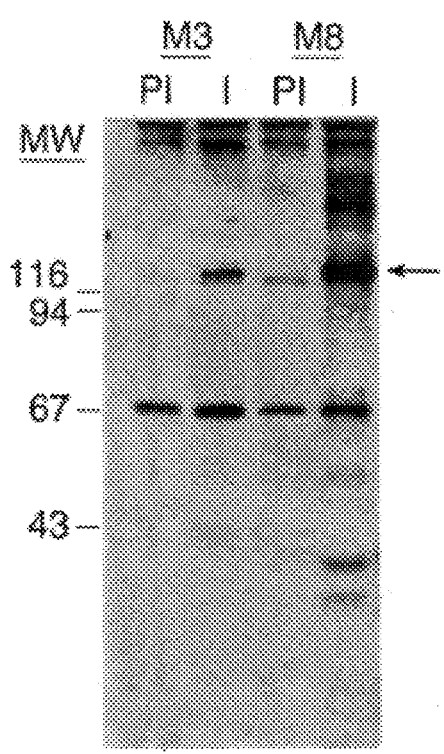
Figure 4B:
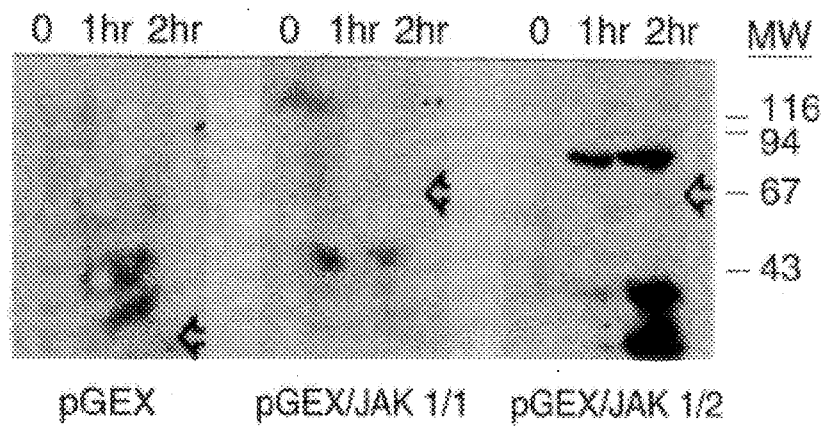
Figure 4C:
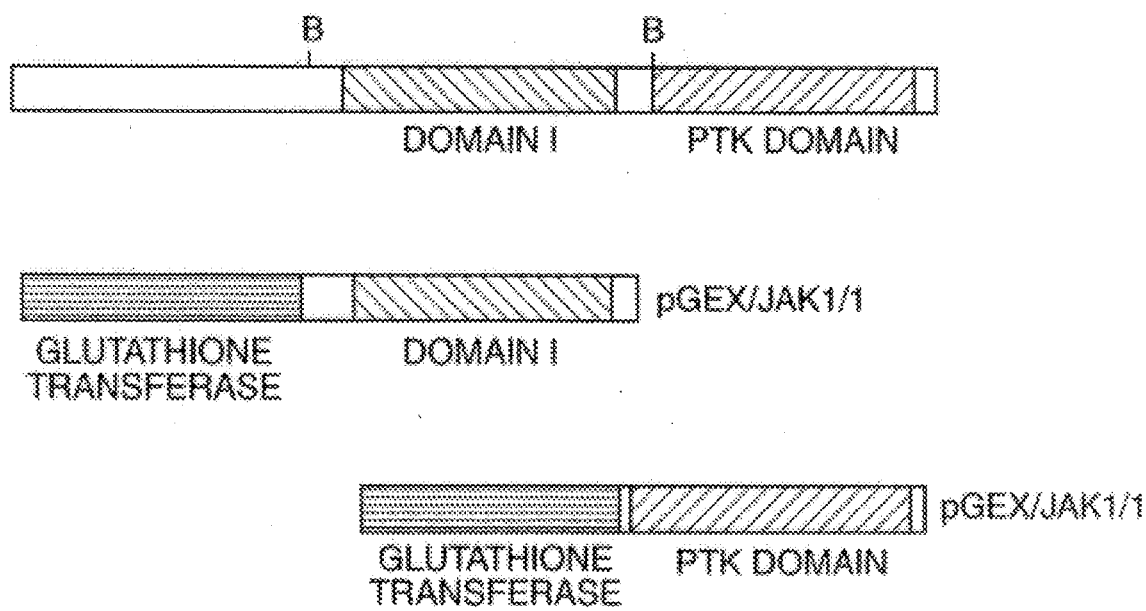

FIG. 4 is a representation of an analysis of the JAK1 protein.

Panel A. Cellular proteins of the murine mammary fibroblast cell line (17) were labelled with $^{35}$S-methionine (panel A) and immunoprecipitated with either pre-immune (PI) or immune (I) anti-JAK rabbit antiserum (raised in rabbit M8 against the pGEX/JAK1/1 fusion protein or the C-terminal peptide [M3]) and fractionated on a 9.5% SDS-PAGE gel (Laemmli, 1970). Both rabbit antisera specifically immunopreciptated an $^{35}$S-labelled protein of apparent molecular weight 130,000D.

Panel B. Demonstration of tyrosine kinase activity in JAK1 bacterial fusion proteins. JAK1 fusion proteins were generated using pGEX2 (Smith and Johnson, 1988). The entire domain-1 region was included in construct pGEX/JAK1/1. The PTK domain portion of the fusion protein extended to the BamHI site 15 nucleotides 5' of the first glycine codon of the GXGXXG motif of the ATP binding site. An empty vector control was also performed. The bacteria were induced by the addition of 1 mM IPTG as described by Smith and Johnson (1988) and two 1 ml aliquots of the bacteria were removed at 60 minutes and 120 minutes post-induction and lysed with SDS staple buffer. Western analysis of the samples was performed using anti-phosphoryrosine antisera (PY-20 [ICN]). The arrow heads mark the positions of the GEX-JAK fusion proteins, in each induction.

Panel C. Construction of the pGEX/JAK fusion proteins, The locations of the two kinase related domains of JAK1 are shown, and below, the structure of the fusion proteins with the glutathione S-transferase gene.

FIG. 5 is a representation of a sequence comparison between JAK1 and JAK2 kinase-related domains. The deduced amino acid sequence of murine JAK2 was compared to the human JAK1 amino acid sequence by application of an alignment programme of the Staden VAX-based suite of Sequence analysis programmes. Asterisks (*) denote identity, dollar signs (S) denote conservative substitutions. Sequences are numbered with respect to the JAK1 sequence. The extent of the domain-1 and PTK domains is shown by arrows above the amino acid sequence.

Figure 6:
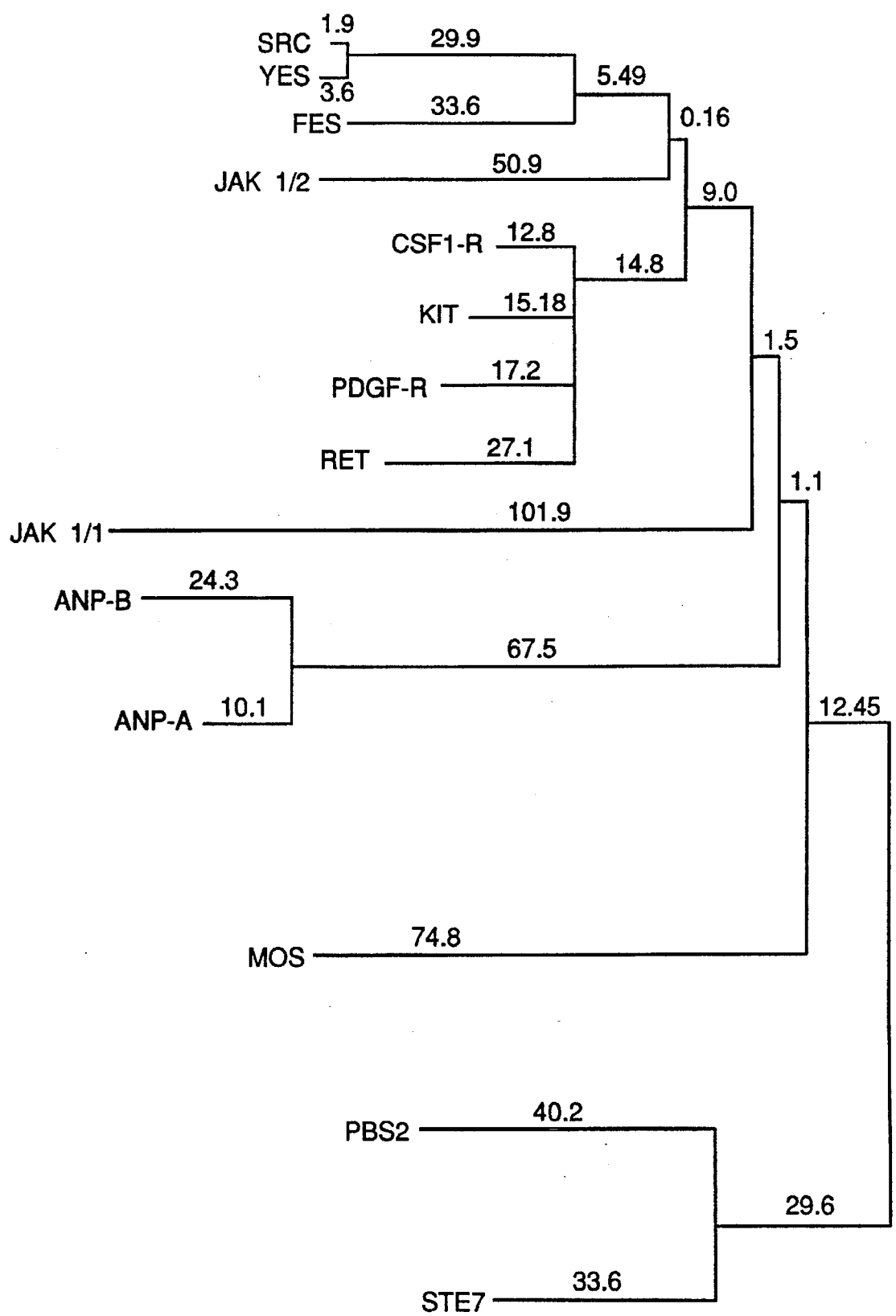

FIG. 6 is a graphical representation of a phylogenetic analysis of the two JAK1 Kinase-like domains. The tree building concept of Fitch and Margoliash (1967) as implemented by Feng and Doolittle (1987) and Hanks et al (1988) was used to generate a phylogenetic tree as described in Example 1. In each case the catalytic domain alone was used for comparison. The two kinase related domains of the JAK1 protein were compared independently. Branch order is a function of structural similarity, branch length a function of sequence identity. The abbreviations used are: SRC=c-src; YES=c-Yes; FES=c-fes; CSF1-R=Colony stimulating factor-1 receptor; KIT=c-kit; PDGF-R=Platelet derived growth factor receptor-A; RET=c-RET; ANP-A=Atrial nantueric peptide receptor-A; ANP-B=Atrial naturetic peptide receptor-B; MOS=c-mos; PBS2=polyxin B antibiotic resistance gene product; STE7=sterile mutant wild-type allele gene product; JAK1/1=Domain-1 of Human JAK1; JAK1/2=PTK domain or Human JAK1.

Figure 7B:
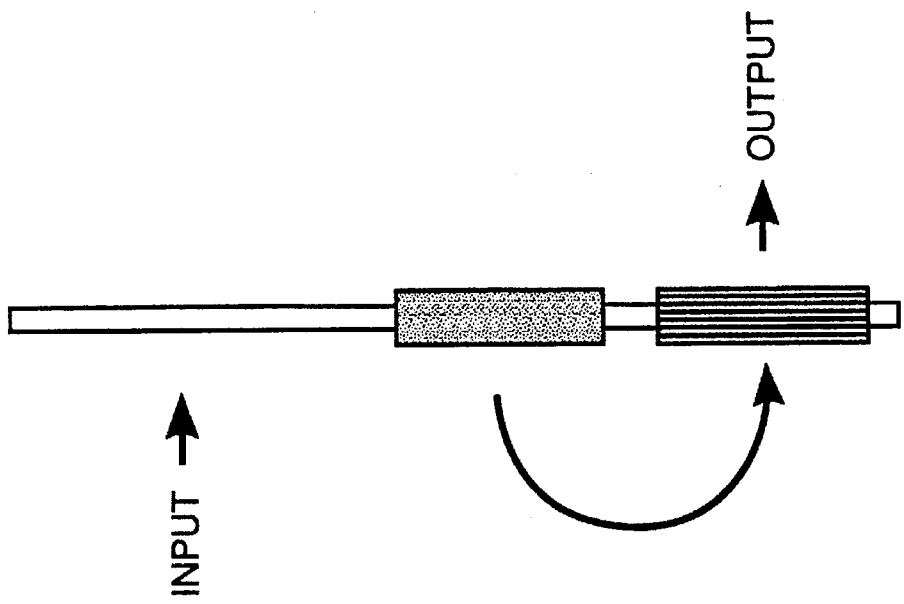
Figure 7A:
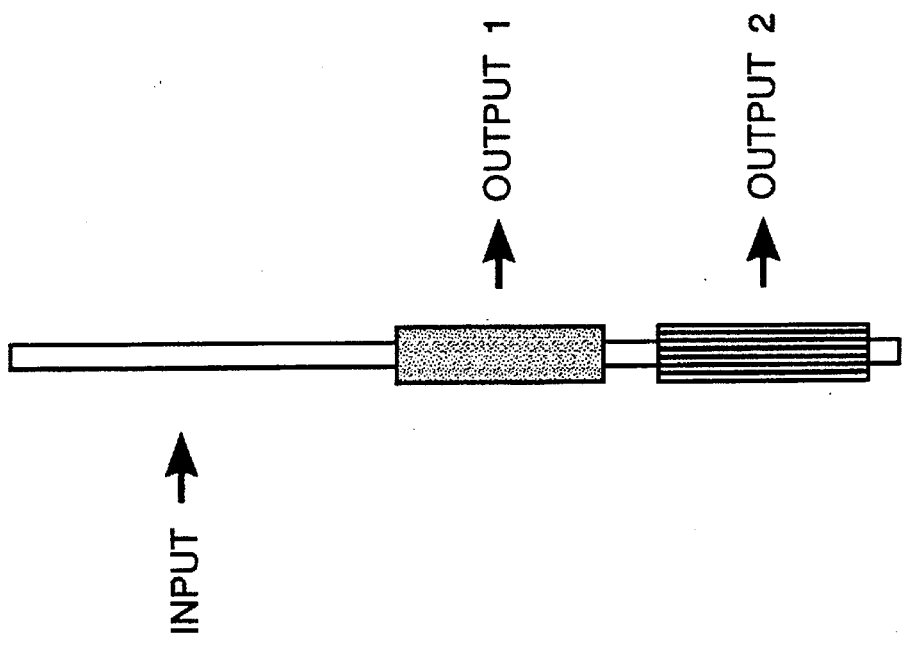

FIG. 7 is a diagramatic representation showing models for the role of members of the JAK family of PTKs in signal transduction. Two possible scenarios are considered based on an extrapolation of the current notions of the role of PTKs in signal transduction. In panel A the N-terminal domain of the JAK protein serves to sense a particular metabolic cue and convert this input into two distinct outputs. Presumably the output of the second PTK-related domain is tyrosine kinase activity; the activity of Domain-1 remains unknown. In panel B an alternative scenario is considered. In this case the function of Domain-1 is the regulation of the PTK domain. In this scenario the sole output of the JAK protein is the PTK activity.

FIG. 8 is a representation of a nucleotide sequence and predicted amino acid sequence of murine JAK2. The nucleotide sequence is numbered beneath each line of sequence, from the first nucleotide of the most 5' clone. The predicted amino acid sequence, in one letter code, is numbered at the end of each line of sequence. The two putative kinase domains are shown boxed with arrows, and the kinase consensus motifs are enumerated according to the nomenclature of Hanks et al (1988). The subscript a denotes the kinase-related motifs present in the first kinase-related domain, which are numbered according to the same nomenclature. (Sequence Id. 2)

Figure 9:
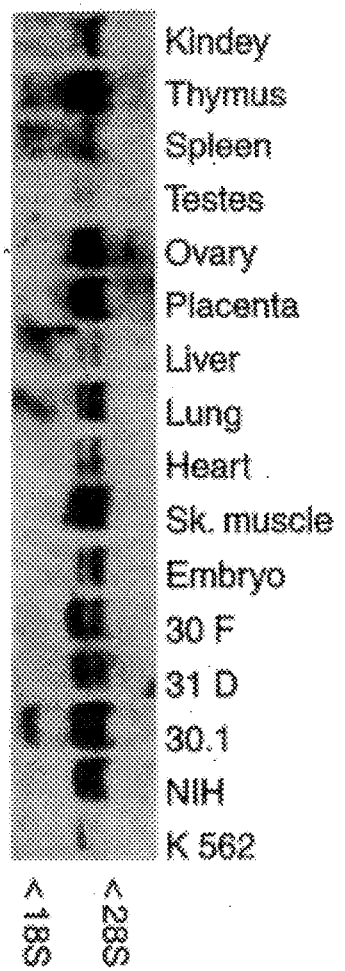

FIG. 9 is a photographic representation showing expression of JAK2 in murine tissues. Northern blot analysis of 5 μg of mRNA from each of the tissues shown on top of the figure and from various murine (30F: mammary fibroblasts; 31A: mammary epithelial cells; 30.1: factor independent subline of the hemopoietic cell line FDC.P1; NIH: fibroblasts) and human (K562: chronic myelogenous leukaemic cells) cell line. The blots were hybridized with a $^{32}$P-labelled 2.2 kb JAK2 probe and autoradiography was for 4 days. The relative mobilities of the 28S and the 18S rRNA are indicated.

Figure 10:
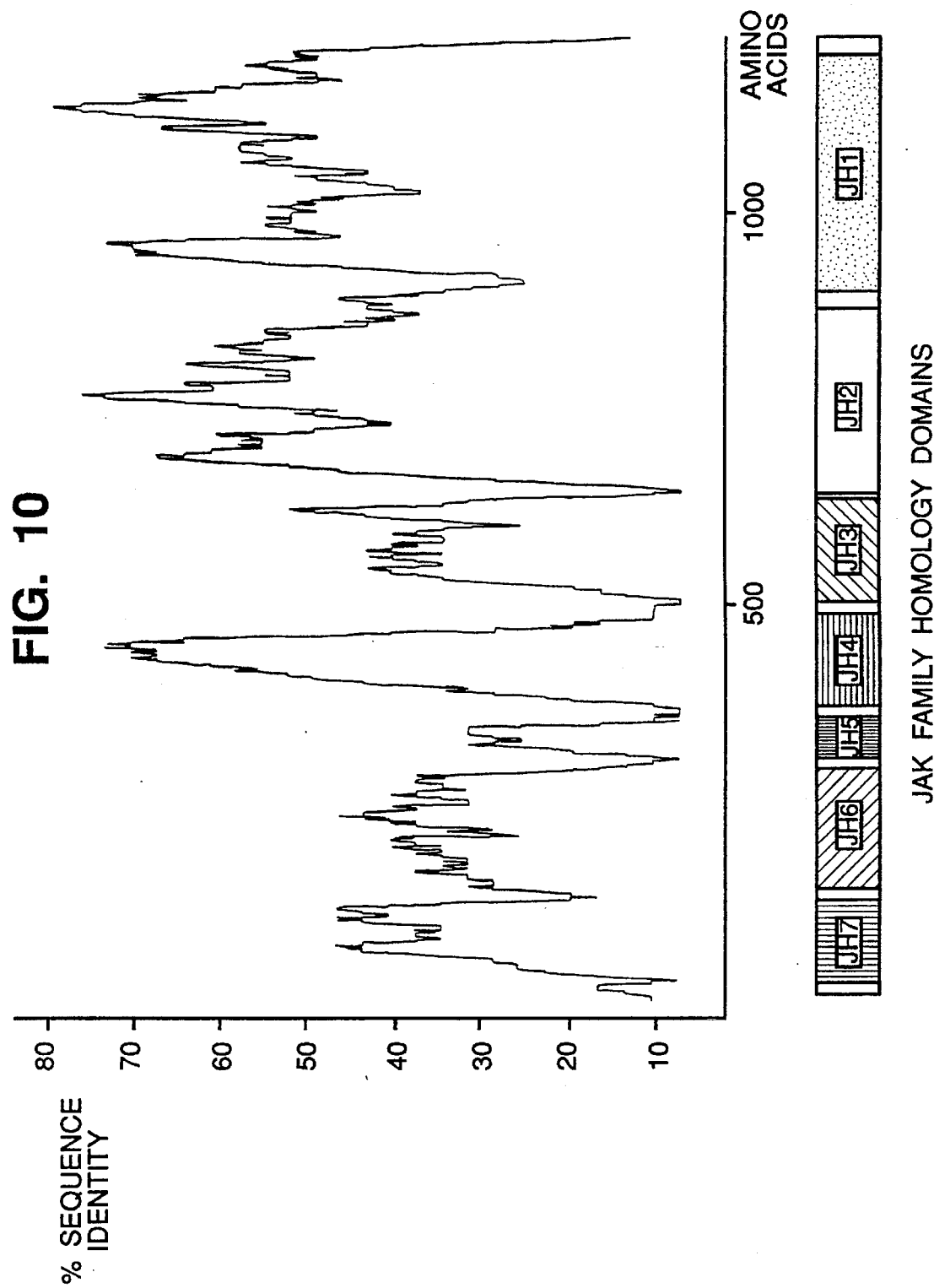

FIG. 10 is a graphical representation showing comparison of JAK1 and TYK2 amino acid sequences. The amino acid sequences of JAK1 (Wilks et al., 1991) and TYK2 (Firmbach-Kraft et al., 1990) were compared using the HOMOLOGY option in the programme SEQMATCH, using a window length of 21 amino acids. The ordinate of the graph represents the percentage identity between the two sequences, the abscissa represents the amino acid postion in JAK1 at which the particular level of identity was calculated. The shaded boxes below the graph represent arbitrarily ascribed JAK homology domains as discussed in the text and further demonstrated in FIG. 11.

Figure 11C:
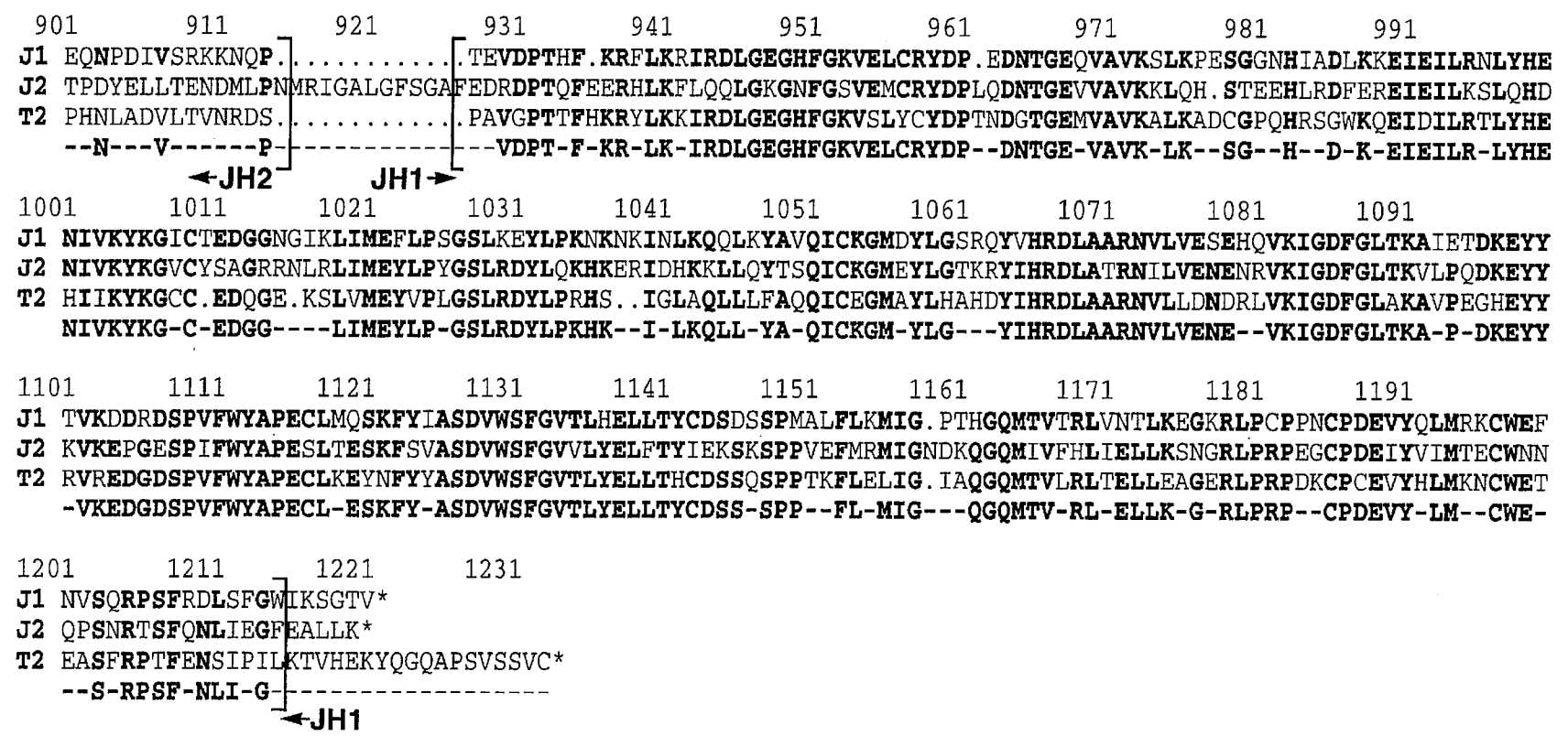

FIG. 11 is a representation showing amino acid sequence comparison of members of the JAK family of PTKs. The amino acid sequences of JAX1 (Wilks et al., 1991) (designated J1 in this figure), JAK2 (32 in this figure), and TYK2 (Firmbach-Kraft et al., 1990) (T2 in this figure) were aligned using the CLUSTAL program (Higgins and Sharp, 1988). The numbering system is relative only to the first amino acid of JAK1, and does not take into account the insertion of gaps into this sequence, it is therefore useful only as a relative measure of location. The extent of each of the JAK homology domains was determined with reference to the homology plot Shown in FIG. 10. Amino acid positions conserved in at least 2 out of the 3 sequences presented are bolded and presented below the TYK2 sequence as a consensus sequence.

FIG. 12 is a representation showing a comparison of the JH3/JH4 domain region with SH2 domains. The two SH2 domains of GAP (the more N-terminal domain denominated GAP-N (residues 178–269), the more C-terminal, GAP-C, (residues 348–438) (Trahey et al., 1988), and the SH2 domain of v-crk (residues 248–354) (Mayer et al., 1988) were compared with the JH3/JH4 of JAK1 (residues 425–536) (Wilks et al., 1991), JAK2 (residues 252–359) (this manuscript) and TYK2 (residues 449–555) (Firmbach-Kraft el al, 1990). Amino acids held in common between the two classes of sequence are denoted by vertical lines between the two sets of sequences. Conserved residues held in common by members of the same class of domain are bolded.

EXAMPLE 1

MATERIALS AND METHODS

Screening of cDNA libraries

Several cDNA libraries were screened according to the protocols outlined in Maniatis et al., (1982). cDNA libraries from Murine NFS TPA activated spleen (Clontech cat. #ML1018), murine swiss-albino 3T3 fibroblast (Clontech cat. #1023b), murine balb/c bone marrow (Clontech cat. #ML1007), murine swiss-webster whole brain (Clontech cat. #ML1002), murine ICR linoleic acid activated pleural macrophage (Clontech cat. #ML1005b), and human 1st-trimester foetal liver (Clomech cat. #HL1005b) were all generated in λgt 11. cDNA libraries from murine Balb/c testis (Clontech cat. #ML1020b), murine day 10 embryonic neuro-epithelium (Reid et al., 1990) and human foreskin fibroblast cell line AG1518 (Claesson-Welsh et al., 1989) were generated in λgtlO. around $10^6$ recombinants of each of these libraries were screened on each occasion.

Library screening was carried out as follows. The FD22 (JAK1) PCR clone was labelled by nick-translation (Maniatis et al., 1982) and used to screen the murine libraries. A murine cDNA clone of 1.8 kb was isolated amongst 3 other positives from the neuro-epithelial and bone marrow cDNA libraries. Two full-length human JAK1 cDNA clones were isolated from the unamplified human foreskin fibroblast cell-line AG1518 by using the murine cDNA as a probe. Hybridisation was at 650 C. in 6×SSC; 1% SDS; 0.5% Blotto; 200 µg/ml sonicated and denatured herring sperm DNA. After hybridisation, the stringency of the final wash was 0.2×SSC; 0.1% SDS at 650 C. Filters were autoradiographed overnight using Kodak XAR-5 X-ray film.

For JAK2, the murine macrophage was screened first with the FD 17 (JAK2) PCR clone, yielding 5 positives, and a portion of the longest cDNA clone isolated and used to screen the remaining cDNA libraries. Hybridisation conditions were as above for JAK1.

DNA sequences

Two strategies were employed for the sequencing of JAK1 and JAK2 cDNA clones. In the case of the human JAK1 sequence, the Erase-a-Base kit (PROMEGA) was employed to generate nested deletions of the largest EcoRI fragment. All of the murine JAK2 sequence data, and the remainder of the human JAK1 sequence, was determined using oligonucleotide primers based on previously determined DNA sequence. In each case the sequence information was generated using the dideoxynucleotide chain termination method (Sanger et al., 1977). All sequence information was determined on both strands.

Northern Analysis

Poly A+ mRNA samples were prepared as elsewhere described elsewhere (Wilks and Kurban, 1988). Aliquots (1 µg) were analysed by electrophoresis on a 1% agarose gel containing 2.2M formaldehyde; 20 mM MOPS,pH 6.8; 1 mM EDTA; 5 mM sodium acetate, and transferred to Hybond (Amersham, cat #RPN303N) or nitrocellulose (Schleicher & Schuell,BA85, cat #401196) membranes. Filters were prehybridised for 4 hr in 50% formamide containing 3×SSC; 5×Denhardts; 10 mM HEPES pH 7.0; 100 µg.ml 1; poly C;100 µg/ml denatured herring sperm DNA; 10 µg/ml E. coli DNA; 0.1% SDS, and hybridised in the same solution with nick-translated $^{32}$P-labelled murine or human JAK1 or JAK2 insert, for 18 hr. at 42° C. Filters were washed to a final stringency of 0.2×SSC; 0.1% SDS at 65° C., before exposure to Kodak XAR-5 X-ray film, with two intensifying screens.

Antibody Reagents and Protein Analysis

Polyclonal rabbit antisera M7 and M8 were raised against affinity purified pGEX/JAK1/1 bacterial fusion protein (see section on kinase assays). Polyclonal antibodies M3 and M4 against the C-terminal peptide (-TSFQNLIECFEALLKC-) (SEQ ID NO:4) of JAK1 were raised in rabbits. Peptide was coupled to Keyhole Limpet Heamocyanin with 0.05% gluteraldehyde, emulsified in Freunds' complete adjuvant and injected intradermally at several sites. The animals were boosted four and seven weeks later with coupled peptide emulsified in Freunds' incomplete adjuvant and bled ten days after the last injection.

Cells were metabolically labelled with either $^{35}$S-methionine or $^{32}$P-orthophosphate in methionine- or phosphate-free medium containing 100 µCi/ml and 1 mCi/ml isotope respectively. RIPA-buffer (20 mM Tris, pH 7.5 containing 1% Triton X100, 1% Na deoxycholate, 0.1% SDS, 1 mM EDTA, 1 mM PMSF) extracts were incubated on ice with antiserum and immune-complexes isolated using Protein A bearing Staphylococus aureus bacteria. Proteins were resolved by SDS-PAGE (Laemmli, 1970) and radioactively labelled bands detected by exposure to X-ray film (Kodak XAR-5). The RIPA buffer for $^{32}$P-labelled cells contained in addition 20 mM EDTA, 10 mM NaF, 100 µM orothovanadate as phosphatase inhibitors.

Phosphoamino-acid analysis of excised $^{32}$P-labelled bands was carried out exactly as described by Hunter and Sefton (1980) Western blot analysis was performed as described by Towbin et el. (1979) as modified in Ziemiecki et al (1990) using either alkaline phosphatase or $^{125}$I-labelled protein-A as a detection system.

Protein Kinase Assays

A variety of protocols have been tried in order to reveal the PTK activity of the JAK1 protein. First, extraction of murine mammary fibroblasts, Reichmann et al (1989) has been perform in a range of buffers, containing Triton-X100 or Nonident P40 (1.0%) alone or with added Sodium Deoxycholate (0.5% or 1.0%) or in RIPA buffer (containing 1.0% Triton-X100; 1.0% Sodium Deoxycholate; 0.1% Sodium Dodecylsulphate). Cells have been extracted in the presence or absence of phosphatase inhibitors, such as 20 mM EDTA, 10 mM NaF and 100 µM Na2V04.

After immunoprecipitation, kinase assays have been performed in a range of ATP concentrations (100 nM–10 mM) or with carrier-free γ-32P-ATP (Amersham cat #10169) in either 20 mM Tris, pH 7.4 or 50 mMM HEPES pH 7.4, with either 10 mM $Mn^{++}$, $Mg^{++}$ or $Zn^{++}$ as divalent cation. Incubations have been performed on ice (15 min), at 25° C. (15 min), at 30° C.(15 min) or at 37° C. (2 min) in the presence or absence of the phosphatase inhibitor Na2V04. Finally, γ-32P-GTP was employed as phosphate donor in lieu of γ-32P-ATP, with no success.

In order to generate the JAK1/glutathione transferase fusion proteins shown in FIG. 4, domain-1 (from nucleotides 1770–2672 in FIG. 2) and the PTK domain (from nucleotides 2672-end in FIG. 2. thus including 5 extra amino acids beyond the ATP binding glycine motif) were each fused into the BamHI site of pGEX2. The fusion protein was induced by the addition of 1 mM IPTG as described elsewhere (Smith and Johnson, 1983) and Western blot analysis performed on an induction time course with the M3 anti-JAK1 serum, and the anti-phosphotyrosine antiserum (Kamps and Sefton, 1988). Several sources of anti-phosphotyrosine antisera were tried. The data in FIG. 4b were obtained using a commercially available monoclonal antibody preparation PY-20 (ICN). In control experiments, induction of the insert-less pGEX or pGEX/JAK1 fusion protein produced no detectable tyrosine phosphorylation of bacterial substrates and the reactivity of the anti-phosphotyrosine antiserum could be completely abolished by the additional of phenyl phosphate.

Computer Aided Sequence Analysis

Amino acid sequence comparisons were performed using an alignment programme from the Staden-based suite of programmes on a VAX VMS 5.2. The phylogenetic analysis of the two kinase-like domains of JAK1 was performed using the tree-building concept of Fitch and Margoliash (1957) as implemented by Feng and Doolittle (1987). The SCORE programme used to construct the difference matrices from which the trees were derived using the BORD and BLEN programmes, were all the gift of Dr R. Doolittle of the University of California—San Diego.

The sequence alignment shown in FIG. 11 was assembled using the CLUSTRAL program (Higgins and Sharp, 1988) on a VAX VMS 5.2 minocomputer. The homology plot shown in FIG. 10 was assembled using the HOMOLOGY option of the programme SEQMATCH. Database searches with each of the JAK homolgoy domains was reformed using the FASTA programme, based on the Pearson/Lippman algorithm (Pearson and Lippman, 1988).

RACE/Anchor PCR

RACE/Anchor PCR (Frohman et al., 1990; Loh et. al, 1990) was performed by a modification of the original protocol. Briefly, 2 µg of poly(A+) mRNA is converted to cDNA using an Amersham cDNA synthesis kit (cat No. RPN 1256) and 40 ng. of a JAK2 specific oligonucleotide primer (5'-TACACCTTTAAATATTTTTGT-3') (SEQ ID NO:5). Prior to the addition of the reverse transcriptase, the reaction mixture was heated to 65° C. cDNA synthesis was inititated by the addition of 20 units of reverse transcriptase, and the reaction incubated at 55° C. for 75 minutes. The newly synthesised cDNA was recovered by passage through a spun sephadex column (Maniatis et al., 1982) followed by ethanol precipitation. The mRNA/cDNA heteroduplex was G-Tailed in 30 µl containing 140 mM potassium cacodylate, 30 mM Tris, (pH 7.2), 1 mM $CoCl_2$, 0.1 mM DTT, 6 mM dGTP and 15 units of TdT (IBI), for 10 minutes at 37° C. The reaction was terminated by heating to 65° C. for 15 minutes and then diluted to 500 µl with 10 Mm Tris. HCl (pH 7.5). 1 mM EDTA. For the RACE/Anchor PCR, 10 µl of the tailed cDNA was reconstituted into 100 µl PCR buffer (50 mM KCl, 10 mM Tris. HCl[pH 8.3], 1.5 mM $MgCl_2$, 0.01% gelatin, 200 µM of each dNTP) to this was added 50 ng of "poly-C" oligonucleotide primer (5'-CTCGAGTCGACGAATT$C_{14}$-3') and 2.5 units of TAO polymerase (Cetus). The complementary strand of the cDNA was synthesised with one cycle of 95° C. (5 minutes), 52° C. (5 minutes) and 68° C. (40 minutes), whereupon 500 ng of the "RACE/Anchor" primer (5'-CTCGAGTCGACGAATTC-3') (SEQ ID NO: 6) and a nested JAK2 specific primer (5'-CTTGCTTAATACTGACATCA-3') (SEQ ID NO: 7) were added and the reaction mix subjected to 30 cycles of 95° C. (1 minute), 52° C. (2 minutes) and 68° C. (5 minutes). The PCR product was phenol/chloroform extracted, precipitated and resuspended in 100 µl of water. The amplified material was then kinased, size fractionated on a low-melting temperature agarose gel and cloned into SmaI cleaved M13 mp8. Plaques were screened by hybridisation with a JAK2 cDNA and positives sequenced.

EXAMPLE 2

Isolation and DNA sequencing or cDNA clones encoding JAK1

JAK1 cDNA was cloned using PCR. Northern analysis (FIGS. 1a and b) demonstrated that in both mouse and human tissues and cell lines FD22 (JAK1) was encoded by a single widely expressed 5.4 kb mRNA. Human cDNA clones of FD22 (JAK1) were isolated from a human foreskin fibroblast cell line (AG 1518) cDNA library (Claesson-Welsh et al., 1989). Two of the 8 primary isolates cloned contained inserts which were candidates for being full-length cDNAs (~5.3 kb).

The nucleotide sequence of human JAK1 is shown in FIG. 2. The 5' end the clone has stop codons in all 3 reading frames prior to the putative initiation ATG. Two ATG start codons in frame with the longest open reading frame were formal at positions 40 and 76 in the nucleotide sequence shown in FIG. 2. The first of these is embedded in a particularly poor "Kozak" consensus sequence (Kozak, 1984) (-TAAATGCAG-) (SEQ ID No:9), whereas the second matches strongly with the optimal consensus sequence defined by Kozak, namely -GCCATGGCT- (SEQ ID NO:10). The second ATG is considered to be the initiation codon for this protein, since the first one transgresses one of the strongest correlations found in the sequences which precede initiation codons, namely the presence of a T residue (in lieu of an A residue) 3 nucleotides before the ATG sequence. At the 3' end, an in-frame stop codon at position 3502 defines the C-terminus of the protein. A large (1.405 kb) 3' untranslated region containing a polyaclenylation signal completes the mRNA sequence.

The JAK1 coding region of 3426 bp encodes a protein of 1142 amino-acids with a calculated molecular mass of 132,000 daltons. The PTK catalytic domain is located towards the C-terminus of the JAK1 protein (FIG. 2). In describing the structural features of this domain we have chosen to adopt the nomenclature of Hanks et al (1988). The putative ATP binding site composed of the motif GLY-X-GLY-X-X-GLY- (SEQ ID No: 3) (subdomain 1) followed by an invariant lysine residue (sudomain II) is located between amino acid residues 871 and 896 of the JAK1 protein. The core motifs of the PTK catalytic domain (subdomains VI to IX) are also in their appropriate locations, and are well conserved with respect to their primary sequence and their relationship to each other. The presence of a tyrosine residue at position 1022 in the JAK1 protein, 11 residues C-terminal to sub-domain VII (a similarly placed tyrosine is a site of tyrosine autophosphorylation in v-fps; Weinmaster et al., 1984) is a consistent feature of members of the PTK family and is considered diagnostic of membership of this class of kinases. The arginine residue at position 1126 (domain XI) marks the end of the highly conserved regions of the PTK catalytic domain and the entire catalytic domain of 255 amino acids is approximately 28% (with c-fes; Wilks and Kurbon, 1988) to 37% (with TRK; Kozman et al., 1988) identical to other functionally defined PTKs. Finally, there is a rare variant of the highly conserved subdomain VIII motif (residues 1032–1039), which is believed to lie close to the active site (Hanks et al., 1988). The presence of phenylalanine and tyrosine flanking the conserved tryptophan in this motif is unique to JAK1 and JAK2.

A second protein Kinase-related domain (designated here Domain-1) is located between amino acids 578 and 824, 47 amino acids N-terminal to the putative PTK domain. All of the conserved elements of protein Kinases are preserved spatially in this domain. In FIG. 2 these elements are numbered with respect to their similarity to the subdomains of protein Kinases described by Hanks et al, (1988) (with the suffix$_a$, e.g. III$_a$) and the amino acid sequences of the two Kinases-related domains of JAK1 are compared to each other end to human CDC2 (Lee and Nurse, 1987) in FIG. 3a. The overall structural similarity of this domain to the kinase domains of both the PTK and threonine/serine kinase families strongly suggest that this region of the protein also functions as a protein Kinase. There are, however, significant differences in the sequences of key motifs within this domain which suggest that Domain-1 may confer a catalytic activity other than serine/threonine or tyrosine phosphorylation. For example, sub-domain VI$_a$ is poorly conserved with respect to the equivalent motifs in the other kinase families, and the normally invariant -ASP-PHE-GLY- sequence of the PTK end threonine/serine kinase families (sub-domain VII$_a$) is replaced by the motif ASP-PRO-GLY- in Domain-1 of JAK1. As has been noted elsewhere, the conservation of the precise sequence of sub-domain VI in the PTK and threonine/serine kinase families appears to correlate with the substrate specificity of the kinase. Thus, it is possible that Domain-1 of the JAK1 kinase has a substrate specificity other than that exhibited by the PTK and threonine/serine kinase has a substrate specificity other than that exhibited by the PTK and threonine/serine kinases. In support of this notion there are subtle differences in the normally consistent spacing between certain key motifs in Domain-1 of JAK1. The components of the ATP binding site (sub-domains I$_a$ and II$_a$) are some 7 amino acids further apart in this domain that they are in both the PTK family and the threonine/serine kinase family. Moreover, the spacing between sub-domains VI$_a$ and VII$_a$ in this region is also longer by 9 amino acids. Conversely, the distance between sub-domains VII$_a$ and IX$_a$ is 7 amino acids shorter than the corresponding region in the PTK catalytic domain. The overall structure of this domain can be expected to be somewhat different to the catalytic domains of the members of the PTK and threonine/serine kinase families.

The sequences N-terminal to Domain-1 bear no homology to any other portion of a previously described protein kinase. Specifically, no homology was detected to the SH2 domain described for the cytoplasmic PTKs such as c-fes/fps (Sadowski et al., 1986) GAP (Trahey et al., 1988) and the phospholipase-C family of proteins (Suh et al., 1988). This is a particularly interesting observation since no other non-receptor PTK has been described which lacks this feature. A hydrophilicity plot failed to demonstrate the present of a hydrophobic domain characteristic of the growth factor receptor type of PTK (FIG. 3b) suggesting that this protein is wholly intracellular like other members of the non-receptor class of PTKs. The one outstanding feature of the JAK1 hydropathy plot is the highly hydrophilic sequence between residues 320–350. This sequence is not conserved in the murine JAK2 protein however, its remarkable nature suggests that it may well be involved in some function of the JAK1 protein.

Expression of JAK1 protein

Several antisera were generated against the human JAK1 protein. Polyclonal antisera directed against the hexadecamer -TSFQNLIECFEALLKC- (the C-terminal (SEQ ID NO: 4) 15 amino acids of JAK1) were raised in rabbits and used to investigate the nature of the JAK1 protein. A second rabbit antiserum was generated using a pGEX bacterial fusion protein containing the entire Domain-1 region of the human JAK1 protein (see example 1). Preliminary sequence analysis of cDNA clones of murine JAK1 demonstrated that the C-terminus of the human and murine versions of this protein were identical whereas the murine and human Domain-1 regions exhibited a very high degree of identity. Both systems have thus been used interchangably in the investigation of the properties of the JAK1 protein.

Both antisera have been used for Western blot analyses and immunoprecipitation studies and the data confirm the mRNA expression studies shown in FIG. 1. For example, antisera M3 and M8 both immunoprecipitate a protein of the same apparent molecular weight (130 kDaltons) from $^{35}$S-methionine labelled murine breast fibroblasts (FIG. 4a). From the same source, $^{32}$P-orthophosphate labelled JAK1 was immunoprecipitated as a phosphothreonine and phosphoserine containing phosphoprotein. It is a feature characterstic of members of the protein tyrosine kinase family that they are able to accomplish an act of self phosphorylation in vitro. Intriguingly, despite the high degree of sequence similarity held by the PTK-related sequence of JAK1 to the PTK family in general, it was not possible to demonstrate tyrosine kinase catalytic activity in immunoprecipitates of this protein from any of the murine or human sources tested. A wide range of possibilities has been tested in search of suitable conditions for the demonstration of this activity. These are listed in Example 1. The reason for the lack of activity may lie with a steric effect of the antibody in the active site of the enzyme.

Figure 1B:
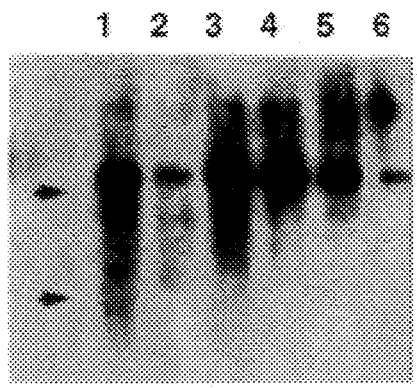

In order to determine whether domain-1 or the PTK domain, in isolation, bore catalytic activity, bacterial fusion proteins of each were generated with the glutathione transferase protein of Schistosoma iaponicum (Smith and Johnson, 1988) and an attempt was made to demonstrate with the aid of anti-phosphotyrosine antibodies (Kamps and Sefton, 1988) the co-ordinate induction of the fusion protein and tyrosine phosphorylated protein. In this system there is no cross-reactive background of the anti-phosphotyrsine antiserum, since there are no tyrosine kinases in bacteria (FIG. 1b). The phosphorylation of bacterial proteins on tyrosine is thus easily detectable with such a serum. In this series of experiments neither pGEX without insert nor pGEX bearing Domain-1 (pGEX/JAK/1/1) demonstrated any tyrosinc kinase activity. The pGEX/JAK/1 fusion protein was further purified by affinity chromatography on a reduced glutathione column and have failed to detect any kinase activity using either histones, casein or enolase as an exogenous substrate. The pattern of inducible tyrosine phosphorylation exhibited by the pGEX PTK fusion protein (pGEX/JAK/2) (FIG. 4b) is ususually simple for an ectopically expressed PTK fusion protein. Remarkably, the autophosphorylation of the fusion protein itself does not seem to occur, an observation which may go some way toward explaining why we have had difficulty in demonstrating PTK activity in the intact protein.

cDNA clones covering the coding region of the PCR clone FD17 (JAK2) have been isolated from a range of murine cDNA libraries. The predicted amino acid sequences of JAK2 and JAK1 show several regions of significant similarity to each other (FIG. 5, see also Example 3).

Phylogenetic analysis

The phylogenetic relationship of the catalytic domain of most of the protein kinases has been determined using the tree-building programme of Feng and Doolittle (1987). FIG. 6 shows the phylogenetic relationship of the two kinase-related domains of the JAK1 protein to the rest of the kinase family. It is concluded from this family tree that these two domains had a common ancestor which pre-dated the development of the PTK sub-family. It is of interest to note that the kinase-related domains of the ANP-receptor/guanylate cyclase family diverge at a point close by.

EXAMPLE 3

Cloning and sequencing of JAK2

Sequence of Murine JAK2

The PCR clone FD17 was used as a basis to begin the cloning of longer cDNA clones of murine JAK2. cDNAs were isolated from a range of cDNA libraries, and by RACE (Frohman et al., 1989, Loh et al., 1989). The sequence of murine JAK2 is presented in FIG. 8. The predicted amino acid sequence indicates that this protein is highly related to JAK1. At the C-terminus, and extending approximately 270 amino acids towards the N-terminus (AA 715-980), are sequences bearing all the hall marks of a PTK catalytic domain. These are labelled in FIG. 8 according to the Hanks nomenclature. Immediately N-terminal to this (AA 400-650) lies the kinase-related domain characteristic of this class of PTKs (Wilks et al., 1991). The approach outlined in example 2 in relation to JAK1 was followed and assigned these kinase related domains according to the Hanks nomenclature, appending the suffix Na to denote their origin. One unusual feature of this domain is an apparent insertion of seven amino acids between elements VIIa and VIIIa (Hanks nomenclature; Hanks and Quinn, 1991) with respect to other members of this family. This feature appeared in only one clone of the four sequenced which covered this region, and it remains possible that its presence is due to an infrequent splicing abberation, rather than being of functional significance.

Distribution of JAK2

Northern analysis of the expression of JAK2 in the mouse demonstrated two mRNA transcripts (4.8 and 4.4 kb) hybridizing to the JAK2 probe under low and high stringency hybridization conditions (FIG. 9). It is intriguing to note that the levels of these transcripts alter with respect to one another in different to tissues. For example. the kidney, spleen and lung appear to express predominantly the larger form, whereas ovary, placenta, skeletal (sk) muscle and all murine cell lines analyzed express both forms at about equal levels.

Under low stringency hybridization conditions the murine JAK2 probe recognizes human JAK2 RNA (K562), however, only the smaller transcript of 4.4 kb could be detected. At this point, the origins of either of the two transcripts are unclear and no differential splicing events which could account for the differences between them could be detected. However, the major source of size differential in these transcripts may lie in the use of different polyadenylation signals. JAK2 is widely expressed in mouse organs, albeit to different levels. High expression was found in thymus, skeletal muscle, ovary and placenta, but JAK2 transcripts were barely detectable in testes or liver. In addition, JAK2 expression was detected in murine cell lines of fibroblastic (30F, NIH), epithelial (31D) and hemopoietic (30.1) origin.

JAK Family Homology Domains.

The cloning of JAK1 and JAK2 has facilitated the identification of JAK fatally homology domains. FIG. 10 shows a comparison of the amino acid sequences of JAK1. Sequence identity between these two proteins manifests itself as seven clearly defined homology domains. These seven domains are defined at a primary sequence level in FIG. 11. The PTK domain is classified as the JAK-homology Domain 1 (JH1), the second kinase related domain as the JH2 Domain, and so on to JH7. The boundaries of the JAK homology domains are arbitrary, and may or may not define functional domains. However, their delineation is a useful device to aid the consideration of the overall structural similarity of this class of proteins. The structure of the JH1 and JH2 Domains are described in Example 2. The JH3 is one of the least highly conserved of the JAK homology domains, each family member bearing between 35% (JAK2) to 50% (JAK1) of the deduced consensus sequence. The JH4 domain bears the sequence -GLYVLRWS- (SEQ ID NO: 11) close to its C-terminal boundary, which has some degree of homology to the SH2 domain core sequence (see below). In addition, the most highly conserved sub-domain of this region bears a potential tyrosine phosphorylation site, namely, -VDGYFRI- (SEQ ID NO: 12). Overall, the JH4 domain has between 51% (JAK2) and 64% (JAK1) of the deduced consensus sequence for this domain. Each of the remaining JAK homology domains has been independently screen against the NBRL and EMBL database using the FASTA programme. There were no compelling homologies found with anything in these databases. It is concluded that these domains are structurally and functionally conserved in members of the JAK family of PTKs, but may not, in contradistinction to the SH2 and SH3 domains of the src family of PTKs, have a role to play in other signal transduction molecules.

The apparent absence of an SH2 domain in any of the JAK family of PTKs is intriguing. Subtle sequence similarities have been detected between SH2 consesus sequence and portions of the JH3 and JH4 domains (H. Hanafusa and A. Bernards, personal communication). FIG. 12 shows an alignment of these two domains. Whilst the similarity of the JH3 domain to SH2 domains is most evident in the region surrounding the SH2 core sequence (FLVRES), the homology does not extend far in either direction beyond this region, and only reappears again close to the C-terminal boundary of the SH2 domain. This lack of exetensive homology, particularly in many of those elements most highly conserved between SH2 domain (Koch et al., 1991) (presumably indicating those residues most intimately involved in the conserved function of this domain), suggest that the homology detected is either happenstance, or the product of considerable sequence divergence in evolution. The SH2 domain is currently believed to interact with phosphorylated tyrosine residues on the substrates of PTKs (reviewed in Pawson, 1989; Koch et al., 1991). Whether the JH3/JH4 domain play a similar function role remain to be determined.

EXAMPLE 4

To show that JAKs are represented in a range of animals, oligonucleotide probes were prepared and used to amplify and screen genomes from a variety of animals. JAK DNA was detected in Drosophila, xenopus, mouse and human genomes. The main conserved sequence was DPG common to all animals tested.

REFERENCES:

Claesson-Welsh, L., Eriksson, A., Westermark, B. and Heldin, C. H., *Proc. Nat. Acad. Sci. USA* 86: 4917–4921, 1989.

Feng, D. F. and Doolittle, R. F. *Jour. Mol. Evolution* 25: 351–360, 1987.

Fitch, W. M. and Margoliash, E., *Science* 12: 279–284, 1967.

Hunter, T., and Sefton, B. M. *Proc. Nat. Acad. Sci.* 77; 1311–1315, 1980.

Kamps, M. P., and Sefton, B. M. *Onogene* 2: 305–315, 1988.

Kozak, M. *Nucleic Acids Res.* 12: 857–872, 1984.

Kozma, S. C. Redmond, S. M. S., Xiano-Chang, F., Saurer, S. M. Groner, B., and Hynes, N. E. *EMBO J.* 7: 147–154, 1988.

Kyte, J. and Doolittle, R. F. *J. Mol. Biol.* 157: 105–132, 1982.

Laemmli, U. K. *Nature (London)* 227: 680–685, 1970.

Lee, M. G. and Nurse, P. *Nature (London)* 327: 31–35, 1987.

Maniatis, T., Fritsch, E. F., and Sambrook, J., in *Molecular Cloning: A Laboratory Manual* Cold Spring Harbor, N.Y. 1982.

Moran, M. F., Koch, C. A., Sadowski, I., and Pawson, T. *Oncogene* 3: 6655–672, 1988.

Reichmann, E., Ball, R., Groner, B., and Friis, R. R. *J. cell Biol.* 108: 1127–1138, 1989.

Smith, D. B. and Johmon, K. S. *Gene* 67: 31–40, 1988.

Suh, P., Ryu, S. H., Moon, K. H., Suh, H. W., and Rhee, S. G. *Cell* 54: 161–169 1988.

Towbin, H., Stehelin, T., and Gordon, J., *Proc. Nat. Acad. Sci. USA* 76:4350–4354, 1979.

Weinmaster, G., Zoller, M. M., Smith, M., Hinze, E., and Pawson, T. *Cell* 37: 559–568, 1984.

Wilks, A. F. and Kurban, R. R. *Oncogene* 3: 289–294, 1988.

Ziemiecki, A, Mueller, R. G., Xiao-Chang, F., Hynes, N. E. and Kozma, S., *EMBO J.* 9: 191–196,1990.

Dymecki, S. M., Neiderhuber, J. E., and Desiderio, S.v. *Science* 247: 332–336, 1990.

Firmbach-Kraft, I., Byers, M., Showes, T., Dalla-Favera, R., and Krolewski, J. J., *Oncogene* 5: 1329–1336,1990.

Frohman, M. A., Dush, M. K. and Martin, G., *Proc. Nat. Acad. Sci. USA* 85: 8998–9002, 1988.

Hanks, S. K. and Quinn, A. M, *Methods in Enzymolog* 200: 38–62, 1991.

Hanks, S. K., Quinn, A. M. and Hunter, T. *Science* 241: 42–52, 1988.

Higgins, D. G. and Sharp, P. M. *Gene* 73: 237–244, 1988.

Holtzman, D. A., Cook, W. D. and Dunn, A. R. *Proc. Nat. Acad. Sci. USA* 84: 8325–8329, 1987.

Koch, C. A., Anderson, D., Moran, M. F., Ellis, C., and Pawson, T., 252: 668–674, 1991.

Loh, E. Y., Elliott, J. f., Cwirla, S., Lanier, L. L. and Davis, M. M. *Science* 243: 217–220, 1989.

Marth, J. D., Peet, R., Krebs, E. G., and Perimutter, R. M. *Cell* 43: 393–404, 1985.

Martinez, R., Mathey-Prevot, B., Bernards, A. and Baltimore, D. *Science* 237: 411–414, 1987.

Mayer, B. J., Hamaguchi, H., and Hanafuasa, H., *Nature* 332: 272–274, 1988.

Nishizawa, M., Semba, K., Yoshida, M. C. Yamamoto, T., Sasaki, M., and Toyoshima, K. *Mol. Cell. Biol.* 6: 511–517, 1986.

Pawson, T., *Oncogene* 3: 491–495, 1988.

Pearson, W. R. and Lippman, D. J. *Proc. Natl. Acad. Sci.* 85: 2444–2448, 1988.

Reid, H. H., Wilks, A. F., and Bernard, O., *Proc. Nat. Acad. Sci.* 87: 1596–1600, 1990.

Sadowski, I., Stone, J. C., and Pawson, T. *Mol. Cell. Biol.* 6: 4396–4408 1986.

Sanger, F., Nicklen, S., and Couson, A. R., *Proc. Nat. Acad. Sci. USA* 74: 5463–5467, 1977.

Semba, K., Nishizawa, M., Myajima, N., Yoshida, M. C., Sukagawa, J., Yamanishi, Y., Sasaki, M., Yamamoto, T., and Toyoshima, K., *Proc. Natl. Acad. Sci.* 83: 5459–5463, 1986.

Sukegawa, J., Semba, K., Yamanashi, Y., Nishizawa, M., Myajima, N., Kamamoto, T., and Toyoshima, K., *Mol. Cell. Biol.* 7: 41–47, 1987.

Trahey, M., Wong, G., Halenbeck, R., Rubinfeld, B., Martin, G. A., Ladner, M., Long, C. M., Crosier, W. J., Watt, K., Koths, K., and McCormick, F., *Science* 243: 1697–1700, 1988.

Wilks, A. F., *Process in Growth Factor Research* 2: 97–111, 1990.

Wilks, A. F., Harpur, A., Kurban, R. R., Ralph, S. J., Zuercher, G., and Ziemiecki, A. *Molecular and Cellular Biology* 11: 2057–2065, 1991.

Yamamishi, Y., Fukushige, S. I., Semba, K., Sukegawa, J., Miyajima, N., Matsubara, K. I., Yamamoto, T. and toyoshima, K., *Molec. Cell. Biol.* 7: 237–243, 1987.

---

We claim:

1. Isolated antibody which specifically binds to a protein which (i) has tyrosine kinase activity, (ii) has more than one protein kinase domain, (iii) has no src homology 2 (SH2) domains, and (iv) is encoded by SEQ ID NO: 1 or SEQ ID NO: 2.

2. The isolated antibody of claim 1, wherein said antibody is a monoclonal antibody.

3. Hybridoma cell line which produces a monoclonal antibody which (i) specifically binds to a protein which has tyrosine kinase activity, (ii) has more than one protein kinase domain, (iii) has no src homology 2 domains, and (iv) is encoded by SEQ ID NO: 1 or SEQ ID NO: 2.

4. The antibody of claim 1, which specifically binds to the protein encoded by SEQ ID NO: 1.

5. The antibody of claim 1, which specifically binds to the protein encoded by SEQ ID NO: 2.

6. The antibody of claim 1, which specifically binds to the peptide of SEQ ID NO: 3.

7. The antibody of claim 1, which specifically binds to the peptide of SEQ ID NO: 4.

8. The antibody of claim 1, which specifically binds to the peptide of SEQ ID NO: 11.

9. The antibody of claim 1, which specifically binds to the peptide of SEQ ID NO: 12.

* * * * *

UNITED STATES PATENT AND TRADEMARK OFFICE
CERTIFICATE OF CORRECTION

PATENT NO. : 5,658,791
DATED : August 19, 1997
INVENTOR(S) : Wilks et al.

It is certified that error appears in the above-identified patent and that said Letters Patent is hereby corrected as shown below:

Column 2,
Line 8, change "mount" to read as -- amount --.
Line 34, change "anologues" to read as -- analogues --.
Lines 39-40, change "methytacetimidate" to read as -- methylacetimidate --.

Column 4,
Line 36, change "fractionsted" to read as -- fractionated --.
Line 48, change "sequent" to read as -- sequence --.
Line 64, change "domaim" to read as -- domains --.

Column 5,
Line 43, change "ming" to read as -- using --.
Line 43, change "anti-phosphoryrosine" to read as -- anti-phosphotyrosine --.
Line 56, change "S" to read as -- $ --.

Column 6,
Lines 5-6, change "nantueric" to read as -- naturetic --.
Line 10, change "or" to read as -- of --.
Line 61, change "JAX1" to read as -- JAK1 --.
Line 62, change "32" to read as -- J2 --.

Column 7,
Line 3, change "Shown" to read as -- shown --.
Line 16, change "el" to read as -- et --.
Line 61, change "sequences" to read as -- sequencing --.

Column 8,
Line 51, change "el" to read as -- al --.
Line 58, insert a comma after "alone" to read as -- alone, --.
Line 59, change "Nonident" to read as -- Nonidet --.

Column 9,
Line 33, change "(1957)" to read as -- (1967) --.
Line 40, change "minocomputer" to read as -- minicomputer --.
Line 43, change "homolgoy" to read as -- homology --.

UNITED STATES PATENT AND TRADEMARK OFFICE
CERTIFICATE OF CORRECTION

PATENT NO. : 5,658,791
DATED : August 19, 1997
INVENTOR(S) : Wilks et al.

It is certified that error appears in the above-identified patent and that said Letters Patent is hereby corrected as shown below:

Column 10,
Line 22, change "or" to read as -- of --.
Line 34, change "end the" to read as -- end of the --.
Line 37, change "formal" to read as -- found --.
Line 50, change "polyaclenylation" to read as -- polyadenylation --.

Column 11,
Line 15, change "Kinase" to read as -- kinase --.
Line 24, change "end" to read as -- and --.
Line 28, change "Kinase" to read as -- kinase --.
Line 35, change "end" to read as -- and --.

Column 12,
Line 48, change "iaponicum" to read as -- japonicum --.
Line 55, change "1b" to read as -- 4b --.

Column 13,
Line 10, change "domain" to read as -- domains --.

Column 14,
Line 10, change "fatally" to read as -- family --.
Line 34, change "screen" to read as -- screened --.
Line 44, change "sequence" to read as -- sequences --.
Line 52, change "exetensive" to read as -- extensive --.
Line 56, change "suggest" to read as -- suggests --.
Line 62, change "function" to read as -- functional --.
Line 62, change "remain" to read as -- remains --.

Column 15,
Line 15, change "Onogene" to read as -- Oncogene --.
Line 28, change "6655" to read as -- 665 --.
Line 29, change "cell" to read as -- Cell --.
Line 33, insert comma after "169" to read as -- 169, --.

UNITED STATES PATENT AND TRADEMARK OFFICE
CERTIFICATE OF CORRECTION

PATENT NO. : 5,658,791
DATED : August 19, 1997
INVENTOR(S) : Wilks et al.

It is certified that error appears in the above-identified patent and that said Letters Patent is hereby corrected as shown below:

Column 16,
Line 1, change "Enzymolog" to read as -- Enzymology --.
Line 25, remove italic in "*T*" to read as -- T --.
Line 26, insert comma after "4408" to read as -- 4408, --.

Signed and Sealed this

Twentieth Day of November, 2001

*Attest:*

*Nicholas P. Godici*

NICHOLAS P. GODICI
*Attesting Officer*     *Acting Director of the United States Patent and Trademark Office*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
      ( A ) LENGTH: 4234 base pairs
      ( B ) TYPE: nucleic acid
      ( C ) STRANDEDNESS: single
      ( D ) TOPOLOGY: linear ( i i ) MOLECULE TYPE: nucleic acid ( x i ) SEQUENCE DESCRIPTION: SEQ ID NO: 1:

TGGCCGCCTA GCGAGCTGCC GGTCGACCCC AGCCAGCCGA GCGACGGGCG CTGCCTGGCC    60

```
CAGGGCACAC GGAAGTGCGC TTCTCTGAAG TAGCTTTGGA AAGTAGAGAA GAAAATCCAG        120

TTTGCTTCTT GGAGAACACT GGACAGCTGA ATAA ATG CAG TAT CTA AAT              169
                                     Met Gln Tyr Leu Asn
                                                     -10

ATA AAA GAG GAC TGC AAT GCC ATG GCT TTC TGT GCT AAA ATG AGG            214
Ile Lys Glu Asp Cys Asn Ala Met Ala Phe Cys Ala Lys Met Arg
        -5                  +1                  5

AGC TCC AAG AAG ACT GAG GTG AAC CTG GAG GCC CCT GAG CCA GGG            259
Ser Ser Lys Lys Thr Glu Val Asn Leu Glu Ala Pro Glu Pro Gly
        10                  15                  20

GTG GAA GTG ATC TTC TAT CTG TCG GAC AGG GAG CCC CTC CGG CTG            304
Val Glu Val Ile Phe Tyr Leu Ser Asp Arg Glu Pro Leu Arg Leu
        25                  30                  35

GGC AGT GGA GAG TAC ACA GCA GAG GAA CTG TGC ATC AGG GCT GCA            349
Gly Ser Gly Glu Tyr Thr Ala Glu Glu Leu Cys Ile Arg Ala Ala
        40                  45                  50

CAG GCA TGC CGT ATC TCT CCT CTT TGT CAC AAC CTC TTT GCC CTG            394
Gln Ala Cys Arg Ile Ser Pro Leu Cys His Asn Leu Phe Ala Leu
        55                  60                  65

TAT GAC GAG AAC ACC AAG CTC TGG TAT GCT CCA AAT CGC ACC ATC            439
Tyr Asp Glu Asn Thr Lys Leu Trp Tyr Ala Pro Asn Arg Thr Ile
        70                  75                  80

ACC GTT GAT GAC AAG ATG TCC CTC CGG CTC CAC TAC CGG ATG AGG            484
Thr Val Asp Asp Lys Met Ser Leu Arg Leu His Tyr Arg Met Arg
        85                  90                  95

TTC TAT TTC ACC AAT TGG CAT GGA ACC AAC GAC AAT GAG CAG TCA            529
Phe Tyr Phe Thr Asn Trp His Gly Thr Asn Asp Asn Glu Gln Ser
        100                 105                 110

GTG TGG CGT CAT TCT CCA AAG AAG CAG AAA AAT GGC TAC GAG AAA            574
Val Trp Arg His Ser Pro Lys Lys Gln Lys Asn Gly Tyr Glu Lys
        115                 120                 125

AAA AAG ATT CCA GAT GCA ACC CCT CTC CTT GAT GCC AGC TCA CTG            619
Lys Lys Ile Pro Asp Ala Thr Pro Leu Leu Asp Ala Ser Ser Leu
        130                 135                 140

GAG TAT CTG TTT GCT CAG GGA CAG TAT GAT TTG GTG AAA TGC CTG            664
Glu Tyr Leu Phe Ala Gln Gly Gln Tyr Asp Leu Val Lys Cys Leu
        145                 150                 155

GCT CCT ATT CGA GAC CCC AAG ACC GAG CAG GAT GGA CAT GAT ATT            709
Ala Pro Ile Arg Asp Pro Lys Thr Glu Gln Asp Gly His Asp Ile
        160                 165                 170

GAG AAC GAG TGT CTA GGG ATG GCT GTC CTG GCC ATC TCA CAC TAT            754
Glu Asn Glu Cys Leu Gly Met Ala Val Leu Ala Ile Ser His Tyr
        175                 180                 185

GCC ATG ATG AAG AAG ATG CAG TTG CCA GAA CTG CCC AAG GAC ATC            799
Ala Met Met Lys Lys Met Gln Leu Pro Glu Leu Pro Lys Asp Ile
        190                 195                 200

AGC TAC AAG CGA TAT ATT CCA GAA ACA TTG AAT AAG TCC ATC AGA            844
Ser Tyr Lys Arg Tyr Ile Pro Glu Thr Leu Asn Lys Ser Ile Arg
        205                 210                 215

CAG AGG AAC CTT CTC ACC AGG ATG CGG ATA AAT AAT GTT TTC AAG            889
Gln Arg Asn Leu Leu Thr Arg Met Arg Ile Asn Asn Val Phe Lys
        220                 225                 230

GAT TTC CTA AAG GAA TTT AAC AAC AAG ACC ATT TGT GAC AGC AGC            934
Asp Phe Leu Lys Glu Phe Asn Asn Lys Thr Ile Cys Asp Ser Ser
        235                 240                 245

GTG TCC ACG CAT GAC CTG AAG GTG AAA TAC TTG GCT ACC TTG GAA            979
Val Ser Thr His Asp Leu Lys Val Lys Tyr Leu Ala Thr Leu Glu
        250                 255                 260

ACT TTG ACA AAA CAT TAC GGT GCT GAA ATA TTT GAG ACT TCC ATG            1024
```

```
     Thr  Leu  Thr  Lys  His  Tyr  Gly  Ala  Glu  Ile  Phe  Glu  Thr  Ser  Met
          265                      270                      275

TTA  CTG  ATT  TCA  TCA  GAA  AAT  GAG  ATG  AAT  TGG  TTT  CAT  TCG  AAT                1069
Leu  Leu  Ile  Ser  Ser  Glu  Asn  Glu  Met  Asn  Trp  Phe  His  Ser  Asn
     280                      285                      290

GAC  GGT  GGA  AAC  GTT  CTC  TAC  TAC  GAA  GTG  ATG  GTG  ACT  GGG  AAT                1114
Asp  Gly  Gly  Asn  Val  Leu  Tyr  Tyr  Glu  Val  Met  Val  Thr  Gly  Asn
     295                      300                      305

CTT  GGA  ATC  CAG  TGG  AGG  CAT  AAA  CCA  AAT  GTT  GTT  TCT  GTT  GAA                1159
Leu  Gly  Ile  Gln  Trp  Arg  His  Lys  Pro  Asn  Val  Val  Ser  Val  Glu
     310                      315                      320

AAG  GAA  AAA  AAT  AAA  CTG  AAG  CGG  AAA  AAA  CTG  GAA  AAT  AAA  GAC                1204
Lys  Glu  Lys  Asn  Lys  Leu  Lys  Arg  Lys  Lys  Leu  Glu  Asn  Lys  Asp
     325                      330                      335

AAG  AAG  GAT  GAG  GAG  AAA  AAC  AAG  ATC  CGG  GAA  GAG  TGG  AAC  AAT                1249
Lys  Lys  Asp  Glu  Glu  Lys  Asn  Lys  Ile  Arg  Glu  Glu  Trp  Asn  Asn
     340                      345                      350

TTT  TCA  TTC  TTC  CCT  GAA  ATC  ACT  CAC  ATT  GTA  ATA  AAG  GAG  TCT                1294
Phe  Ser  Phe  Phe  Pro  Glu  Ile  Thr  His  Ile  Val  Ile  Lys  Glu  Ser
     355                      360                      365

GTG  GTC  AGC  ATT  AAC  AAG  CAG  GAC  AAC  AAG  AAA  ATG  GAA  CTG  AAG                1339
Val  Val  Ser  Ile  Asn  Lys  Gln  Asp  Asn  Lys  Lys  Met  Glu  Leu  Lys
     370                      375                      380

CTC  TCT  TCC  CAC  GAG  GAG  GCC  TTG  TCC  TTT  GTG  TCC  CTG  GTA  GAT                1384
Leu  Ser  Ser  His  Glu  Glu  Ala  Leu  Ser  Phe  Val  Ser  Leu  Val  Asp
     385                      390                      395

GGC  TAC  TTC  CGG  CTC  ACA  GCA  GAT  GCC  CAT  CAT  TAC  CTC  TGC  ACC                1429
Gly  Tyr  Phe  Arg  Leu  Thr  Ala  Asp  Ala  His  His  Tyr  Leu  Cys  Thr
     400                      405                      410

GAC  GTG  GCC  CCC  CCG  TTG  ATC  GTC  CAC  AAC  ATA  CAG  AAT  GGC  TGT                1474
Asp  Val  Ala  Pro  Pro  Leu  Ile  Val  His  Asn  Ile  Gln  Asn  Gly  Cys
     415                      420                      425

CAT  GGT  CCA  ATC  TGT  ACA  GAA  TAC  GCC  ATC  AAT  AAA  TTG  CGG  CAA                1519
His  Gly  Pro  Ile  Cys  Thr  Glu  Tyr  Ala  Ile  Asn  Lys  Leu  Arg  Gln
     430                      435                      440

GAA  GGA  AGC  GAG  GAG  GGG  ATG  TAC  GTG  CTG  AGG  TGG  AGC  TGC  ACC                1564
Glu  Gly  Ser  Glu  Glu  Gly  Met  Tyr  Val  Leu  Arg  Trp  Ser  Cys  Thr
     445                      450                      455

GAC  TTT  GAC  AAC  ATC  CTC  ATG  ACC  GTC  ACC  TGC  TTT  GAG  AAG  TCT                1609
Asp  Phe  Asp  Asn  Ile  Leu  Met  Thr  Val  Thr  Cys  Phe  Glu  Lys  Ser
     460                      465                      470

GAG  CAG  GTG  CAG  GGT  GCC  CAG  AAG  CAG  TTC  AAG  AAC  TTT  CAG  ATC                1654
Glu  Gln  Val  Gln  Gly  Ala  Gln  Lys  Gln  Phe  Lys  Asn  Phe  Gln  Ile
     475                      480                      485

GAG  GTG  CAG  AAG  GGC  CGC  TAC  AGT  CTG  CAC  GGT  TCG  GAC  CGC  AGC                1699
Glu  Val  Gln  Lys  Gly  Arg  Tyr  Ser  Leu  His  Gly  Ser  Asp  Arg  Ser
     490                      495                      500

TTC  CCC  AGC  TTG  GGA  GAC  CTC  ATG  AGC  CAC  CTC  AAG  AAG  CAG  ATC                1744
Phe  Pro  Ser  Leu  Gly  Asp  Leu  Met  Ser  His  Leu  Lys  Lys  Gln  Ile
     505                      510                      515

CTG  CGC  ACG  GAT  AAC  ATC  AGC  TTC  ATG  CTA  AAA  CGC  TGC  TGC  CAG                1789
Leu  Arg  Thr  Asp  Asn  Ile  Ser  Phe  Met  Leu  Lys  Arg  Cys  Cys  Gln
     520                      525                      530

CCC  AAG  CCC  CGA  GAA  ATC  TCC  AAC  CTG  CTG  GTG  GCT  ACT  AAG  AAA                1834
Pro  Lys  Pro  Arg  Glu  Ile  Ser  Asn  Leu  Leu  Val  Ala  Thr  Lys  Lys
     535                      540                      545

GCC  CAG  GAG  TGG  CAG  CCC  GTC  TAC  CCC  ATG  AGC  CAG  CTG  AGT  TTC                1879
Ala  Gln  Glu  Trp  Gln  Pro  Val  Tyr  Pro  Met  Ser  Gln  Leu  Ser  Phe
     550                      555                      560

GAT  CGG  ATC  CTC  AAG  AAG  GAT  CTG  GTG  CAG  GGC  GAG  CAC  CTT  GGG                1924
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Asp | Arg | Ile | Leu | Lys | Lys | Asp | Leu | Val | Gln | Gly | Glu | His | Leu | Gly |      |
|     | 565 |     |     |     | 570 |     |     |     |     | 575 |     |     |     |     |      |
| AGA | GGC | ACG | AGA | ACA | CAC | ATC | TAT | TCT | GGG | ACC | CTG | ATG | GAT | TAC | 1969 |
| Arg | Gly | Thr | Arg | Thr | His | Ile | Tyr | Ser | Gly | Thr | Leu | Met | Asp | Tyr |      |
|     | 580 |     |     |     | 585 |     |     |     |     | 590 |     |     |     |     |      |
| AAG | GAT | GAC | GAA | GGA | ACT | TCT | GAA | GAG | AAG | AAG | ATA | AAA | GTG | ATC | 2014 |
| Lys | Asp | Asp | Glu | Gly | Thr | Ser | Glu | Glu | Lys | Lys | Ile | Lys | Val | Ile |      |
|     | 595 |     |     |     | 600 |     |     |     |     | 605 |     |     |     |     |      |
| CTC | AAA | GTC | TTA | GAC | CCC | AGC | CAC | AGG | GAT | ATT | TCC | CTG | GCC | TTC | 2059 |
| Leu | Lys | Val | Leu | Asp | Pro | Ser | His | Arg | Asp | Ile | Ser | Leu | Ala | Phe |      |
|     | 605 |     |     |     | 615 |     |     |     |     | 620 |     |     |     |     |      |
| TTC | GAG | GCA | GCC | AGC | ATG | ATG | AGA | CAG | GTC | TCC | CAC | AAA | CAC | ATC | 2104 |
| Phe | Glu | Ala | Ala | Ser | Met | Met | Arg | Gln | Val | Ser | His | Lys | His | Ile |      |
|     | 625 |     |     |     | 630 |     |     |     |     | 635 |     |     |     |     |      |
| GTG | TAC | CTC | TAT | GGC | GTC | TGT | GTC | CGC | GAC | GTG | GAG | AAT | ATC | ATG | 2149 |
| Val | Tyr | Leu | Tyr | Gly | Val | Cys | Val | Arg | Asp | Val | Glu | Asn | Ile | Met |      |
|     | 640 |     |     |     | 645 |     |     |     |     | 650 |     |     |     |     |      |
| GTG | GAA | GAG | TTT | GTG | GAA | GGG | GGT | CCT | CTG | GAT | CTC | TTC | ATG | CAC | 2194 |
| Val | Glu | Glu | Phe | Val | Glu | Gly | Gly | Pro | Leu | Asp | Leu | Phe | Met | His |      |
|     | 655 |     |     |     | 660 |     |     |     |     | 665 |     |     |     |     |      |
| CGG | AAA | AGT | GAT | GTC | CTT | ACC | ACA | CCA | TGG | AAA | TTC | AAA | GTT | GCC | 2239 |
| Arg | Lys | Ser | Asp | Val | Leu | Thr | Thr | Pro | Trp | Lys | Phe | Lys | Val | Ala |      |
|     | 670 |     |     |     | 675 |     |     |     |     | 680 |     |     |     |     |      |
| AAA | CAG | CTG | GCC | AGT | GCC | CTG | AGC | TAC | TTG | GAG | GAT | AAA | GAC | CTG | 2284 |
| Lys | Gln | Leu | Ala | Ser | Ala | Leu | Ser | Tyr | Leu | Glu | Asp | Lys | Asp | Leu |      |
|     | 685 |     |     |     | 690 |     |     |     |     | 695 |     |     |     |     |      |
| GTC | CAT | GGA | AAT | GTG | TGT | ACT | AAA | AAC | CTC | CTC | CTG | GCC | CGT | GAG | 2329 |
| Val | His | Gly | Asn | Val | Cys | Thr | Lys | Asn | Leu | Leu | Leu | Ala | Arg | Glu |      |
|     | 700 |     |     |     | 705 |     |     |     |     | 710 |     |     |     |     |      |
| GGA | ATC | GAC | AGT | GAG | TGT | GGC | CCA | TTC | ATC | AAG | CTC | AGT | GAC | CCC | 2374 |
| Gly | Ile | Asp | Ser | Glu | Cys | Gly | Pro | Phe | Ile | Lys | Leu | Ser | Asp | Pro |      |
|     | 715 |     |     |     | 720 |     |     |     |     | 725 |     |     |     |     |      |
| GGC | ATC | CCC | ATT | ACG | GTG | CTG | TCT | AGG | CAA | GAA | TGC | ATT | GAA | CGA | 2419 |
| Gly | Ile | Pro | Ile | Thr | Val | Leu | Ser | Arg | Gln | Glu | Cys | Ile | Glu | Arg |      |
|     | 730 |     |     |     | 735 |     |     |     |     | 740 |     |     |     |     |      |
| ATC | CCA | TGG | ATT | GCT | CCT | GAG | TGT | GTT | GAG | GAC | TCC | AAG | AAC | CTG | 2464 |
| Ile | Pro | Trp | Ile | Ala | Pro | Glu | Cys | Val | Glu | Asp | Ser | Lys | Asn | Leu |      |
|     | 745 |     |     |     | 750 |     |     |     |     | 755 |     |     |     |     |      |
| AGT | GTG | GCT | GCT | GAC | AAG | TGG | AGC | TTT | GGA | ACC | ACG | CTC | TGG | GAA | 2509 |
| Ser | Val | Ala | Ala | Asp | Lys | Trp | Ser | Phe | Gly | Thr | Thr | Leu | Trp | Glu |      |
|     | 760 |     |     |     | 765 |     |     |     |     | 770 |     |     |     |     |      |
| ATC | TGC | TAC | AAT | GGC | GAG | ATC | CCC | TTG | AAA | GAC | AAG | ACG | CTG | ATT | 2554 |
| Ile | Cys | Tyr | Asn | Gly | Glu | Ile | Pro | Leu | Lys | Asp | Lys | Thr | Leu | Ile |      |
|     | 775 |     |     |     | 780 |     |     |     |     | 785 |     |     |     |     |      |
| GAG | AAA | GAG | AGA | TTC | TAT | GAA | AGC | CGG | TGC | AGG | CCA | GTG | ACA | CCA | 2599 |
| Glu | Lys | Glu | Arg | Phe | Tyr | Glu | Ser | Arg | Cys | Arg | Pro | Val | Thr | Pro |      |
|     | 790 |     |     |     | 795 |     |     |     |     | 800 |     |     |     |     |      |
| TCA | TGT | AAG | GAG | CTG | GCT | GAC | CTC | ATG | ACC | CGC | TGC | ATG | AAC | TAT | 2644 |
| Ser | Cys | Lys | Glu | Leu | Ala | Asp | Leu | Met | Thr | Arg | Cys | Met | Asn | Tyr |      |
|     | 805 |     |     |     | 810 |     |     |     |     | 815 |     |     |     |     |      |
| GAC | CCC | AAT | CAG | AGG | CCT | TTC | TTC | CGA | GCC | ATC | ATG | AGA | GAC | ATT | 2689 |
| Asp | Pro | Asn | Gln | Arg | Pro | Phe | Phe | Arg | Ala | Ile | Met | Arg | Asp | Ile |      |
|     | 820 |     |     |     | 825 |     |     |     |     | 830 |     |     |     |     |      |
| AAT | AAG | CTT | GAA | GAG | CAG | AAT | CCA | GAT | ATT | GTT | TCC | AGA | AAA | AAA | 2734 |
| Asn | Lys | Leu | Glu | Glu | Gln | Asn | Pro | Asp | Ile | Val | Ser | Arg | Lys | Lys |      |
|     | 835 |     |     |     | 840 |     |     |     |     | 845 |     |     |     |     |      |
| AAC | CAG | CCA | ACT | GAA | GTG | GAC | CCC | ACA | CAT | TTT | GAG | AAG | CGC | TTC | 2779 |
| Asn | Gln | Pro | Thr | Glu | Val | Asp | Pro | Thr | His | Phe | Glu | Lys | Arg | Phe |      |
|     | 850 |     |     |     | 855 |     |     |     |     | 860 |     |     |     |     |      |
| CTA | AAG | AGG | ATC | CGT | GAC | TTG | GGA | GAG | GGC | CAC | TTT | GGG | AAG | GTT | 2824 |

| | | | | | | | | | | | | | | |
|---|---|---|---|---|---|---|---|---|---|---|---|---|---|---|
|Leu|Lys|Arg|Ile|Arg|Asp|Leu|Gly|Glu|Gly|His|Phe|Gly|Lys|Val|
| |865| | | | |870| | | | |875| | | |

| | | | | | | | | | | | | | | | |
|---|---|---|---|---|---|---|---|---|---|---|---|---|---|---|---|
|GAG|CTC|TGC|AGG|TAT|GAC|CCC|GAA|GAC|AAT|ACA|GGG|GAG|CAG|GTG|2869|
|Glu|Leu|Cys|Arg|Tyr|Asp|Pro|Glu|Asp|Asn|Thr|Gly|Glu|Gln|Val| |
| |880| | | | |885| | | | |890| | | | |

|GCT|GTT|AAA|TCT|CTG|AAG|CCT|GAG|AGT|GGA|GGT|AAC|CAC|ATA|GCT|2914|
|---|---|---|---|---|---|---|---|---|---|---|---|---|---|---|---|
|Ala|Val|Lys|Ser|Leu|Lys|Pro|Glu|Ser|Gly|Gly|Asn|His|Ile|Ala| |
| |895| | | | |900| | | | |905| | | | |

|GAT|CTG|AAA|AAG|GAA|ATC|GAG|ATC|TTA|AGG|AAC|CTC|TAT|CAT|GAG|2959|
|---|---|---|---|---|---|---|---|---|---|---|---|---|---|---|---|
|Asp|Leu|Lys|Lys|Glu|Ile|Glu|Ile|Leu|Arg|Asn|Leu|Tyr|His|Glu| |
| |910| | | | |915| | | | |920| | | | |

|AAC|ATT|GTG|AAG|TAC|AAA|GGA|ATC|TGC|ACA|GAA|GAC|GGA|GGA|AAT|3004|
|---|---|---|---|---|---|---|---|---|---|---|---|---|---|---|---|
|Asn|Ile|Val|Lys|Tyr|Lys|Gly|Ile|Cys|Thr|Glu|Asp|Gly|Gly|Asn| |
| |925| | | | |930| | | | |935| | | | |

|GGT|ATT|AAG|CTC|ATC|ATG|GAA|TTT|CTG|CCT|TCG|GGA|AGC|CTT|AAG|3049|
|---|---|---|---|---|---|---|---|---|---|---|---|---|---|---|---|
|Gly|Ile|Lys|Leu|Ile|Met|Glu|Phe|Leu|Pro|Ser|Gly|Ser|Leu|Lys| |
| |940| | | | |945| | | | |950| | | | |

|GAA|TAT|CTT|CCA|AAG|AAT|AAG|AAC|AAA|ATA|AAC|CTC|AAA|CAG|CAG|3094|
|---|---|---|---|---|---|---|---|---|---|---|---|---|---|---|---|
|Glu|Tyr|Leu|Pro|Lys|Asn|Lys|Asn|Lys|Ile|Asn|Leu|Lys|Gln|Gln| |
| |955| | | | |960| | | | |965| | | | |

|CTA|AAA|TAT|GCC|GTT|CAG|ATT|TGT|AAG|GGG|ATG|GAC|TAT|TTG|GGT|3139|
|---|---|---|---|---|---|---|---|---|---|---|---|---|---|---|---|
|Leu|Lys|Tyr|Ala|Val|Gln|Ile|Cys|Lys|Gly|Met|Asp|Tyr|Leu|Gly| |
| |970| | | | |975| | | | |980| | | | |

|TCT|CGG|CAA|TAC|GTT|CAC|CGG|GAC|TTG|GCA|GCA|AGA|AAT|GTC|CTT|3184|
|---|---|---|---|---|---|---|---|---|---|---|---|---|---|---|---|
|Ser|Arg|Gln|Tyr|Val|His|Arg|Asp|Leu|Ala|Ala|Arg|Asn|Val|Leu| |
| |985| | | | |990| | | | |995| | | | |

|GTT|GAG|AGT|GAA|CAC|CAA|GTG|AAA|ATT|GGA|GAC|TTC|GGT|TTA|ACC|3229|
|---|---|---|---|---|---|---|---|---|---|---|---|---|---|---|---|
|Val|Glu|Ser|Glu|His|Gln|Val|Lys|Ile|Gly|Asp|Phe|Gly|Leu|Thr| |
| |1000| | | | |1005| | | | |1010| | | | |

|AAA|GCA|ATT|GAA|ACC|GAT|AAG|GAG|TAT|TAC|ACC|GTC|AAG|GAT|GAC|3274|
|---|---|---|---|---|---|---|---|---|---|---|---|---|---|---|---|
|Lys|Ala|Ile|Glu|Thr|Asp|Lys|Glu|Tyr|Tyr|Thr|Val|Lys|Asp|Asp| |
| |1015| | | | |1020| | | | |1025| | | | |

|CGG|GAC|AGC|CCT|GTG|TTT|TGG|TAT|GCT|CCA|GAA|TGT|TTA|ATG|CAA|3319|
|---|---|---|---|---|---|---|---|---|---|---|---|---|---|---|---|
|Arg|Asp|Ser|Pro|Val|Phe|Trp|Tyr|Ala|Pro|Glu|Cys|Leu|Met|Gln| |
| |1030| | | | |1035| | | | |1040| | | | |

|TCT|AAA|TTT|TAT|ATT|GCC|TCT|GAC|GTC|TGG|TCT|TTT|GGA|GTC|ACT|3364|
|---|---|---|---|---|---|---|---|---|---|---|---|---|---|---|---|
|Ser|Lys|Phe|Tyr|Ile|Ala|Ser|Asp|Val|Trp|Ser|Phe|Gly|Val|Thr| |
| |1045| | | | |1050| | | | |1055| | | | |

|CTG|CAT|GAG|CTG|CTG|ACT|TAC|TGT|GAT|TCA|GAT|TCT|AGT|CCC|ATG|3409|
|---|---|---|---|---|---|---|---|---|---|---|---|---|---|---|---|
|Leu|His|Glu|Leu|Leu|Thr|Tyr|Cys|Asp|Ser|Asp|Ser|Ser|Pro|Met| |
| |1060| | | | |1065| | | | |1070| | | | |

|GCT|TTG|TTC|CTG|AAA|ATG|ATA|GGC|CCA|ACC|CAT|GGC|CAG|ATG|ACA|3454|
|---|---|---|---|---|---|---|---|---|---|---|---|---|---|---|---|
|Ala|Leu|Phe|Leu|Lys|Met|Ile|Gly|Pro|Thr|His|Gly|Gln|Met|Thr| |
| |1075| | | | |1080| | | | |1085| | | | |

|GTC|ACA|AGA|CTT|GTG|AAT|ACG|TTA|AAA|GAA|GGA|AAA|CGC|CTG|CCG|3499|
|---|---|---|---|---|---|---|---|---|---|---|---|---|---|---|---|
|Val|Thr|Arg|Leu|Val|Asn|Thr|Leu|Lys|Glu|Gly|Lys|Arg|Leu|Pro| |
| |1090| | | | |1095| | | | |1100| | | | |

|TGC|CCA|CCT|AAC|TGT|CCA|GAT|GAG|GTT|TAT|CAG|CTT|ATG|AGA|AAA|3544|
|---|---|---|---|---|---|---|---|---|---|---|---|---|---|---|---|
|Cys|Pro|Pro|Asn|Cys|Pro|Asp|Glu|Val|Tyr|Gln|Leu|Met|Arg|Lys| |
| |1105| | | | |1110| | | | |1115| | | | |

|TGC|TGG|GAA|TTC|CAA|CCA|TCC|AAT|CGG|ACA|AGC|TTT|CAG|AAC|CTT|3589|
|---|---|---|---|---|---|---|---|---|---|---|---|---|---|---|---|
|Cys|Trp|Glu|Phe|Gln|Pro|Ser|Asn|Arg|Thr|Ser|Phe|Gln|Asn|Leu| |
| |1120| | | | |1135| | | | |1130| | | | |

|ATT|GAA|GGA|TTT|GAA|GCA|CTT|TTA|AAA|TAAGAAGCAT|GAATAACATT| | | | |3636|
|---|---|---|---|---|---|---|---|---|---|---|---|---|---|---|---|
|Ile|Glu|Gly|Phe|Glu|Ala|Leu|Leu|Lys| | | | | | | |
| |1135| | | | |1140| | | | | | | | | |

| | | | | |
|---|---|---|---|---|
|TAAATTCCAC|AGATTATCAA|GTCCTTCTCC|TGCAACAAAT|GCCCAAGTCA|TTTTTTAAAA|3696|
|ATTTCTAATG|AAAGAAGTTT|GTGTTCTGTC|CAAAAAGTCA|CTGAACTCAT|ACTTCAGTAC|3756|
|ATATACATGT|ATAAGGCACA|CTGTAGTGCT|TAATATGTGT|AAGGACTTCC|TCTTTAAATT|3816|

| | | | | | | | | | | | | |
|---|---|---|---|---|---|---|---|---|---|---|---|---|
| TGCACCAGTA | ACTTAGTGAC | ACATAATGAC | AACCAAAATA | TTTGAAAGCA | CTTAAGCACT | 3876 |
| CCTCCTTGTG | GAAAGAATAT | ACCACCATTT | CATCTGGCTA | GTTCACCATC | ACAACTGCAT | 3936 |
| TACCAAAAGG | GGATTTTTGA | AAACGAGGAG | TTGACCAAAA | TAATATCTGA | AGATGATTGC | 3996 |
| TTTTCCCTGC | TGCCAGCTGA | CTGAAATGTT | TTCCTGGCAC | ATTAATCATA | GATAAAGAAG | 4056 |
| ATTGATGGAC | TTAGCCCTCA | AACAGTATCT | ATACAGTACT | AGACCATGCA | TTCTTAAAAT | 4116 |
| ATTAGATACC | AGGTAGTATA | TATTGTTTCT | GTACAAAAAT | GACTGTATTC | TCTCACCAGT | 4176 |
| AGGACTTAAA | CTTTGTTTCT | CCAGTGGCTT | AGCTCCTGTT | CCTTTGGGTG | ATCACTAG | 4234 |

( 2 ) INFORMATION FOR SEQ ID NO:2:

( i ) SEQUENCE CHARACTERISTICS:
        ( A ) LENGTH: 3495 base pairs
        ( B ) TYPE: nucleic acid
        ( D ) STRANDEDNESS: single
        ( D ) TOPOLOGY: linear ( i i ) MOLECULE TYPE: nucleic acid ( x i ) SEQUENCE DESCRIPTION: SEQ ID NO: 2:

```
CTG   CTT   GAT   GAC   TTT   GTC   ATG   TCT   TAC   CTT   TCC   CCT   CAG   TGG   CGG         45
Leu   Leu   Asp   Asp   Phe   Val   Met   Ser   Tyr   Leu   Ser   Pro   Gln   Trp   Arg
 1                       5                         10                        15

CAT   GAT   TTT   GTT   CAC   GGA   TGG   ATA   AAA   GTA   CCT   GTG   ACT   CAT   GAA         90
His   Asp   Phe   Val   His   Gly   Trp   Ile   Lys   Val   Pro   Val   Thr   His   Glu
                        20                        25                        30

ACT   CAG   GAA   GAG   TGT   CTT   GGG   ATG   GCG   GTG   TTA   GAC   ATG   ATG   AGA        135
Thr   Gln   Glu   Glu   Cys   Leu   Gly   Met   Ala   Val   Leu   Asp   Met   Met   Arg
                        35                        40                        45

ATA   GCT   AAG   GAG   AAA   GAC   CAG   ACT   CCA   CTG   GCT   GTC   TAT   AAC   TCT        180
Ile   Ala   Lys   Glu   Lys   Asp   Gln   Thr   Pro   Leu   Ala   Val   Tyr   Asn   Ser
                        50                        55                        60

GTC   AGC   TAC   AAG   ACA   TTC   TTA   CCA   AAG   TGC   GTT   CGA   GCG   AAG   ATC        225
Val   Ser   Tyr   Lys   Thr   Phe   Leu   Pro   Lys   Cys   Val   Arg   Ala   Lys   Ile
                        65                        70                        75

CAA   GAC   TAT   CAC   ATT   TTA   ACC   CGG   AAG   CGA   ATC   AGG   TAC   AGA   TTT        270
Gln   Asp   Tyr   His   Ile   Leu   Thr   Arg   Lys   Arg   Ile   Arg   Tyr   Arg   Phe
                        80                        85                        90

CGC   AGA   TTC   ATT   CAG   CAA   TTC   AGT   CAA   TGT   AAA   GCC   ACT   GCC   AGG        315
Arg   Arg   Phe   Ile   Gln   Gln   Phe   Ser   Gln   Cys   Lys   Ala   Thr   Ala   Arg
                        95                       100                       105

AAC   CTA   AAA   CTT   AAG   TAT   CTT   ATA   AAC   CTG   GAA   ACC   CTG   CAG   TCT        360
Asn   Leu   Lys   Leu   Lys   Tyr   Leu   Ile   Asn   Leu   Glu   Thr   Leu   Gln   Ser
                       110                       115                       120

GCC   TTC   TAC   ACA   GAA   CAG   TTT   GAA   GTA   AAA   GAA   TCT   GCA   AGA   GGT        405
Ala   Phe   Tyr   Thr   Glu   Gln   Phe   Glu   Val   Lys   Glu   Ser   Ala   Arg   Gly
                       125                       130                       135

CCT   TCA   GGT   GAG   GAG   ATT   TTT   GCA   ACC   ATT   ATA   ATA   ACT   GGA   AAC        450
Pro   Ser   Gly   Glu   Glu   Ile   Phe   Ala   Thr   Ile   Ile   Ile   Thr   Gly   Asn
                       140                       145                       150

GGT   GGA   ATT   CAG   TGG   TCA   AGA   GGG   AAA   CAT   AAG   GAA   AGT   GAG   ACA        495
Gly   Gly   Ile   Gln   Trp   Ser   Arg   Gly   Lys   His   Lys   Glu   Ser   Glu   Thr
                       155                       160                       165

CTG   ACA   GAA   CAG   GAC   GTA   CAG   TTA   TAT   TGT   GAT   TTC   CCT   GAT   ATT        540
Leu   Thr   Glu   Gln   Asp   Val   Gln   Leu   Tyr   Cys   Asp   Phe   Pro   Asp   Ile
                       170                       175                       180

ATT   GAT   GTC   AGT   ATT   AAG   CAA   GCA   AAT   CAG   GAA   TGC   TCA   ACT   GAA        585
Ile   Asp   Val   Ser   Ile   Lys   Gln   Ala   Asn   Gln   Glu   Cys   Ser   Thr   Glu
                       185                       190                       195
```

| | | | | | | | | | | | | | | | |
|---|---|---|---|---|---|---|---|---|---|---|---|---|---|---|---|
| AGT | AGA | GTT | GTG | ACC | GTC | CAC | AAG | CAG | GAC | GGG | AAG | GTC | TTG | GAA | 630 |
| Ser | Arg | Val | Val | Thr 200 | Val | His | Lys | Gln 205 | Asp | Gly | Lys | Val | Leu | Glu 210 | |
| ATA | GAA | CTT | AGC | TCA | TTA | AAA | GAA | GCC | TTG | TCA | TTC | GTG | TCA | TTA | 675 |
| Ile | Glu | Leu | Ser | Ser 215 | Leu | Lys | Glu | Ala 220 | Leu | Ser | Phe | Val | Ser | Leu 225 | |
| ATT | GAC | GGG | TAT | TAC | AGA | CTA | ACT | GCG | GAT | GCA | CAC | CAT | TAC | CTC | 720 |
| Ile | Asp | Gly | Tyr | Tyr 230 | Arg | Leu | Thr | Ala 235 | Asp | Ala | His | His | Tyr | Leu 240 | |
| TGC | AAA | GAG | GTG | GCT | CCC | CCA | GCT | GTG | TTC | GAG | AAC | ATA | CAC | AGC | 765 |
| Cys | Lys | Glu | Val | Ala 245 | Pro | Pro | Ala | Val 250 | Phe | Glu | Asn | Ile | His | Ser 255 | |
| AAC | TGC | CAC | GGC | CCA | ATT | TCA | ATG | GAT | TTT | GCC | ATC | AGC | AAA | CTA | 810 |
| Asn | Cys | His | Gly | Pro 260 | Ile | Ser | Met | Asp 265 | Phe | Ala | Ile | Ser | Lys | Leu 270 | |
| AAG | AAG | GCA | GGA | AAC | CAG | ACT | GGA | CTG | TAT | GTA | CTT | CGA | TGT | AGC | 855 |
| Lys | Lys | Ala | Gly | Asn 275 | Gln | Thr | Gly | Leu 280 | Tyr | Val | Leu | Arg | Cys | Ser 285 | |
| CCT | AAG | GAC | TTC | AAC | AAA | TAC | TTC | CTG | ACC | TTT | GCC | GTT | GAG | CGA | 900 |
| Pro | Lys | Asp | Phe | Asn 290 | Lys | Tyr | Phe | Leu 295 | Thr | Phe | Ala | Val | Glu | Arg 300 | |
| GAA | AAT | GTT | ATT | GAA | TAT | AAA | CAC | TGT | TTG | ATT | ACA | AAG | AAT | GAG | 945 |
| Glu | Asn | Val | Ile | Glu 305 | Tyr | Lys | His | Cys 310 | Leu | Ile | Thr | Lys | Asn | Glu 315 | |
| AAT | GGA | GAG | TAC | AAC | CTC | AGT | GGG | ACT | AAG | AGG | AAC | TTC | AGT | AGT | 990 |
| Asn | Gly | Glu | Tyr | Asn 320 | Leu | Ser | Gly | Thr 325 | Lys | Arg | Asn | Phe | Ser | Ser 330 | |
| CTT | AAG | GAC | CTT | TTG | AAT | TGC | TAC | CAG | ATG | GAA | ACT | GTG | CGC | TCA | 1035 |
| Leu | Lys | Asp | Leu | Leu 335 | Asn | Cys | Tyr | Gln 340 | Met | Glu | Thr | Val | Arg | Ser 345 | |
| GAC | AGT | ATC | ATC | TTC | CAG | TTC | ACC | AAA | TGC | TGT | CCT | CCA | AAG | CCG | 1080 |
| Asp | Ser | Ile | Ile | Phe 350 | Gln | Phe | Thr | Lys 355 | Cys | Cys | Pro | Pro | Lys | Pro 360 | |
| AAA | GAT | AAA | TCA | AAC | CTT | CTT | GTC | TTC | AGA | ACA | AAT | GGT | GTT | TCT | 1125 |
| Lys | Asp | Lys | Ser | Asn 365 | Leu | Leu | Val | Phe 370 | Arg | Thr | Asn | Gly | Val | Ser 375 | |
| GAT | GTT | CAG | CTC | TCA | CCA | ACA | TTA | CAG | AGG | CAT | AAT | AAT | GTG | AAT | 1170 |
| Asp | Val | Gln | Leu | Ser 380 | Pro | Thr | Leu | Gln 385 | Arg | His | Asn | Asn | Val | Asn 390 | |
| CAA | ATG | GTG | TTT | CAC | AAA | ATC | AGG | AAT | GAA | GAT | TTG | ATA | TTT | AAT | 1215 |
| Gln | Met | Val | Phe | His 395 | Lys | Ile | Arg | Asn 400 | Glu | Asp | Leu | Ile | Phe | Asn 405 | |
| GAA | AGC | CTT | GGC | CAA | GGC | ACT | TTT | ACA | AAA | ATA | TTT | AAA | GGT | GTA | 1260 |
| Glu | Ser | Leu | Gly | Gln 410 | Gly | Thr | Phe | Thr 415 | Lys | Ile | Phe | Lys | Gly | Val 420 | |
| AGA | AGA | GAA | GTT | GGA | GAT | TAT | GGT | CAG | CTG | CAC | GAA | ACC | GAA | GTT | 1305 |
| Arg | Arg | Glu | Val | Gly 425 | Asp | Tyr | Gly | Gln 430 | Leu | His | Glu | Thr | Glu | Val 435 | |
| CTT | TTG | AAA | GTC | CTA | GAT | AAA | GCA | CAT | AGA | AAC | TAT | TCA | GAG | TCT | 1350 |
| Leu | Leu | Lys | Val | Leu 440 | Asp | Lys | Ala | His 445 | Arg | Asn | Tyr | Ser | Glu | Ser 450 | |
| TTC | TTT | GAA | GCA | GCA | AGC | ATG | ATG | AGT | CAG | CTT | TCT | CAC | AAG | CAT | 1395 |
| Phe | Phe | Glu | Ala | Ala 455 | Ser | Met | Met | Ser 460 | Gln | Leu | Ser | His | Lys | His 465 | |
| TTG | GTT | TTG | AAT | TAT | GGA | GTA | TGT | GTC | TGT | GGA | GAG | GAG | AAC | ATT | 1440 |
| Leu | Val | Leu | Asn | Tyr 470 | Gly | Val | Cys | Val 475 | Cys | Gly | Glu | Glu | Asn | Ile 480 | |
| TTG | GTT | CAA | GAG | TTT | GTA | AAA | TTT | GGA | TCA | CTG | GAT | ACA | TAC | CTG | 1485 |
| Leu | Val | Gln | Glu | Phe 485 | Val | Lys | Phe | Gly 490 | Ser | Leu | Asp | Thr | Tyr | Leu 495 | |

```
AAG  AAG  AAC  AAA  AAT  TCT  ATA  AAT  ATA  TTA  TGG  AAA  CTT  GGA  GTG         1530
Lys  Lys  Asn  Lys  Asn  Ser  Ile  Asn  Ile  Leu  Trp  Lys  Leu  Gly  Val
               500                 505                      510

GCG  AAG  CAG  TTG  GCA  TGG  GCC  ATG  CAC  TTC  CTC  GAA  GAA  AAA  TCC         1575
Ala  Lys  Gln  Leu  Ala  Trp  Ala  Met  His  Phe  Leu  Glu  Glu  Lys  Ser
               515                 520                      525

CTT  ATT  CAT  GGG  AAT  GTG  TGT  GCT  AAA  AAT  ATC  CTG  CTT  ATC  AGA         1620
Leu  Ile  His  Gly  Asn  Val  Cys  Ala  Lys  Asn  Ile  Leu  Leu  Ile  Arg
               530                 535                      540

GAA  GAA  GAC  AGG  AGA  ACG  GGG  AAC  CCA  CCT  TTC  ATC  AAA  CTT  AGT         1665
Glu  Glu  Asp  Arg  Arg  Thr  Gly  Asn  Pro  Pro  Phe  Ile  Lys  Leu  Ser
               545                 550                      555

GAT  CCT  GGC  ATT  AGC  ATT  ACA  GTT  CTA  CCG  AAG  GAC  ATT  TCT  TCC         1710
Asp  Pro  Gly  Ile  Ser  Ile  Thr  Val  Leu  Pro  Lys  Asp  Ile  Ser  Ser
               560                 565                      570

TGT  TGT  TTC  CAA  GTT  CTT  CAG  GAG  AGA  ATA  CCA  TGG  GTA  CCA  CCT         1755
Cys  Cys  Phe  Gln  Val  Leu  Gln  Glu  Arg  Ile  Pro  Trp  Val  Pro  Pro
               575                 580                      585

GAG  TGC  ATT  GAG  AAT  CCT  AAA  AAT  CTA  ACT  CTG  GCA  ACA  GAC  AAG         1800
Glu  Cys  Ile  Glu  Asn  Pro  Lys  Asn  Leu  Thr  Leu  Ala  Thr  Asp  Lys
               590                 595                      600

TGG  AGC  TTC  GGG  ACC  ACT  CTG  TGG  GAG  ATC  TGC  AGT  GGA  GGA  GAT         1845
Trp  Ser  Phe  Gly  Thr  Thr  Leu  Trp  Glu  Ile  Cys  Ser  Gly  Gly  Asp
               605                 610                      615

AAG  CCC  CTG  AGT  GCT  CTG  GAT  TCT  CAA  AGA  AAG  CTG  CAG  TTC  TAT         1890
Lys  Pro  Leu  Ser  Ala  Leu  Asp  Ser  Gln  Arg  Lys  Leu  Gln  Phe  Tyr
               620                 625                      630

GAA  GAT  AAG  CAT  CAG  CTT  CCT  GCA  CCC  AAG  TGG  ACA  GAG  TTG  GCA         1935
Glu  Asp  Lys  His  Gln  Leu  Pro  Ala  Pro  Lys  Trp  Thr  Glu  Leu  Ala
               635                 640                      645

AAC  CTT  ATA  AAT  AAT  TGC  ATG  GAC  TAT  GAG  CCA  GAT  TTC  AGG  CCT         1980
Asn  Leu  Ile  Asn  Asn  Cys  Met  Asp  Tyr  Glu  Pro  Asp  Phe  Arg  Pro
               650                 655                      660

GCT  TTC  AGA  GCT  GTC  ATC  CGT  GAT  CTT  AAC  AGC  CTG  TTT  ACT  CCA         2025
Ala  Phe  Arg  Ala  Val  Ile  Arg  Asp  Leu  Asn  Ser  Leu  Phe  Thr  Pro
               665                 670                      675

GAT  TAT  GAA  CTA  CTA  ACA  GAA  AAT  GAC  ATG  CTA  CCA  AAC  ATG  AGA         2070
Asp  Tyr  Glu  Leu  Leu  Thr  Glu  Asn  Asp  Met  Leu  Pro  Asn  Met  Arg
               680                 685                      690

ATA  GGT  GCC  CTA  GGG  TTT  TCT  GGT  GCT  TTT  GAA  GAC  AGG  GAC  CCT         2115
Ile  Gly  Ala  Leu  Gly  Phe  Ser  Gly  Ala  Phe  Glu  Asp  Arg  Asp  Pro
               695                 700                      705

ACA  CAG  TTT  GAA  GAG  AGA  CAC  TTG  AAG  TTT  CTA  CAG  CAG  CTT  GGC         2160
Thr  Gln  Phe  Glu  Glu  Arg  His  Leu  Lys  Phe  Leu  Gln  Gln  Leu  Gly
               710                 715                      720

AAA  GGT  AAC  TTC  GGG  AGT  GTG  GAG  ATG  TGC  CGC  TAT  GAC  CCG  CTG         2205
Lys  Gly  Asn  Phe  Gly  Ser  Val  Glu  Met  Cys  Arg  Tyr  Asp  Pro  Leu
               725                 730                      735

CAG  GAC  AAC  ACT  GGC  GAG  GTG  GTC  GCT  GTG  AAG  AAA  CTC  CAG  CAC         2250
Gln  Asp  Asn  Thr  Gly  Glu  Val  Val  Ala  Val  Lys  Lys  Leu  Gln  His
               740                 745                      750

AGC  ACT  GAA  GAG  CAC  CTC  CGA  GAC  TTT  GAG  AGG  GAG  ATC  GAG  ATC         2295
Ser  Thr  Glu  Glu  His  Leu  Arg  Asp  Phe  Glu  Arg  Glu  Ile  Glu  Ile
               755                 760                      765

CTG  AAA  TCC  TTG  CAG  CAT  GAC  AAC  ATC  GTC  AAG  TAC  AAG  GGA  GTG         2340
Leu  Lys  Ser  Leu  Gln  His  Asp  Asn  Ile  Val  Lys  Tyr  Lys  Gly  Val
               770                 775                      780

TGC  TAC  AGT  GCG  GGT  CGG  CGC  AAC  CTA  AGA  TTA  ATT  ATG  GAA  TAT         2385
Cys  Tyr  Ser  Ala  Gly  Arg  Arg  Asn  Leu  Arg  Leu  Ile  Met  Glu  Tyr
               785                 790                      795
```

| | | | | | | | | | | | | | | | |
|---|---|---|---|---|---|---|---|---|---|---|---|---|---|---|---|
| TTA | CCA | TAT | GGA | AGT | TTA | CGA | GAC | TAT | CTC | CAA | AAA | CAT | AAA | GAA | 2430 |
| Leu | Pro | Tyr | Gly | Ser 800 | Leu | Arg | Asp | Tyr | Leu 805 | Gln | Lys | His | Lys 810 | Glu | |
| CGG | ATA | GAT | CAC | AAA | AAA | CTT | CTT | CAA | TAC | ACA | TCT | CAG | ATA | TGC | 2475 |
| Arg | Ile | Asp | His | Lys 815 | Lys | Leu | Leu | Gln | Tyr 820 | Thr | Ser | Gln | Ile 825 | Cys | |
| AAG | GGC | ATG | GAA | TAT | CTT | GGT | ACA | AAA | AGG | TAT | ATC | CAC | AGG | GAC | 2520 |
| Lys | Gly | Met | Glu | Tyr 830 | Leu | Gly | Thr | Lys | Arg 835 | Tyr | Ile | His | Arg 840 | Asp | |
| CTG | GCA | ACA | AGG | AAC | ATA | TTG | GTG | GAA | AAT | GAG | AAC | AGG | GTT | AAA | 2565 |
| Leu | Ala | Thr | Arg | Asn 845 | Ile | Leu | Val | Glu | Asn 850 | Glu | Asn | Arg | Val 855 | Lys | |
| ATA | GGA | GAC | TTC | GGA | TTA | ACC | AAA | GTC | TTG | CCG | CAG | GAC | AAA | GAA | 2610 |
| Ile | Gly | Asp | Phe | Gly 860 | Leu | Thr | Lys | Val | Leu 865 | Pro | Gln | Asp | Lys 870 | Glu | |
| TAC | TAC | AAA | GTA | AAG | GAG | CCA | GGG | GAA | AGC | CCC | ATA | TTC | TGG | TAC | 2655 |
| Tyr | Tyr | Lys | Val | Lys 875 | Glu | Pro | Gly | Glu | Ser 880 | Pro | Ile | Phe | Trp 885 | Tyr | |
| GCA | CCT | GAA | TCC | TTG | ACG | GAG | AGC | AAG | TTT | TCT | GTG | GCC | TCA | GAT | 2700 |
| Ala | Pro | Glu | Ser | Leu 890 | Thr | Glu | Ser | Lys | Phe 895 | Ser | Val | Ala | Ser 900 | Asp | |
| GTG | TGG | AGC | TTT | GGA | GTG | GTT | CTA | TAC | GAA | CTT | TTC | ACA | TAC | ATC | 2745 |
| Val | Trp | Ser | Phe | Gly 905 | Val | Val | Leu | Tyr | Glu 910 | Leu | Phe | Thr | Tyr 915 | Ile | |
| GAG | AAG | AGT | AAA | AGT | CCA | CCC | GTG | GAA | TTT | ATG | CGA | ATG | ATT | GGC | 2790 |
| Glu | Lys | Ser | Lys | Ser 920 | Pro | Pro | Val | Glu | Phe 925 | Met | Arg | Met | Ile 930 | Gly | |
| AAT | GAT | AAA | CAA | GGG | CAA | ATG | ATT | GTG | TTC | CAT | TTG | ATA | GAG | CTA | 2835 |
| Asn | Asp | Lys | Gln | Gly 935 | Gln | Met | Ile | Val | Phe 940 | His | Leu | Ile | Glu 945 | Leu | |
| CTG | AAG | AGC | AAC | GGA | AGA | TTG | CCA | AGG | CCA | GAA | GGA | TGC | CCA | GAT | 2880 |
| Leu | Lys | Ser | Asn | Gly 950 | Arg | Leu | Pro | Arg | Pro 955 | Glu | Gly | Cys | Pro 960 | Asp | |
| GAG | ATT | TAT | GTG | ATC | ATG | ACA | GAG | TGC | TGG | AAC | AAC | AAT | GTG | AGC | 2925 |
| Glu | Ile | Tyr | Val | Ile 965 | Met | Thr | Glu | Cys | Trp 970 | Asn | Asn | Asn | Val 975 | Ser | |
| CAG | CGT | CCC | TCC | TTC | AGG | GAC | CTT | TCC | TTC | GGG | TGG | ATC | AAA | TCC | 2970 |
| Gln | Arg | Pro | Ser | Phe 980 | Arg | Asp | Leu | Ser | Phe 985 | Gly | Trp | Ile | Lys 990 | Ser | |

| | | | | |
|---|---|---|---|---|
| GGG ACA GTA | TAGCTGCGTG | AAAGAGATGG | CCTTACTCAG | AGACCAAGCA | 3019 |
| Gly Thr Val | | | | | |
| GACTTCCAGA | ACCAGAACAA | AGCTCTGTAG | CCTTGTGTCT | ACACATCCTT | 3069 |
| ATCATGACGC | TAGCTAGGCA | GAAAGAAAAC | TGTGACGCCG | TCTGCTCAAA | 3119 |
| AGCTTTGGAA | AACGCCGTGC | AGGTTTGTTT | CATCACCATC | TGTAAAAACC | 3169 |
| ACTGCTCAAG | TCTGGCAGCA | TGCTTGTGGG | CTGATGCATG | GAGCTCACCA | 3219 |
| CAGAGTCTCT | GCATCTCCTC | TGACAGAAGA | AGAAAAATAG | ACAATTTTCA | 3269 |
| ACTCACTTTT | TTGAGAAATG | GAAAAAAATT | ATAATGTAAA | TTTTTCAGTG | 3319 |
| TAGGAAATAC | ACAGAACATA | CATGTACAGT | TTTTACCACG | TGGAGTGTAT | 3369 |
| AATACTTTGG | CCTCTTGTGT | GATTTACATG | AGGGCTGATG | TTTGTTAATG | 3419 |
| TTTTCTAATT | TTTCCATAGG | TGATCTATAA | TAACTTCATG | ATACAAATTA | 3469 |
| AAATGCTCAG | AAAATTAAAA | AAAAAA | | | 3495 |

( 2 ) INFORMATION FOR SEQ ID NO:3:

( i ) SEQUENCE CHARACTERISTICS:
( A ) LENGTH: 6 amino acid residues (B) TYPE: amino acid
(D) TOPOLOGY: linear (ix) FEATURE:
(D) OTHER INFORMATION: Xaa in positions 2, 4 and 5 is unknown.

(xi) SEQUENCE DESCRIPTION: SEQ ID NO: 3:

```
Gly Xaa Gly Xaa Xaa Gly
             5
```

(2) INFORMATION FOR SEQ ID NO:4:

(i) SEQUENCE CHARACTERISTICS:
(A) LENGTH: 16 amino acid residues
(B) TYPE: amino acid
(D) TOPOLOGY: linear (xi) SEQUENCE DESCRIPTION: SEQ ID NO: 4:

```
Thr Ser Phe Gln Asn Leu Ile Glu Cys Phe Glu Ala Leu Leu Lys Cys
             5                       10                      15
```

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 5:

```
TACACCTTTA AATATTTTG T
```

(2) INFORMATION FOR SEQ ID NO:6:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 6:

```
CTCGAGTCGA CGAATTC
```

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 7:

```
CTTGCTTAAT ACTGACATCA
```

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 8:

```
CTTGCTTAAT ACTGACATCA
```

(2) INFORMATION FOR SEQ ID NO:9:

(i) SEQUENCE CHARACTERISTICS:

(A) LENGTH: 9 base pairs
          (B) TYPE: nucleic acid
          (C) STRANDEDNESS: single
          (D) TOPOLOGY: linear (xi) SEQUENCE DESCRIPTION: SEQ ID NO: 9:

TAAATGCAG (2) INFORMATION FOR SEQ ID NO:10:

(i) SEQUENCE CHARACTERISTICS:
          (A) LENGTH: 9 base pairs
          (B) TYPE: nucleic acid
          (C) STRANDEDNESS: single
          (D) TOPOLOGY: linear (xi) SEQUENCE DESCRIPTION: SEQ ID NO: 10:

GCCATGGCT (2) INFORMATION FOR SEQ ID NO:11:

(i) SEQUENCE CHARACTERISTICS:
          (A) LENGTH: 8 amino acid residues
          (B) TYPE: amino acid
          (D) TOPOLOGY: linear (xi) SEQUENCE DESCRIPTION: SEQ ID NO: 11:

Gly Leu Tyr Val Leu Arg Trp Ser
                  8

(2) INFORMATION FOR SEQ ID NO:12:

(i) SEQUENCE CHARACTERISTICS:
          (A) LENGTH: 7 amino acid residues
          (B) TYPE: amino acid
          (D) TOPOLOGY: linear (xi) SEQUENCE DESCRIPTION: SEQ ID NO: 12:

Val Asp Gly Tyr Phe Arg Ile
              5

(2) INFORMATION FOR SEQ ID NO: 13:

(i) SEQUENCE CHARACTERISTICS:
          (A) LENGTH: 47 amino acids
          (B) TYPE: amino acid
          (D) TOPOLOGY: linear (xi) SEQUENCE DESCRIPTION: SEQ ID NO: 13:

Lys Ile Gly Glu Gly Thr Tyr Gly Val Val Tyr Lys Gly Arg His
                  5                  10                  15
Lys Thr Thr Gly Gln Val Val Ala Met Lys Lys Ile Arg Leu Glu
                 20                  25                  30
Ser Glu Glu Glu Gly Val Pro Ser Thr Ala Ile Arg Glu Ile Ser
                 35                  40                  45
Leu Leu (2) INFORMATION FOR SEQ ID NO: 14:

(i) SEQUENCE CHARACTERISTICS:
          (A) LENGTH: 82 amino acids
          (B) TYPE: amino acid
          (D) TOPOLOGY: linear (xi) SEQUENCE DESCRIPTION: SEQ ID NO: 14:

Val Phe Cys His Ser Arg Arg Val Leu His Arg Asp Leu Lys Pro

```
                   5                          10                         15
Gln  Asn  Leu  Leu  Ile  Asp  Asp  Lys  Gly  Thr  Ile  Lys  Leu  Ala  Asp
                   20                         25                         30

Phe  Gly  Leu  Ala  Arg  Ala  Phe  Gly  Ile  Pro  Ile  Arg  Val  Tyr  Thr
                   35                         40                         45

His  Glu  Val  Val  Thr  Leu  Trp  Tyr  Arg  Ser  Pro  Glu  Val  Leu  Leu
                   50                         55                         60

Gly  Ser  Ala  Arg  Tyr  Ser  Thr  Pro  Val  Asp  Ile  Trp  Ser  Ile  Gly
                   65                         70                         75

Thr  Ile  Phe  Ala  Glu  Leu  Ala
                   80
```

( 2 ) INFORMATION FOR SEQ ID NO: 15:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO: 15:

```
Leu  Ala  Ser  His  His  Val  Lys  Asn  Leu  Asp  Glu  Asn  Gly  Leu  Asp
                   5                          10                         15

Leu  Leu  Ser  Lys  Met  Leu  Ile  Tyr  Asp  Pro  Ala  Lys  Arg  Ile  Ser
                   20                         25                         30
```

( 2 ) INFORMATION FOR SEQ ID NO: 16:

( i ) SEQUENCE CHARACTERISTICS:
        ( A ) LENGTH: 601 amino acids
        ( B ) TYPE: amino acid
        ( D ) TOPOLOGY: linear ( x i ) SEQUENCE DESCRIPTION: SEQ ID NO: 16:

```
Val  Phe  His  Lys  Ile  Arg  Asn  Glu  Asp  Leu  Ile  Phe  Asn  Glu  Ser
                   5                          10                         15

Leu  Gly  Gln  Gly  Thr  Phe  Thr  Lys  Ile  Phe  Lys  Gly  Val  Arg  Arg
                   20                         25                         30

Glu  Val  Gly  Asp  Tyr  Gly  Gln  Leu  His  Glu  Thr  Glu  Val  Leu  Leu
                   35                         40                         45

Lys  Val  Leu  Asp  Lys  Ala  His  Arg  Asn  Tyr  Ser  Glu  Ser  Phe  Phe
                   50                         55                         60

Glu  Ala  Ala  Ser  Met  Met  Ser  Gln  Leu  Ser  His  Lys  His  Leu  Val
                   65                         70                         75

Leu  Asn  Tyr  Gly  Val  Cys  Val  Cys  Gly  Glu  Glu  Asn  Ile  Leu  Val
                   80                         85                         90

Gln  Glu  Phe  Val  Lys  Phe  Gly  Ser  Leu  Asp  Thr  Tyr  Leu  Lys  Lys
                   95                         100                        105

Asn  Lys  Asn  Ser  Ile  Asn  Ile  Leu  Trp  Lys  Leu  Gly  Val  Ala  Lys
                   110                        115                        120

Gln  Leu  Ala  Trp  Ala  Met  His  Phe  Leu  Glu  Glu  Lys  Ser  Leu  Ile
                   125                        130                        135

His  Gly  Asn  Val  Cys  Ala  Lys  Asn  Ile  Leu  Leu  Ile  Arg  Glu  Glu
                   140                        145                        150

Asp  Arg  Arg  Thr  Gly  Asn  Pro  Pro  Phe  Ile  Lys  Leu  Ser  Asp  Pro
                   155                        160                        165

Gly  Ile  Ser  Ile  Thr  Val  Leu  Pro  Lys  Asp  Ile  Ser  Ser  Cys  Cys
                   170                        175                        180

Phe  Gln  Val  Leu  Gln  Glu  Arg  Ile  Pro  Trp  Val  Pro  Pro  Glu  Cys
```

|   |   |   | 185 |   |   |   | 190 |   |   |   | 195 |   |
|---|---|---|---|---|---|---|---|---|---|---|---|---|
| Ile | Glu | Asn | Pro | Lys | Asn | Leu | Thr | Leu | Ala | Thr | Asp | Lys | Trp | Ser |
|   |   |   | 200 |   |   |   | 205 |   |   |   | 210 |
| Phe | Gly | Thr | Thr | Leu | Trp | Glu | Ile | Cys | Ser | Gly | Gly | Asp | Lys | Pro |
|   |   |   | 215 |   |   |   | 220 |   |   |   | 225 |
| Leu | Ser | Ala | Leu | Asp | Ser | Gln | Arg | Lys | Leu | Gln | Phe | Tyr | Glu | Asp |
|   |   |   | 230 |   |   |   | 235 |   |   |   | 240 |
| Lys | His | Gln | Leu | Pro | Ala | Pro | Lys | Trp | Thr | Glu | Leu | Ala | Asn | Leu |
|   |   |   | 245 |   |   |   | 250 |   |   |   | 255 |
| Ile | Asn | Asn | Cys | Met | Asp | Tyr | Glu | Pro | Asp | Phe | Arg | Pro | Ala | Phe |
|   |   |   | 260 |   |   |   | 265 |   |   |   | 270 |
| Arg | Ala | Val | Ile | Arg | Asp | Leu | Asn | Ser | Leu | Phe | Thr | Pro | Asp | Tyr |
|   |   |   | 275 |   |   |   | 280 |   |   |   | 285 |
| Glu | Leu | Leu | Thr | Glu | Asn | Asp | Met | Leu | Pro | Asn | Met | Arg | Ile | Gly |
|   |   |   | 290 |   |   |   | 295 |   |   |   | 300 |
| Ala | Leu | Gly | Phe | Ser | Gly | Ala | Phe | Glu | Asp | Arg | Asp | Pro | Thr | Gln |
|   |   |   | 305 |   |   |   | 310 |   |   |   | 315 |
| Phe | Glu | Glu | Arg | His | Leu | Lys | Phe | Leu | Gln | Gln | Leu | Gly | Lys | Gly |
|   |   |   | 320 |   |   |   | 325 |   |   |   | 330 |
| Asn | Phe | Gly | Ser | Val | Glu | Met | Cys | Arg | Tyr | Asp | Pro | Leu | Gln | Asp |
|   |   |   | 335 |   |   |   | 340 |   |   |   | 345 |
| Asn | Thr | Gly | Glu | Val | Val | Ala | Val | Lys | Lys | Leu | Gln | His | Ser | Thr |
|   |   |   | 350 |   |   |   | 355 |   |   |   | 360 |
| Glu | Glu | His | Leu | Arg | Asp | Phe | Glu | Arg | Glu | Ile | Glu | Ile | Leu | Lys |
|   |   |   | 365 |   |   |   | 370 |   |   |   | 375 |
| Ser | Leu | Gln | His | Asp | Asn | Ile | Val | Lys | Tyr | Lys | Gly | Val | Cys | Tyr |
|   |   |   | 380 |   |   |   | 385 |   |   |   | 390 |
| Ser | Ala | Gly | Arg | Arg | Asn | Leu | Arg | Leu | Ile | Met | Glu | Tyr | Leu | Pro |
|   |   |   | 395 |   |   |   | 400 |   |   |   | 405 |
| Tyr | Gly | Ser | Leu | Arg | Asp | Tyr | Leu | Gln | Lys | His | Lys | Glu | Arg | Ile |
|   |   |   | 410 |   |   |   | 415 |   |   |   | 420 |
| Asp | His | Lys | Lys | Leu | Leu | Gln | Tyr | Thr | Ser | Gln | Ile | Cys | Lys | Gly |
|   |   |   | 425 |   |   |   | 430 |   |   |   | 435 |
| Met | Glu | Tyr | Leu | Gly | Thr | Lys | Arg | Tyr | Ile | His | Arg | Asp | Leu | Ala |
|   |   |   | 440 |   |   |   | 445 |   |   |   | 450 |
| Thr | Arg | Asn | Ile | Leu | Val | Glu | Asn | Glu | Asn | Arg | Val | Lys | Ile | Gly |
|   |   |   | 455 |   |   |   | 460 |   |   |   | 465 |
| Asp | Phe | Gly | Leu | Thr | Lys | Val | Leu | Pro | Gln | Asp | Lys | Glu | Tyr | Tyr |
|   |   |   | 470 |   |   |   | 475 |   |   |   | 480 |
| Lys | Val | Lys | Glu | Pro | Gly | Glu | Ser | Pro | Ile | Phe | Trp | Tyr | Ala | Pro |
|   |   |   | 485 |   |   |   | 490 |   |   |   | 495 |
| Glu | Ser | Leu | Thr | Glu | Ser | Lys | Phe | Ser | Val | Ala | Ser | Asp | Val | Trp |
|   |   |   | 500 |   |   |   | 505 |   |   |   | 510 |
| Ser | Phe | Gly | Val | Val | Leu | Tyr | Glu | Leu | Phe | Thr | Tyr | Ile | Glu | Lys |
|   |   |   | 515 |   |   |   | 520 |   |   |   | 525 |
| Ser | Lys | Ser | Pro | Pro | Val | Glu | Phe | Met | Arg | Met | Ile | Gly | Asn | Asp |
|   |   |   | 530 |   |   |   | 535 |   |   |   | 540 |
| Lys | Gln | Gly | Gln | Met | Ile | Val | Phe | His | Leu | Ile | Glu | Leu | Leu | Lys |
|   |   |   | 545 |   |   |   | 550 |   |   |   | 555 |
| Ser | Asn | Gly | Arg | Leu | Pro | Arg | Pro | Glu | Gly | Cys | Pro | Asp | Glu | Ile |
|   |   |   | 560 |   |   |   | 565 |   |   |   | 570 |
| Tyr | Val | Ile | Met | Thr | Glu | Cys | Trp | Asn | Asn | Val | Ser | Gln | Arg |
|   |   |   | 575 |   |   |   | 580 |   |   |   | 585 |

| | | | | | | | | | | | | |
|---|---|---|---|---|---|---|---|---|---|---|---|---|
|Pro|Ser|Phe|Arg|Asp|Leu|Ser|Phe|Gly|Trp|Ile|Lys|Ser|Gly|Thr|
| | | | |590| | | |595| | | |600|

Val ( 2 ) INFORMATION FOR SEQ ID NO: 17:

( i ) SEQUENCE CHARACTERISTICS:
( A ) LENGTH: 581 amino acids
( B ) TYPE: amino acid
( D ) TOPOLOGY: linear ( x i ) SEQUENCE DESCRIPTION: SEQ ID NO: 17:

| | | | | | | | | | | | | | | |
|---|---|---|---|---|---|---|---|---|---|---|---|---|---|---|
|Ser|Phe|Asp|Arg|Ile|Leu|Lys|Lys|Asp|Leu|Val|Gln|Gly|Glu|His|
| | | | |5| | | | |10| | | | |15|
|Leu|Gly|Arg|Gly|Thr|Arg|Thr|His|Ile|Tyr|Ser|Gly|Thr|Leu|Met|
| | | | |20| | | | |25| | | | |30|
|Asp|Tyr|Lys|Asp|Asp|Glu|Gly|Thr|Ser|Glu|Glu|Lys|Lys|Ile|Lys|
| | | | |35| | | | |40| | | | |45|
|Val|Ile|Leu|Lys|Val|Leu|Asp|Pro|Ser|His|Arg|Asp|Ile|Ser|Leu|
| | | | |50| | | | |55| | | | |60|
|Ala|Phe|Phe|Glu|Ala|Ala|Ser|Met|Met|Arg|Gln|Val|Ser|His|Lys|
| | | | |65| | | | |70| | | | |75|
|His|Ile|Val|Tyr|Leu|Tyr|Gly|Val|Cys|Val|Arg|Asp|Val|Glu|Asn|
| | | | |80| | | | |85| | | | |90|
|Ile|Met|Val|Glu|Glu|Phe|Val|Glu|Gly|Gly|Pro|Leu|Asp|Leu|Phe|
| | | | |95| | | | |100| | | | |105|
|Met|His|Arg|Lys|Ser|Asp|Val|Leu|Thr|Thr|Pro|Trp|Lys|Phe|Lys|
| | | | |110| | | | |115| | | | |120|
|Val|Ala|Lys|Gln|Leu|Ala|Ser|Ala|Leu|Ser|Tyr|Leu|Glu|Asp|Lys|
| | | | |125| | | | |130| | | | |135|
|Asp|Leu|Val|His|Gly|Asn|Val|Cys|Thr|Lys|Asn|Leu|Leu|Leu|Ala|
| | | | |140| | | | |145| | | | |150|
|Arg|Glu|Gly|Ile|Asp|Ser|Glu|Cys|Gly|Pro|Phe|Ile|Lys|Leu|Ser|
| | | | |155| | | | |160| | | | |165|
|Asp|Pro|Gly|Ile|Pro|Ile|Thr|Val|Leu|Ser|Arg|Gln|Glu|Cys|Ile|
| | | | |170| | | | |175| | | | |180|
|Glu|Arg|Ile|Pro|Trp|Ile|Ala|Pro|Glu|Cys|Val|Glu|Asp|Ser|Lys|
| | | | |185| | | | |190| | | | |195|
|Asn|Leu|Ser|Val|Ala|Ala|Asp|Lys|Trp|Ser|Phe|Gly|Thr|Thr|Leu|
| | | | |200| | | | |205| | | | |210|
|Trp|Glu|Ile|Cys|Tyr|Asn|Gly|Glu|Ile|Pro|Leu|Lys|Asp|Lys|Thr|
| | | | |215| | | | |220| | | | |225|
|Leu|Ile|Glu|Lys|Glu|Arg|Phe|Tyr|Glu|Ser|Arg|Cys|Arg|Pro|Val|
| | | | |230| | | | |235| | | | |240|
|Thr|Pro|Ser|Cys|Lys|Glu|Leu|Ala|Asp|Leu|Met|Thr|Arg|Cys|Met|
| | | | |245| | | | |250| | | | |255|
|Asn|Tyr|Asp|Pro|Asn|Gln|Arg|Pro|Phe|Phe|Arg|Ala|Ile|Met|Arg|
| | | | |260| | | | |265| | | | |270|
|Asp|Ile|Asn|Lys|Leu|Glu|Glu|Gln|Asn|Pro|Asp|Ile|Val|Ser|Arg|
| | | | |275| | | | |280| | | | |285|
|Lys|Lys|Asn|Gln|Pro|Thr|Glu|Val|Asp|Pro|Thr|His|Phe|Thr|Lys|
| | | | |290| | | | |295| | | | |300|
|Arg|Phe|Leu|Lys|Arg|Ile|Arg|Asp|Leu|Gly|Glu|Gly|His|Phe|Gly|
| | | | |305| | | | |310| | | | |315|
|Lys|Val|Glu|Leu|Cys|Arg|Tyr|Asp|Pro|Glu|Asp|Asn|Thr|Gly|Glu|
| | | | |320| | | | |325| | | | |330|

| | | | | | | | | | | | | | | |
|---|---|---|---|---|---|---|---|---|---|---|---|---|---|---|
|Gln|Val|Ala|Val|Lys<br>335|Ser|Leu|Lys|Pro|Glu<br>340|Ser|Gly|Gly|Asn|His<br>345|
|Ile|Ala|Asp|Leu|Lys<br>350|Lys|Glu|Ile|Ile|Leu<br>355|Arg|Asn|Leu|Tyr<br>360||
|His|Glu|Asn|Ile|Val<br>365|Lys|Tyr|Lys|Gly|Ile<br>370|Cys|Thr|Glu|Asp|Gly<br>375|
|Gly|Asn|Gly|Ile|Lys<br>380|Leu|Ile|Met|Glu|Phe<br>385|Leu|Pro|Ser|Gly|Ser<br>390|
|Leu|Lys|Glu|Tyr|Leu<br>395|Pro|Lys|Asn|Lys|Asn<br>400|Lys|Ile|Asn|Leu|Lys<br>405|
|Gln|Gln|Leu|Lys|Tyr<br>410|Ala|Val|Gln|Ile|Cys<br>415|Lys|Gly|Met|Asp|Tyr<br>420|
|Leu|Gly|Ser|Arg|Gln<br>425|Tyr|Val|His|Arg|Asp<br>430|Leu|Ala|Ala|Arg|Asn<br>435|
|Val|Leu|Val|Glu|Ser<br>440|Glu|His|Gln|Val|Lys<br>445|Ile|Gly|Asp|Phe|Gly<br>450|
|Leu|Thr|Lys|Ala|Ile<br>455|Glu|Thr|Asp|Lys|Glu<br>460|Tyr|Tyr|Thr|Val|Lys<br>465|
|Asp|Asp|Arg|Asp|Ser<br>470|Pro|Val|Phe|Trp|Tyr<br>475|Ala|Pro|Glu|Cys|Leu<br>480|
|Met|Gln|Ser|Lys|Phe<br>485|Tyr|Ile|Ala|Ser|Asp<br>490|Val|Trp|Ser|Phe|Gly<br>495|
|Val|Thr|Leu|His|Glu<br>500|Leu|Leu|Thr|Tyr|Cys<br>505|Asp|Ser|Asp|Ser|Ser<br>510|
|Pro|Met|Ala|Leu|Phe<br>515|Leu|Lys|Met|Ile|Gly<br>520|Pro|Thr|His|Gly|Gln<br>525|
|Met|Thr|Val|Thr|Arg<br>530|Leu|Val|Asn|Thr|Leu<br>535|Lys|Glu|Gly|Lys|Arg<br>540|
|Leu|Pro|Cys|Pro|Pro<br>545|Asn|Cys|Pro|Asp|Glu<br>550|Val|Tyr|Gln|Leu|Met<br>555|
|Arg|Lys|Cys|Trp|Glu<br>560|Phe|Gln|Pro|Ser|Asn<br>565|Arg|Thr|Ser|Phe|Gln<br>570|
|Asn|Leu|Ile|Glu|Gly<br>575|Phe|Glu|Ala|Leu|Leu<br>580|Lys| | | | |

(2) INFORMATION FOR SEQ ID NO: 18:

(i) SEQUENCE CHARACTERISTICS:
  (A) LENGTH: 1132 amino acids
  (B) TYPE: amino acid
  (D) TOPOLOGY: linear (xi) SEQUENCE DESCRIPTION: SEQ ID NO: 18:

| | | | | | | | | | | | | | | |
|---|---|---|---|---|---|---|---|---|---|---|---|---|---|---|
|Met|Gln|Tyr|Leu|Asn<br>5|Ile|Lys|Glu|Asp|Cys<br>10|Asn|Ala|Met|Ala|Phe<br>15|
|Cys|Ala|Lys|Met|Arg<br>20|Ser|Ser|Lys|Lys|Thr<br>25|Glu|Val|Asn|Leu|Glu<br>30|
|Ala|Pro|Glu|Pro|Gly<br>35|Val|Glu|Val|Ile|Phe<br>40|Tyr|Leu|Ser|Asp|Arg<br>45|
|Glu|Pro|Leu|Arg|Leu<br>50|Gly|Ser|Gly|Glu|Tyr<br>55|Thr|Ala|Glu|Glu|Leu<br>60|
|Cys|Ile|Arg|Ala|Ala<br>65|Gln|Ala|Cys|Arg|Ile<br>70|Ser|Pro|Leu|Cys|His<br>75|
|Asn|Leu|Phe|Ala|Leu<br>80|Tyr|Asp|Glu|Asn|Thr<br>85|Lys|Leu|Trp|Tyr|Ala<br>90|

```
Pro  Asn  Arg  Thr  Ile  Thr  Val  Asp  Asp  Lys  Met  Ser  Leu  Arg  Leu
                    95                  100                           105

His  Tyr  Arg  Met  Arg  Phe  Tyr  Phe  Thr  Asn  Trp  His  Gly  Thr  Asn
                    110                 115                           120

Asp  Asn  Glu  Gln  Ser  Val  Trp  Arg  His  Ser  Pro  Lys  Lys  Gln  Lys
                    125                 130                           135

Asn  Gly  Tyr  Glu  Lys  Lys  Lys  Ile  Pro  Asp  Ala  Thr  Pro  Leu  Leu
                    140                 145                           150

Asp  Ala  Ser  Ser  Leu  Glu  Tyr  Leu  Phe  Ala  Gln  Gly  Gln  Tyr  Asp
                    155                 160                           165

Leu  Val  Lys  Cys  Leu  Ala  Pro  Ile  Arg  Asp  Pro  Lys  Thr  Glu  Gln
                    170                 175                           180

Asp  Gly  His  Asp  Ile  Glu  Asn  Glu  Cys  Leu  Gly  Met  Ala  Val  Leu
                    185                 190                           195

Ala  Ile  Ser  His  Tyr  Ala  Met  Met  Lys  Lys  Met  Gln  Leu  Pro  Glu
                    200                 205                           210

Leu  Pro  Lys  Asp  Ile  Ser  Tyr  Lys  Arg  Tyr  Ile  Pro  Glu  Thr  Leu
                    215                 220                           225

Asn  Lys  Ser  Ile  Arg  Gln  Arg  Asn  Leu  Leu  Thr  Arg  Met  Arg  Ile
                    230                 235                           240

Asn  Asn  Val  Phe  Lys  Asp  Phe  Leu  Lys  Glu  Phe  Asn  Asn  Lys  Thr
                    245                 250                           255

Ile  Cys  Asp  Ser  Ser  Val  Ser  Thr  His  Asp  Leu  Lys  Val  Lys  Tyr
                    260                 265                           270

Leu  Ala  Thr  Leu  Glu  Thr  Leu  Thr  Lys  His  Tyr  Gly  Ala  Glu  Ile
                    275                 280                           285

Phe  Glu  Thr  Ser  Met  Leu  Leu  Ile  Ser  Ser  Glu  Asn  Glu  Met  Asn
                    290                 295                           300

Trp  Phe  His  Ser  Asn  Asp  Gly  Gly  Asn  Val  Leu  Tyr  Tyr  Glu  Val
                    305                 310                           315

Met  Val  Thr  Gly  Asn  Leu  Gly  Ile  Gln  Trp  Arg  His  Lys  Pro  Asn
                    320                 325                           330

Val  Val  Ser  Val  Glu  Lys  Glu  Lys  Asn  Lys  Leu  Lys  Arg  Lys  Lys
                    335                 340                           345

Leu  Glu  Asn  Lys  Asp  Lys  Lys  Asp  Glu  Glu  Lys  Asn  Lys  Ile  Arg
                    350                 355                           360

Glu  Glu  Trp  Asn  Asn  Phe  Ser  Phe  Phe  Pro  Glu  Ile  Thr  His  Ile
                    365                 370                           375

Val  Ile  Lys  Glu  Ser  Val  Val  Ser  Ile  Asn  Lys  Gln  Asp  Asn  Lys
                    380                 385                           390

Lys  Met  Glu  Leu  Lys  Leu  Ser  Ser  His  Glu  Glu  Ala  Leu  Ser  Phe
                    395                 400                           405

Val  Ser  Leu  Val  Asp  Gly  Tyr  Phe  Arg  Leu  Thr  Ala  Asp  Ala  His
                    410                 415                           420

His  Tyr  Leu  Cys  Thr  Asp  Val  Ala  Pro  Pro  Leu  Ile  Val  His  Asn
                    425                 430                           435

Ile  Gln  Asn  Gly  Cys  His  Gly  Pro  Ile  Cys  Glu  Tyr  Ala  Ile  Asn
                    440                 445                           450

Lys  Leu  Arg  Gln  Glu  Gly  Ser  Glu  Glu  Gly  Met  Tyr  Val  Leu  Arg
                    455                 460                           465

Trp  Ser  Cys  Thr  Asp  Phe  Asp  Asn  Ile  Leu  Met  Thr  Val  Thr  Cys
                    470                 475                           480

Phe  Glu  Lys  Ser  Glu  Gln  Val  Gln  Gly  Ala  Gln  Lys  Gln  Phe  Lys
                    485                 490                           495
```

-continued

| | | | | | | | | | | | | | |
|---|---|---|---|---|---|---|---|---|---|---|---|---|---|
|Asn|Phe|Gln|Ile|Glu 500|Val|Gln|Lys|Gly|Arg 505|Tyr|Ser|Leu|His Gly 510|
|Ser|Asp|Arg|Ser|Phe 515|Pro|Ser|Leu|Gly|Asp 520|Leu|Met|Ser|His Leu 525|
|Lys|Lys|Gln|Ile|Leu 530|Arg|Thr|Asp|Asn|Ile 535|Ser|Phe|Met|Leu Lys 540|
|Arg|Cys|Cys|Gln|Pro 545|Lys|Pro|Arg|Glu|Ile 550|Ser|Asn|Leu|Leu Val 555|
|Ala|Thr|Lys|Lys|Ala 560|Gln|Glu|Trp|Gln|Pro 565|Val|Tyr|Pro|Met Ser 570|
|Gln|Leu|Ser|Phe|Asp 575|Arg|Ile|Leu|Lys|Lys 580|Asp|Leu|Val|Gln Gly 585|
|Glu|His|Leu|Gly|Arg 590|Gly|Thr|Arg|Thr|His 595|Ile|Tyr|Ser|Gly Thr 600|
|Leu|Met|Asp|Tyr|Lys 605|Asp|Asp|Glu|Gly|Thr 610|Ser|Glu|Glu|Lys Lys 615|
|Ile|Lys|Val|Ile|Leu 620|Lys|Val|Leu|Asp|Pro 625|Ser|His|Arg|Asp Ile 630|
|Ser|Leu|Ala|Phe|Phe 635|Glu|Ala|Ala|Ser|Met 640|Met|Arg|Gln|Val Ser 645|
|His|Lys|His|Ile|Val 650|Tyr|Leu|Tyr|Gly|Val 655|Cys|Val|Arg|Asp Val 660|
|Glu|Asn|Ile|Met|Val 665|Glu|Glu|Phe|Val|Glu 670|Gly|Gly|Pro|Leu Asp 675|
|Leu|Phe|Met|His|Arg 680|Lys|Ser|Asp|Val|Leu 685|Thr|Thr|Pro|Trp Lys 690|
|Phe|Lys|Val|Ala|Lys 695|Gln|Leu|Ala|Ser|Ala 700|Leu|Ser|Tyr|Leu Glu 705|
|Asp|Lys|Asp|Leu|Val 710|His|Gly|Asn|Val|Cys 715|Thr|Lys|Asn|Leu Leu 720|
|Leu|Ala|Arg|Glu|Gly 725|Ile|Asp|Ser|Glu|Cys 730|Gly|Pro|Phe|Ile Lys 735|
|Leu|Ser|Asp|Pro|Gly 740|Ile|Pro|Ile|Thr|Val 745|Leu|Ser|Arg|Gln Glu 750|
|Cys|Ile|Glu|Arg|Ile 755|Pro|Trp|Ile|Ala|Pro 760|Glu|Cys|Val|Glu Asp 765|
|Ser|Lys|Asn|Leu|Ser 770|Val|Ala|Ala|Asp|Lys 775|Trp|Ser|Phe|Gly Thr 780|
|Thr|Leu|Trp|Glu|Ile 785|Cys|Tyr|Asn|Gly|Glu 790|Ile|Pro|Leu|Lys Asp 795|
|Lys|Thr|Leu|Ile|Glu 800|Lys|Glu|Arg|Phe|Tyr 805|Glu|Ser|Arg|Cys Arg 810|
|Pro|Val|Thr|Pro|Ser 815|Cys|Lys|Glu|Leu|Ala 820|Asp|Leu|Met|Thr Arg 825|
|Cys|Met|Asn|Tyr|Asp 830|Pro|Asn|Gln|Arg|Pro 835|Phe|Phe|Arg|Ala Ile 840|
|Met|Arg|Asp|Ile|Asn 845|Lys|Leu|Glu|Glu|Gln 850|Asn|Pro|Asp|Ile Val 855|
|Ser|Arg|Lys|Lys|Asn 860|Gln|Pro|Thr|Glu|Val 865|Asp|Pro|Thr|His Phe 870|
|Lys|Arg|Phe|Leu|Lys 875|Arg|Ile|Arg|Asp|Leu 880|Gly|Glu|Gly|His Phe 885|
|Gly|Lys|Val|Glu|Leu|Cys|Arg|Tyr|Asp|Pro|Glu|Asp|Asn|Thr Gly|

|   |   |   |   |   |   |   |   | 890 |   |   |   |   | 895 |   |   |   |   | 900 |
|---|---|---|---|---|---|---|---|---|---|---|---|---|---|---|---|---|---|---|

Glu Gln Val Ala Val Lys Ser Leu Lys Pro Glu Ser Gly Gly Asn
                                905                910                915

His Ile Ala Asp Leu Lys Lys Glu Ile Glu Ile Leu Arg Asn Leu
                920                925                930

Tyr His Glu Asn Ile Val Lys Tyr Lys Gly Ile Cys Thr Glu Asp
                935                940                945

Gly Gly Asn Gly Ile Lys Leu Ile Met Glu Phe Leu Pro Ser Gly
                950                955                960

Ser Leu Lys Glu Tyr Leu Pro Lys Asn Lys Asn Lys Ile Asn Leu
                965                970                975

Lys Gln Gln Leu Lys Tyr Ala Val Gln Ile Cys Lys Gly Met Asp
                980                985                990

Tyr Leu Gly Ser Arg Gln Tyr Val His Arg Asp Leu Ala Ala Arg
                995                1000               1005

Asn Val Leu Val Glu Ser Glu His Gln Val Lys Ile Gly Asp Phe
                1010               1015               1020

Gly Leu Thr Lys Ala Ile Glu Thr Asp Lys Glu Tyr Tyr Thr Val
                1025               1030               1035

Lys Asp Asp Arg Asp Ser Pro Val Phe Trp Tyr Ala Pro Glu Cys
                1040               1045               1050

Leu Met Gln Ser Lys Phe Tyr Ile Ala Ser Asp Val Trp Ser Phe
                1055               1060               1065

Gly Val Thr Leu His Glu Leu Leu Thr Tyr Cys Asp Ser Asp Ser
                1070               1075               1080

Ser Pro Met Ala Leu Phe Leu Lys Met Ile Gly Pro Thr His Gly
                1085               1090               1095

Gln Met Thr Val Thr Arg Leu Val Asn Thr Leu Lys Glu Gly Lys
                1100               1105               1110

Arg Leu Pro Cys Pro Pro Asn Cys Pro Asp Glu Val Tyr Gln Leu
                1115               1120               1125

Met Arg Lys Cys Trp Glu Phe
                1130

( 2 ) INFORMATION FOR SEQ ID NO: 19:

( i ) SEQUENCE CHARACTERISTICS:
       ( A ) LENGTH: 971 amino acids
       ( B ) TYPE: amino acid
       ( D ) TOPOLOGY: linear ( x i ) SEQUENCE DESCRIPTION: SEQ ID NO: 19:

Leu Leu Asp Asp Phe Val Met Ser Tyr Leu Ser Pro Gln Trp Arg
                5                  10                 15

His Asp Phe Val His Gly Trp Ile Lys Val Pro Val Thr His Glu
                20                 25                 30

Thr Gln Glu Glu Cys Leu Gly Met Ala Val Leu Asp Met Met Arg
                35                 40                 45

Ile Ala Lys Glu Lys Asp Gln Thr Pro Leu Ala Val Tyr Asn Ser
                50                 55                 60

Val Ser Tyr Lys Thr Phe Leu Pro Lys Cys Val Arg Ala Lys Ile
                65                 70                 75

Gln Asp Tyr His Ile Leu Thr Arg Lys Arg Ile Arg Tyr Arg Phe
                80                 85                 90

Arg Arg Phe Ile Gln Gln Phe Ser Gln Cys Lys Ala Thr Ala Arg
                95                 100                105

```
Asn Leu Lys Leu Lys Tyr Leu Ile Asn Leu Glu Thr Leu Gln Ser
            110                 115                 120

Ala Phe Tyr Thr Glu Gln Phe Glu Val Lys Glu Ser Ala Arg Gly
            125                 130                 135

Pro Ser Gly Glu Glu Ile Phe Ala Thr Ile Ile Ile Thr Gly Asn
            140                 145                 150

Gly Gly Ile Gln Trp Ser Arg Gly Lys His Lys Glu Ser Glu Thr
            155                 160                 165

Leu Thr Glu Gln Asp Leu Gln Leu Tyr Cys Asp Phe Pro Asp Ile
            170                 175                 180

Ile Asp Val Ser Ile Lys Gln Ala Asn Gln Glu Cys Ser Thr Glu
            185                 190                 195

Ser Arg Ile Val Thr Val His Lys Gln Asp Gly Glu Val Leu Glu
            200                 205                 210

Ile Glu Leu Ser Ser Leu Lys Glu Ala Leu Ser Phe Val Ser Leu
            215                 220                 225

Ile Asp Gly Tyr Tyr Arg Leu Thr Ala Asp Ala His His Tyr Leu
            230                 235                 240

Cys Lys Glu Val Ala Pro Pro Ala Val Leu Glu Asn Ile His Ser
            245                 250                 255

Asn Cys His Gly Pro Ile Ser Met Asp Phe Ala Ile Ser Lys Leu
            260                 265                 270

Lys Lys Ala Gly Asn Gln Thr Gly Leu Tyr Val Leu Arg Cys Ser
            275                 280                 285

Pro Lys Asp Phe Asn Lys Tyr Phe Leu Thr Phe Ala Val Glu Arg
            290                 295                 300

Glu Asn Val Ile Glu Tyr Lys His Cys Leu Ile Thr Lys Asn Glu
            305                 310                 315

Asn Gly Glu Tyr Asn Leu Ser Gly Thr Lys Arg Asn Phe Ser Ser
            320                 325                 330

Leu Lys Asp Leu Leu Asn Cys Tyr Gln Met Glu Thr Val Arg Ser
            335                 340                 345

Asp Ser Ile Ile Phe Gln Phe Thr Lys Cys Cys Pro Pro Lys Pro
            350                 355                 360

Lys Asp Lys Ser Asn Leu Leu Val Phe Arg Thr Asn Gly Val Ser
            365                 370                 375

Asp Val Gln Leu Ser Pro Thr Leu Gln Arg His Asn Asn Val Asn
            380                 385                 390

Gln Met Val Phe His Lys Ile Arg Asn Glu Asp Leu Ile Phe Asn
            395                 400                 405

Glu Ser Leu Gly Gln Gly Thr Phe Thr Lys Ile Phe Lys Gly Val
            410                 415                 420

Arg Arg Glu Val Gly Asp Tyr Gly Gln Leu His Glu Thr Glu Val
            425                 430                 435

Leu Leu Lys Val Leu Asp Lys Ala His Arg Asn Tyr Ser Glu Ser
            440                 445                 450

Phe Phe Glu Ala Ala Ser Met Met Ser Gln Leu Ser His Lys His
            455                 460                 465

Leu Val Leu Asn Tyr Gly Val Cys Val Cys Gly Glu Glu Asn Ile
            470                 475                 480

Leu Val Gln Glu Phe Val Lys Phe Gly Ser Leu Asp Thr Tyr Leu
            485                 490                 495

Lys Lys Asn Lys Asn Ser Ile Asn Ile Leu Trp Lys Leu Gly Val
```

|     |     |     |     |     |     |     |     |     |     |     |     |     |
|-----|-----|-----|-----|-----|-----|-----|-----|-----|-----|-----|-----|-----|
|     |     |     |     | 500 |     |     |     | 505 |     |     |     | 510 |
| Ala | Lys | Gln | Leu | Ala | Trp | Ala | Met | His | Phe | Leu | Glu | Glu | Lys | Ser |
|     |     |     |     | 515 |     |     |     | 520 |     |     |     | 525 |
| Leu | Ile | His | Gly | Asn | Val | Cys | Ala | Lys | Asn | Ile | Leu | Leu | Ile | Arg |
|     |     |     |     | 530 |     |     |     | 535 |     |     |     | 540 |
| Glu | Glu | Asp | Arg | Arg | Thr | Gly | Asn | Pro | Phe | Ile | Lys | Leu | Ser | Asp |
|     |     |     |     | 545 |     |     |     | 550 |     |     |     | 555 |
| Pro | Gly | Ile | Ser | Ile | Thr | Val | Leu | Pro | Lys | Asp | Ile | Ser | Ser | Cys |
|     |     |     |     | 560 |     |     |     | 565 |     |     |     | 570 |
| Cys | Phe | Gln | Val | Leu | Gln | Glu | Arg | Ile | Pro | Trp | Val | Pro | Pro | Glu |
|     |     |     |     | 575 |     |     |     | 580 |     |     |     | 585 |
| Cys | Ile | Glu | Asn | Pro | Lys | Asn | Leu | Thr | Leu | Ala | Thr | Asp | Lys | Trp |
|     |     |     |     | 590 |     |     |     | 595 |     |     |     | 600 |
| Ser | Phe | Gly | Thr | Thr | Leu | Trp | Glu | Ile | Cys | Ser | Gly | Gly | Asp | Lys |
|     |     |     |     | 605 |     |     |     | 610 |     |     |     | 615 |
| Pro | Leu | Ser | Ala | Leu | Asp | Ser | Gln | Arg | Lys | Leu | Gln | Phe | Tyr | Glu |
|     |     |     |     | 620 |     |     |     | 625 |     |     |     | 630 |
| Asp | Lys | His | Gln | Leu | Pro | Ala | Pro | Lys | Trp | Thr | Glu | Leu | Ala | Asn |
|     |     |     |     | 635 |     |     |     | 640 |     |     |     | 645 |
| Leu | Ile | Asn | Asn | Cys | Met | Asp | Tyr | Glu | Pro | Asp | Phe | Arg | Pro | Ala |
|     |     |     |     | 650 |     |     |     | 655 |     |     |     | 660 |
| Phe | Arg | Ala | Val | Ile | Arg | Asp | Leu | Asn | Ser | Leu | Phe | Thr | Pro | Asp |
|     |     |     |     | 665 |     |     |     | 670 |     |     |     | 675 |
| Tyr | Glu | Leu | Leu | Thr | Glu | Asn | Asp | Met | Leu | Pro | Asn | Met | Arg | Ile |
|     |     |     |     | 680 |     |     |     | 685 |     |     |     | 690 |
| Gly | Ala | Leu | Gly | Phe | Ser | Gly | Ala | Phe | Glu | Asp | Arg | Asp | Pro | Thr |
|     |     |     |     | 695 |     |     |     | 700 |     |     |     | 705 |
| Gln | Phe | Glu | Glu | Arg | His | Leu | Lys | Phe | Leu | Gln | Gln | Leu | Gly | Lys |
|     |     |     |     | 710 |     |     |     | 715 |     |     |     | 720 |
| Gly | Asn | Phe | Gly | Ser | Val | Glu | Met | Cys | Arg | Tyr | Asp | Pro | Leu | Gln |
|     |     |     |     | 725 |     |     |     | 730 |     |     |     | 735 |
| Asp | Asn | Thr | Gly | Glu | Val | Val | Ala | Val | Lys | Lys | Leu | Gln | His | Ser |
|     |     |     |     | 740 |     |     |     | 745 |     |     |     | 750 |
| Thr | Glu | Glu | His | Leu | Arg | Asp | Phe | Glu | Arg | Glu | Ile | Glu | Ile | Leu |
|     |     |     |     | 755 |     |     |     | 760 |     |     |     | 765 |
| Lys | Ser | Leu | Gln | His | Asp | Asn | Ile | Val | Lys | Tyr | Lys | Gly | Val | Cys |
|     |     |     |     | 770 |     |     |     | 775 |     |     |     | 780 |
| Tyr | Ser | Ala | Gly | Arg | Arg | Asn | Leu | Arg | Leu | Ile | Met | Glu | Tyr | Leu |
|     |     |     |     | 785 |     |     |     | 790 |     |     |     | 795 |
| Pro | Tyr | Gly | Ser | Leu | Arg | Asp | Tyr | Leu | Gln | Lys | His | Lys | Glu | Arg |
|     |     |     |     | 800 |     |     |     | 805 |     |     |     | 810 |
| Ile | Asp | His | Lys | Lys | Leu | Leu | Gln | Tyr | Thr | Ser | Gln | Ile | Cys | Lys |
|     |     |     |     | 815 |     |     |     | 820 |     |     |     | 825 |
| Gly | Met | Glu | Tyr | Leu | Gly | Thr | Lys | Arg | Tyr | Ile | His | Arg | Asp | Leu |
|     |     |     |     | 830 |     |     |     | 835 |     |     |     | 840 |
| Ala | Thr | Arg | Asn | Ile | Leu | Val | Glu | Asn | Glu | Asn | Arg | Val | Lys | Ile |
|     |     |     |     | 845 |     |     |     | 850 |     |     |     | 855 |
| Gly | Asp | Phe | Gly | Leu | Thr | Lys | Val | Leu | Pro | Gln | Asp | Lys | Glu | Tyr |
|     |     |     |     | 860 |     |     |     | 865 |     |     |     | 870 |
| Tyr | Lys | Val | Lys | Glu | Pro | Gly | Glu | Ser | Pro | Ile | Phe | Trp | Tyr | Ala |
|     |     |     |     | 875 |     |     |     | 880 |     |     |     | 885 |
| Pro | Glu | Ser | Leu | Thr | Glu | Ser | Lys | Phe | Ser | Val | Ala | Ser | Asp | Val |
|     |     |     |     | 890 |     |     |     | 895 |     |     |     | 900 |

| | | | | | | | | | | | | | | |
|---|---|---|---|---|---|---|---|---|---|---|---|---|---|---|
|Trp|Ser|Phe|Gly|Val 905|Val|Leu|Tyr|Glu|Leu 910|Phe|Thr|Tyr|Ile|Glu 915|
|Lys|Ser|Lys|Ser|Pro 920|Pro|Val|Glu|Phe|Met 925|Arg|Met|Ile|Gly|Asn 930|
|Asp|Lys|Gln|Gly|Gln 935|Met|Ile|Val|Phe|His 940|Leu|Ile|Glu|Leu|Leu 945|
|Lys|Ser|Asn|Gly|Arg 950|Leu|Pro|Arg|Pro|Glu 955|Gly|Cys|Pro|Asp|Glu 960|
|Ile|Tyr|Val|Ile|Met 965|Thr|Glu|Cys|Trp|Asn 970|Asn| | | | |

( 2 ) INFORMATION FOR SEQ ID NO:20:

( i ) SEQUENCE CHARACTERISTICS:
        ( A ) LENGTH: 1184 amino acids
        ( B ) TYPE: amino acid
        ( D ) TOPOLOGY: linear ( x i ) SEQUENCE DESCRIPTION: SEQ ID NO:20:

| | | | | | | | | | | | | | | |
|---|---|---|---|---|---|---|---|---|---|---|---|---|---|---|
|Met|Pro|Leu|Arg|His 5|Trp|Gly|Met|Ala|Arg 10|Gly|Ser|Lys|Pro|Val 15|
|Gly|Asp|Gly|Ala|Gln 20|Pro|Met|Ala|Ala|Met 25|Gly|Gly|Leu|Lys|Val 30|
|Leu|Leu|His|Trp|Ala 35|Gly|Pro|Gly|Gly|Gly 40|Glu|Pro|Trp|Val|Thr 45|
|Phe|Ser|Glu|Ser|Ser 50|Leu|Ile|Ala|Glu|Val 55|Cys|Ile|His|Ile|Ile 60|
|Ala|His|Lys|Val|Gly 65|Ile|Thr|Pro|Pro|Cys 70|Phe|Asn|Leu|Phe|Ala 75|
|Leu|Phe|Asp|Ala|Gln 80|Ala|Gln|Val|Trp|Leu 85|Pro|Pro|Asn|His|Ile 90|
|Leu|Glu|Ile|Pro|Arg 95|Asp|Ala|Ser|Leu|Met 100|Leu|Tyr|Phe|Arg|Ile 105|
|Arg|Phe|Tyr|Phe|Arg 110|Asn|Trp|His|Gly|Met 115|Asn|Pro|Arg|Glu|Pro 120|
|Ala|Gly|Tyr|Arg|Cys 125|Gly|Pro|Pro|Gly|Thr 130|Glu|Ala|Ser|Ser|Asp 135|
|Gln|Thr|Ala|Gln|Gly 140|Met|Gln|Leu|Leu|Asp 145|Pro|Ala|Ser|Phe|Glu 150|
|Tyr|Leu|Phe|Glu|Gln 155|Gly|Lys|His|Glu|Phe 160|Glu|Asn|Asp|Val|Ala 165|
|Ser|Leu|Trp|Glu|Leu 170|Ser|Thr|Glu|Glu|Glu 175|Ile|His|His|Phe|Lys 180|
|Asn|Glu|Ser|Leu|Gly 185|Met|Ala|Phe|Leu|His 190|Leu|Cys|His|Leu|Ala 195|
|Leu|Arg|His|Gly|Ile 200|Pro|Leu|Glu|Glu|Val 205|Ala|Lys|Lys|Thr|Ser 210|
|Phe|Lys|Asp|Cys|Ile 215|Pro|Arg|Ser|Phe|Arg 220|Arg|His|Ile|Arg|Gln 225|
|His|Ser|Ala|Leu|Thr 230|Arg|Leu|Arg|Leu|Arg 235|Asn|Val|Phe|Arg|Arg 240|
|Phe|Leu|Arg|Asp|Phe 245|Gln|Pro|Gly|Arg|Leu 250|Ser|Gln|Gln|Met|Val 255|
|Met|Val|Lys|Tyr|Leu 260|Ala|Thr|Leu|Glu|Arg 265|Leu|Ala|Pro|Arg|Phe 270|
|Gly|Thr|Glu|Arg|Val|Pro|Val|Cys|His|Leu|Arg|Leu|Leu|Ala|Gln|

-continued

| | | | | 275 | | | | | 280 | | | | | 285 |
|---|---|---|---|---|---|---|---|---|---|---|---|---|---|---|
| Ala | Glu | Gly | Glu | Pro | Cys | Tyr | Ile | Arg | Asp | Ser | Gly | Val | Ala | Pro |
| | | | | 290 | | | | | 295 | | | | | 300 |
| Thr | Asp | Pro | Gly | Pro | Glu | Ser | Ala | Ala | Gly | Pro | Pro | Thr | His | Glu |
| | | | | 305 | | | | | 310 | | | | | 315 |
| Val | Leu | Val | Thr | Gly | Thr | Gly | Gly | Ile | Gln | Trp | Trp | Pro | Val | Glu |
| | | | | 320 | | | | | 325 | | | | | 330 |
| Glu | Glu | Val | Asn | Lys | Glu | Glu | Gly | Ser | Ser | Gly | Ser | Ser | Ala | Arg |
| | | | | 335 | | | | | 340 | | | | | 345 |
| Asn | Pro | Gln | Ala | Ser | Leu | Phe | Gly | Lys | Lys | Ala | Lys | Ala | His | Lys |
| | | | | 350 | | | | | 355 | | | | | 360 |
| Ala | Phe | Gly | Gln | Pro | Ala | Asp | Arg | Pro | Arg | Glu | Pro | Leu | Trp | Ala |
| | | | | 365 | | | | | 370 | | | | | 375 |
| Tyr | Phe | Cys | Asp | Ile | Thr | His | Val | Val | Leu | Lys | Glu | His | Cys | Val |
| | | | | 380 | | | | | 385 | | | | | 390 |
| Ser | Ile | His | Arg | Gln | Asp | Asn | Lys | Cys | Leu | Glu | Leu | Ser | Leu | Pro |
| | | | | 395 | | | | | 400 | | | | | 405 |
| Ser | Arg | Ala | Ala | Ala | Leu | Ser | Phe | Glu | Ser | Leu | Val | Asp | Gly | Tyr |
| | | | | 410 | | | | | 415 | | | | | 420 |
| Phe | Arg | Leu | Thr | Ala | Asp | Ser | Ser | His | Tyr | Leu | Cys | His | Glu | Val |
| | | | | 425 | | | | | 430 | | | | | 435 |
| Ala | Pro | Pro | Arg | Leu | Val | Met | Ser | Ile | Arg | Asp | Gly | Ile | His | Gly |
| | | | | 440 | | | | | 445 | | | | | 450 |
| Pro | Leu | Leu | Glu | Pro | Phe | Val | Gln | Gln | Ala | Lys | Leu | Arg | Pro | Leu |
| | | | | 455 | | | | | 460 | | | | | 465 |
| Glu | Asp | Gly | Leu | Tyr | Leu | Ile | His | Trp | Ser | Thr | Ser | His | Pro | Tyr |
| | | | | 470 | | | | | 475 | | | | | 480 |
| Arg | Leu | Ile | Leu | Thr | Val | Ala | Gln | Arg | Ser | Gln | Ala | Pro | Asp | Gly |
| | | | | 485 | | | | | 490 | | | | | 495 |
| Met | Gln | Ser | Leu | Arg | Leu | Arg | Lys | Phe | Pro | Ile | Glu | Gln | Gln | Asp |
| | | | | 500 | | | | | 505 | | | | | 510 |
| Gly | Ala | Phe | Val | Leu | Glu | Gly | Trp | Gly | Arg | Ser | Phe | Pro | Ser | Val |
| | | | | 515 | | | | | 520 | | | | | 525 |
| Arg | Glu | Leu | Gly | Ala | Ala | Leu | Gln | Gly | Cys | Leu | Leu | Arg | Ala | Gly |
| | | | | 530 | | | | | 535 | | | | | 540 |
| Asp | Asp | Cys | Phe | Ser | Leu | Arg | Arg | Cys | Cys | Leu | Pro | Gln | Pro | Gly |
| | | | | 545 | | | | | 550 | | | | | 555 |
| Glu | Thr | Ser | Asn | Leu | Ile | Ile | Met | Arg | Gly | Ala | Arg | Ala | Ser | Pro |
| | | | | 560 | | | | | 565 | | | | | 570 |
| Arg | Thr | Leu | Asn | Leu | Ser | Gln | Leu | Ser | Phe | His | Arg | Val | Asp | Gln |
| | | | | 575 | | | | | 580 | | | | | 585 |
| Lys | Glu | Ile | Thr | Gln | Leu | Ser | His | Leu | Gly | Gln | Gly | Thr | Arg | Thr |
| | | | | 590 | | | | | 595 | | | | | 600 |
| Asn | Val | Tyr | Glu | Gly | Arg | Leu | Arg | Val | Glu | Gly | Ser | Gly | Asp | Pro |
| | | | | 605 | | | | | 610 | | | | | 615 |
| Glu | Glu | Gly | Lys | Met | Asp | Asp | Glu | Asp | Pro | Leu | Val | Pro | Gly | Arg |
| | | | | 620 | | | | | 625 | | | | | 630 |
| Asp | Arg | Gly | Gln | Glu | Leu | Arg | Val | Val | Leu | Lys | Val | Leu | Asp | Pro |
| | | | | 635 | | | | | 640 | | | | | 645 |
| Ser | His | His | Asp | Ile | Ala | Leu | Ala | Phe | Tyr | Glu | Thr | Ala | Ser | Leu |
| | | | | 650 | | | | | 655 | | | | | 660 |
| Met | Ser | Gln | Val | Ser | His | Thr | His | Leu | Ala | Phe | Val | His | Gly | Val |
| | | | | 665 | | | | | 670 | | | | | 675 |

-continued

| | | | | | | | | | | | | | | |
|---|---|---|---|---|---|---|---|---|---|---|---|---|---|---|
| Cys | Val | Arg | Gly | Pro 680 | Glu | Asn | Ser | Met | Val 685 | Thr | Glu | Tyr | Val | Glu 690 |
| His | Gly | Pro | Leu | Asp 695 | Val | Trp | Leu | Arg | Arg 700 | Glu | Arg | Gly | His | Val 705 |
| Pro | Met | Ala | Trp | Lys 710 | Met | Val | Val | Ala | Gln 715 | Gln | Leu | Ala | Ser | Ala 720 |
| Leu | Ser | Tyr | Leu | Glu 725 | Asn | Lys | Asn | Leu | Val 730 | His | Gly | Asn | Val | Cys 735 |
| Gly | Arg | Asn | Ile | Leu 740 | Leu | Ala | Arg | Leu | Gly 745 | Leu | Ala | Glu | Gly | Thr 750 |
| Ser | Pro | Phe | Ile | Lys 755 | Leu | Ser | Asp | Pro | Gly 760 | Cys | Gly | Leu | Gly | Ala 765 |
| Leu | Ser | Arg | Glu | Glu 770 | Arg | Val | Glu | Arg | Ile 775 | Pro | Trp | Leu | Ala | Pro 780 |
| Glu | Cys | Leu | Pro | Gly 785 | Gly | Ala | Asn | Ser | Leu 790 | Ser | Thr | Ala | Met | Asp 795 |
| Lys | Trp | Gly | Phe | Gly 800 | Ala | Thr | Leu | Leu | Glu 805 | Ile | Cys | Phe | Asp | Gly 810 |
| Glu | Ala | Pro | Leu | Gln 815 | Ser | Arg | Ser | Pro | Ser 820 | Glu | Lys | Glu | His | Phe 825 |
| Tyr | Gln | Arg | Gln | His 830 | Arg | Leu | Pro | Glu | Pro 835 | Ser | Cys | Pro | Gln | Leu 840 |
| Ala | Thr | Leu | Thr | Ser 845 | Gln | Cys | Leu | Thr | Tyr 850 | Glu | Pro | Thr | Gln | Arg 855 |
| Pro | Ser | Phe | Ala | Thr 860 | Ile | Leu | Arg | Asp | Leu 865 | Thr | Arg | Val | Gln | Pro 870 |
| His | Asn | Leu | Ala | Asp 875 | Val | Leu | Thr | Val | Asn 880 | Arg | Asp | Ser | Pro | Ala 885 |
| Val | Gly | Pro | Thr | Thr 890 | Phe | His | Lys | Arg | Tyr 895 | Leu | Lys | Lys | Ile | Arg 900 |
| Asp | Leu | Gly | Glu | Gly 905 | His | Phe | Gly | Lys | Val 910 | Ser | Leu | Tyr | Cys | Tyr 915 |
| Asp | Pro | Thr | Asn | Asp 920 | Gly | Thr | Gly | Glu | Met 925 | Val | Ala | Val | Lys | Ala 930 |
| Leu | Lys | Ala | Asp | Cys 935 | Gly | Pro | Gln | His | Arg 940 | Ser | Gly | Trp | Lys | Gln 945 |
| Glu | Ile | Asp | Ile | Leu 950 | Arg | Thr | Leu | Tyr | His 955 | Glu | His | Ile | Ile | Lys 960 |
| Tyr | Lys | Gly | Cys | Cys 965 | Glu | Asp | Gln | Gly | Glu 970 | Lys | Ser | Leu | Val | Met 975 |
| Glu | Tyr | Val | Pro | Leu 980 | Gly | Ser | Leu | Arg | Asp 985 | Tyr | Leu | Pro | Arg | His 990 |
| Ser | Ile | Gly | Leu | Ala 995 | Gln | Leu | Leu | Leu | Phe 1000 | Ala | Gln | Gln | Ile | Cys 1005 |
| Glu | Gly | Met | Ala | Tyr 1010 | Leu | His | Ala | His | Asp 1015 | Tyr | Ile | His | Arg | Asp 1020 |
| Leu | Ala | Ala | Arg | Asn 1025 | Val | Leu | Leu | Asp | Asn 1030 | Asp | Arg | Leu | Val | Lys 1035 |
| Ile | Gly | Asp | Phe | Gly 1040 | Leu | Ala | Lys | Ala | Val 1045 | Pro | Glu | Gly | His | Glu 1050 |
| Tyr | Tyr | Arg | Val | Arg 1055 | Glu | Asp | Gly | Asp | Ser 1060 | Pro | Val | Phe | Trp | Tyr 1065 |
| Ala | Pro | Glu | Cys | Leu 1070 | Lys | Glu | Tyr | Asn | Phe 1075 | Tyr | Tyr | Ala | Ser | Asp 1080 |

```
Val  Trp  Ser  Phe  Gly  Val  Thr  Leu  Tyr  Glu  Leu  Leu  Thr  His  Cys
               1085           1090                     1095

Asp  Ser  Ser  Gln  Ser  Pro  Pro  Thr  Lys  Phe  Leu  Glu  Leu  Ile  Gly
               1100           1105                     1110

Ile  Ala  Gln  Gly  Gln  Met  Thr  Val  Leu  Arg  Leu  Thr  Glu  Leu  Leu
               1115           1120                     1125

Glu  Arg  Gly  Glu  Arg  Leu  Pro  Arg  Pro  Asp  Lys  Cys  Pro  Cys  Glu
               1130           1135                     1140

Val  Tyr  His  Leu  Met  Lys  Asn  Cys  Trp  Glu  Thr  Glu  Ala  Ser  Phe
               1145           1150                     1155

Arg  Pro  Thr  Phe  Glu  Asn  Ser  Ile  Pro  Ile  Leu  Lys  Thr  Val  His
               1160           1165                     1170

Glu  Lys  Tyr  Gln  Gly  Gln  Ala  Pro  Ser  Val  Ser  Ser  Val  Cys
               1175           1180
```

( 2 ) INFORMATION FOR SEQ ID NO:21:

( i ) SEQUENCE CHARACTERISTICS:
    ( A ) LENGTH: 92 amino acids
    ( B ) TYPE: amino acid
    ( D ) TOPOLOGY: linear ( x i ) SEQUENCE DESCRIPTION: SEQ ID NO:21:

```
Trp  Tyr  His  Gly  Lys  Leu  Asp  Arg  Thr  Ile  Ala  Glu  Glu  Arg  Leu
               5                   10                     15

Arg  Gln  Ala  Gly  Lys  Ser  Gly  Ser  Tyr  Leu  Ile  Arg  Glu  Ser  Asp
               20                  25                     30

Arg  Arg  Pro  Gly  Ser  Phe  Val  Leu  Ser  Phe  Leu  Ser  Gln  Thr  Asn
               35                  40                     45

Val  Val  Asn  His  Phe  Arg  Ile  Ile  Ala  Met  Cys  Gly  Asp  Tyr  Tyr
               50                  55                     60

Ile  Gly  Gly  Arg  Arg  Phe  Ser  Ser  Leu  Ser  Asp  Leu  Ile  Gly  Tyr
               65                  70                     75

Tyr  Ser  His  Val  Ser  Cys  Leu  Leu  Lys  Gly  Glu  Lys  Leu  Leu  Tyr
               80                  85                     90

Pro  Val
```

( 2 ) INFORMATION FOR SEQ ID NO:22:

( i ) SEQUENCE CHARACTERISTICS:
    ( A ) LENGTH: 91 amino acids
    ( B ) TYPE: amino acid
    ( D ) TOPOLOGY: linear ( x i ) SEQUENCE DESCRIPTION: SEQ ID NO:22:

```
Trp  Phe  His  Gly  Lys  Ile  Ser  Lys  Gln  Glu  Ala  Tyr  Asn  Leu  Leu
               5                   10                     15

Met  Thr  Val  Gly  Gln  Ala  Cys  Ser  Phe  Leu  Val  Arg  Pro  Ser  Asp
               20                  25                     30

Asn  Thr  Pro  Gly  Asp  Tyr  Ser  Leu  Tyr  Phe  Arg  Thr  Ser  Glu  Asn
               35                  40                     45

Ile  Gln  Arg  Phe  Lys  Ile  Cys  Pro  Thr  Pro  Asn  Asn  Gln  Phe  Met
               50                  55                     60

Met  Gly  Gly  Arg  Tyr  Tyr  Asn  Ser  Ile  Gly  Asp  Ile  Ile  Asp  His
               65                  70                     75

Tyr  Arg  Lys  Glu  Gln  Ile  Val  Glu  Gly  Tyr  Tyr  Leu  Lys  Glu  Pro
               80                  85                     90
```

Val ( 2 ) INFORMATION FOR SEQ ID NO: 23:

( i ) SEQUENCE CHARACTERISTICS:
      ( A ) LENGTH: 89 amino acids
      ( B ) TYPE: amino acid
      ( D ) TOPOLOGY: linear ( x i ) SEQUENCE DESCRIPTION: SEQ ID NO: 23:

```
Trp Tyr Trp Gly Arg Leu Ser Arg Gly Asp Ala Val Ser Leu Leu
                 5                  10                  15

Gln Gly Gln Arg His Gly Thr Phe Leu Val Arg Asp Ser Gly Ser
                 20                  25                  30

Ile Pro Gly Asp Phe Val Leu Ser Val Ser Glu Ser Ser Arg Val
                 35                  40                  45

Ser His Tyr Ile Val Asn Ser Leu Gly Pro Ala Gly Gly Arg Arg
                 50                  55                  60

Ala Gly Gly Glu Phe Asp Ser Leu Pro Ser Leu Leu Glu Phe Tyr
                 65                  70                  75

Lys Ile His Tyr Leu Asp Thr Thr Thr Leu Ile Glu Pro Val
                 80                  85
```